US005785967A

United States Patent [19]

Gearing et al.

[11] Patent Number: 5,785,967
[45] Date of Patent: Jul. 28, 1998

[54] ANTIBODIES IMMUNOREACTIVE WITH LEUKEMIA INHIBITORY FACTOR RECEPTORS

[75] Inventors: David P. Gearing, Seattle; Patricia M. Beckmann, Poulsbo, both of Wash.

[73] Assignee: Immunex Corporation, Seattle, Wash.

[21] Appl. No.: 347,003

[22] Filed: Nov. 29, 1994

Related U.S. Application Data

[62] Division of Ser. No. 119,780, Sep. 10, 1993, Pat. No. 5,420,247, which is a division of Ser. No. 943,843, Sep. 11, 1992, Pat. No. 5,284,755, which is a continuation-in-part of Ser. No. 670,608, Mar. 13, 1991, abandoned, which is a continuation-in-part of Ser. No. 626,725, Dec. 13, 1990, abandoned.

[51] Int. Cl.$^6$ .................. A61K 39/395; A61K 39/40; C07K 16/00; C12P 21/08
[52] U.S. Cl. .................. 424/139.1; 424/143.1; 435/331; 435/334; 530/388.22
[58] Field of Search .................. 530/388.22; 424/139.1, 424/143.1; 435/331, 334

[56] References Cited

U.S. PATENT DOCUMENTS

| 4,518,584 | 5/1985  | Mark et al.        | 424/85  |
|-----------|---------|--------------------|---------|
| 4,675,285 | 6/1987  | Clark et al.       | 435/6   |
| 5,071,972 | 12/1991 | Larsen             | 536/27  |
| 5,155,027 | 10/1992 | Sledziewski et al. | 435/69.7|
| 5,262,522 | 11/1993 | Gearing et al.     | 530/350 |

FOREIGN PATENT DOCUMENTS

| 0212914    | 4/1987 | European Pat. Off. . |
| 0276846    | 3/1988 | European Pat. Off. . |
| WO 94/01464| 1/1994 | WIPO .               |

OTHER PUBLICATIONS

Allan et al., "Osteoblasts display receptors for and responses to leukemia–inhibitory factor", *J. Cell. Physiol.*145:110–119; 1990.

Williams et al., "Myeloid leukemia inhibitory factor maintains the development potential of embryonic stem cell", *Nature*336:684–687; 1988.

Tomida et al., "Inhibition of development of NA⁺dependent hexose transport in renal epithlial LLC–PK1 cells ... for myeloid leukemic cells/leukemia inhibitory factor", *FEBS*268:261–264; 1990.

Gearing et al., "Expression cloning of a receptor for human granulocyte–macrphage colony–stimulating factor", *EMBO J.*8:3667–3676; 1989.

Yamasaki et al., "Cloning and Expression of the Human Interleukin–6 Receptor", *Science*241:825–828; 1988.

Cosman, "Expression Cloning of Cytokines and Cytokine Receptors by Screening Pools of cDNA Clones", *DNA & Prot. Eng. Tech.*2:1–28, 1990.

Gearaing et al., "Leukemia inhibitory factor receptor is structurally related to the IL–6 signal transducer, gp130", *EMBO J.*10:2839; 1991.

Sims et al., "cDNA Expression Clonining of the IL–1 Receptor: a Member of the Immunoglobulin Superfamily", *Science*241:585–589; 1988.

Belyavsky et al., "PCR–based cDNA Library Construction; General cDNA Libraries at the Level of a Few Cells", *Nucl. Acids Res.*17; Aug. 1989.

Smith et al., "Blocking of HIV–I Infectivity by a Soluble, Secreted Form of the CD4 Antigen", *Science*238:1704–1707; 1987.

Baumann and Wong, "Hepatocyte–Stimulating Factor III Shares Structural and Functional Identity with Leukemia Inhibitory Factor", *J. Immunol.*143:1163; 1989.

Yamamori et al., "The Cholinergic Neuronal Differentiation Factor from Heart Cells is Identical to Leukemia Inhibitory Factor", *Science*246:1412; 1990.

Mori et al., "Purification of a Lipoprotein Lipase–Inhibiting Protein Produced by a Melanoma Cell Line Associated with Cancer Cachexia" *Biochem. Biophys. Res. Comm.*160:1085; 1989.

Moreau et al., "Leukaemia inhibitory factor is identical to the myeloid growth factor human interleukin for DA cells", *Nature*336:690; 1988.

Abe et al., "Macrophage Differentiation Inducing Factor from Human Monocytic Cells is Equivalent to Murine Leukemia Inhibitory Factor", *J. Biol. Chem.*264:8941; 1989.

Smith and Hooper, "Buffalo Rat Liver Cells Produce a Diffusable Activity Which Inhibits the Differentiation of Murine Embryonal Carcinoma and Embryonic Stem Cells", *Devel. Biol.*121:1; 1987.

Koopman and Cotton, "A Factor Produced by Feeder Cells which Inhibits Embryonal Carcinoma Cell Differentiation", *Exp. Cell. Res.*154:233; 1984.

Tomida et al., "Purification of a Factor Inducing Differentiation of Mouse Myeloid Leukemic M1Cells from Conditioned Medium of Mouse Fibroblast L929 Cells" *J.Biol. Chem.*259:10978; 1984.

Hilton et al., "Resolution and Purification of Three Distinct Factors Produced ny Krebs Ascites Cells Which Have Differentiation–inducing Activity on Murine Myeloid Leukemic Cell Lines", *J. Biol. Chem.*263:9238; 1988.

Gough et al., "Molecular cloning and expression of the human homologue of the murine gene encoding myeloid leukemia–inhibitory factor", *Proc. Natl. Acad. Sci. USA*85:2623; 1988.

Metcalf et al., "Effects of Injected Leukemia Inhibitory Factor on Hematopoietic and Other Tissues on Mice", *Blood*76:50; 1990.

(List continued on next page.)

*Primary Examiner*—Anthony C. Caputa
*Assistant Examiner*—Mark Navarro
*Attorney, Agent, or Firm*—Kathryn A. Anderson; Janis C. Henry

[57] ABSTRACT

Leukemia inhibitory factor receptor (LIF-R) proteins, DNAs and expression vectors encoding LIF-R, and processes for producing LIF-R as products of recombinant cell culture, and antibodies that are immunoreactive with LIF-R are disclosed.

8 Claims, 8 Drawing Sheets

OTHER PUBLICATIONS

Hilton et al., "Specific Binding of Murine Leukemia Inhibitory Factor to Normal and Leukemic Monocytic Cells", *Proc. Natl. Acad. Sci. USA* 85:5971; 1988.

Jacques et al., "High–Affinity Receptors for Human HILDA/LIF on Human Cell Lines", *5th Symposium sur les Marquers de l'Inflammation*, (Lyon 25–27 Sep. 1990).

Hilton et al., "Distribution of LIF receptors during embryogenesis", Article 45, *Annual Review*, The Walter and Eliza Hall Institute of Medical Research; 1990.

Brown et al., "Anaysis of leukaemia inhibitory factor expression", Article 55, *Annual Review*, The Walter and Eliza Hall Institute of Medical Research; Jun. 1989 –Jul. 1990.

Stewart et al., "Blastocyte implantation depends on maternal expression of leukaemia inhibitory factor", *Nature* 359:76–79; 1992.

Heath, "Can there be life without LIF?", *Nature* 359:17; 1992.

Hilton et al., "Distribution and Comparison of Receptors for Leukemia Inhibitory Factor on Murine Hematopoietic and Hepatic Cells", *J. Cell. Phys.* 146:207–215; 1991.

Gearing and Bruce, "Oncostatin M Binds the High–Affinity Leukemia Inhibitory Factor Receptor", *The New Biologist* 4:61–65; 1992.

Gearing, "Leukemia Inhibitory Factor: Does the Cap Fit?", *Ann. of the N.Y. Acad. Sci.* 628:9–18; 1991.

Gearing et al., "The IL–6 Signal Transducer, gp130: An Oncostatin M Receptor and Affinity Converter for the LIF Receptor", *Science* 255:1434–1437; 1992.

Aruffo and Seed, "Molecular cloning of a CD28 cDNA by a high–efficiency COS cell expression system", *Proc. Natl. Acad. Sci. USA* 84:8573–8577; 1987.

Lesslauer et al., "Recombinant soluble tumor necrosis factor receptor proteins protect mice from lipopolysaccharide–induced lethality", *Eur. J. Immunol.* 21:2883–2886; 1991.

Peppel and Beutler, "Chimaeric TNF–Receptor –IgG Molecule Acts as Soluble Inhibitor of TNF Mediated Cytotoxicity", *J. Cell. Biochem. (ABSTR)*, Suppl. 15F; Apr. 1991.

Owezarek et al., (J. of Biol. Chem. vol. 271, (10) Mar. 8, 1996 pp. 5495–5504).

Layton et al., (Proc. of the Society For Experimental Biology +Medicine Jul. 1994 vol. 206(3) pp. 295–298).

Sevier et al., (clinical chemistry vol. 27, No. 11 pp. 1797–1806, 1981).

FIGURE 2a

872  CTC GAA GAG TGG AGT GAC TGG AGC CCT GTG AAG AAC ATT TCT TGG ATA CCT GAT TCT CAG ACT AAG GTT TTT CCT CAA GAT AAA GTG ATA CTT GTA GGC  970
232  Leu Glu Glu Trp Ser Asp Trp Ser Pro Val Lys Asn Ile Ser Trp Ile Pro Asp Ser Gln Thr Lys Val Phe Pro Gln Asp Lys Val Ile Leu Val Gly  264

971  TCA GAC ATA ACA TTT TGT TGT GTG AGT CAA GAA AAA GTG TTA TCA GCA CTG ATT GGC CAT ACA AAC TGC CCC TTG ATC CAT CTT GAT GGG GAA AAT GTT  1069
265  Ser Asp Ile Thr Phe Cys Cys Val Ser Gln Glu Lys Val Leu Ser Ala Leu Ile Gly His Thr Asn Cys Pro Leu Ile His Leu Asp Gly Glu Asn Val  297

1070 GCA ATC AAG ATT CGT AAT ATT TCT GTT TCT GCA AGT AGT GGA ACA AAT GTA GTT TTT ACA ACC GAA GAT AAC ATA TTT GGA ACC GTT ATT TTT GCT GGA  1168
298  Ala Ile Lys Ile Arg Asn Ile Ser Val Ser Ala Ser Ser Gly Thr Asn Val Val Phe Thr Thr Glu Asp Asn Ile Phe Gly Thr Val Ile Phe Ala Gly  330

1169 TAT CCA CCA GAT ACT CCT CAA CAA CTG AAT TGT GAG ACA CAT GAT TTA AAA GAA ATT ATA TGT AGT TGG AAT CCA GGA AGG GTG ACA GCG TTG GTG GGC  1267
331  Tyr Pro Pro Asp Thr Pro Gln Gln Leu Asn Cys Glu Thr His Asp Leu Lys Glu Ile Ile Cys Ser Trp Asn Pro Gly Arg Val Thr Ala Leu Val Gly  363

1268 CCA CGT GCT ACA AGC TAC ACT TTA GTT GAA AGT TTT TCA GGA AAA TAT GTT AGA CTT AAA AGA GCT CAC AAT CCG GGT CGA TCA CAA TCA ACA ATT CAA TTA TTA  1366
364  Pro Arg Ala Thr Ser Tyr Thr Leu Val Glu Ser Phe Ser Gly Lys Tyr Val Arg Leu Lys Arg Ala His Asn Pro Gly Arg Ser Gln Ser Thr Ile Gln Leu Leu  396

1367 TTT CAA ATG CTT CCA CAA ATA CAA GAA ATA TAT TTT ACT TTG AAT GCT CAC AAT CCG GGT CGA TCA CAA TCA ACA ATT GTT AAT ATA ACT GAA  1465
397  Phe Gln Met Leu Pro Gln Ile Gln Glu Ile Tyr Phe Thr Leu Asn Ala His Asn Pro Gly Arg Ser Gln Ser Thr Ile Val Asn Ile Thr Glu  429

1466 AAA GTT TAT CCC CAT ACT CCT ACT TCA AAA GTG AAG GAT ATT AAT TCA ACA GCT GTT AAA CTT TCT TGG CAT TTA CCA GGC AAC TTT GCA AAG ATT  1564
430  Lys Val Tyr Pro His Thr Pro Thr Ser Phe Lys Val Lys Asp Ile Asn Ser Thr Ala Val Lys Leu Ser Trp His Leu Pro Gly Asn Phe Ala Lys Ile  462

FIGURE 2b

```
1565  AAT TTT TTA TGT GAA ATT GAA ATT AAG AAA TCT AAT TCA GTA CAA GAG CAG CGG AAT GTC ACA ATC AAA GGA GTA GAA AAT TCA AGT CTT GTT GCT  1663
463   Asn Phe Leu Cys Glu Ile Glu Ile Lys Lys Ser Asn Ser Val Gln Glu Gln Arg Asn Val Thr Ile Lys Gly Val Glu Asn Ser Ser Tyr Leu Val Ala  495

1664  CTG GAC AAG TTA AAT CCA TAC ACT CTA TAT ACT TTT CGG ATT CCT TGT TCT ACT GAA ACT TTC TGG AAA TGG AGC AAA TGG AGC TGG TCA AAA AAA CAA CAT  1762
496   Leu Asp Lys Leu Asn Pro Tyr Thr Leu Tyr Thr Phe Arg Ile Pro Cys Ser Thr Glu Thr Phe Trp Lys Trp Ser Lys Trp Ser Trp Ser Lys Lys Gln His  528

1763  TTA ACA ACA GAA GCC AGT CCT TCA AAG GGG CCT GAT ACT TGG AGA GAG TGG AGT TCT GAT TGG AGT CCT GAT TGG CCA GAT TGG CGC TCA AAA ATA TTA CCC ATT  1861
529   Leu Thr Thr Glu Ala Ser Pro Ser Lys Gly Pro Asp Thr Trp Arg Glu Trp Ser Ser Asp Trp Ser Pro Asp Trp Arg Glu Ile Ile Tyr Trp Lys Pro Leu Pro Ile  561

1862  AAT GAA GCT AAA ATA TCC TAC AAT GTA TCG TGT TCA GAT GAA ACA CAG TCC CTT TCT GAA ATC CCT GAT CCT CAG CAC AAA GCA  1960
562   Asn Glu Ala Lys Ile Ser Tyr Asn Val Ser Cys Ser Asp Glu Thr Gln Ser Leu Ser Glu Ile Pro Asp Pro Gln His Lys Ala  594

1961  GAG ATA CGA CTT GAT AAG AAT GAC TAC ATC AGC GTA GTG GCT AAA AAT TCT GTG GGC TCA CCA CCT TCC AAA ATA GCG AGT ATG GAA ATT CCA  2059
595   Glu Ile Arg Leu Asp Lys Asn Asp Tyr Ile Ser Val Val Ala Lys Asn Ser Val Gly Ser Pro Pro Ser Lys Ile Ala Ser Met Glu Ile Pro  627

2060  AAT GAT GAT CTC AAA ATA GAA CAA GTT GTT GGG ATG GGA AAG GGG ATT CTC CTC ACC TGG CAT TAC GAC CCC AAC ATG ACT TGC GAC TAC GTC ATT AAG  2158
628   Asn Asp Asp Leu Lys Ile Glu Gln Val Val Gly Met Gly Lys Gly Ile Leu Leu Thr Trp His Tyr Asp Pro Asn Met Thr Cys Asp Tyr Val Ile Lys  660

2159  TGG TGT AAC TCG TCT CGG TCG GAA CCA TGC CTT ATG GAC TGG AGA AAA GTT CCC TCA AAC AGC ACT GAA TCT GAT GAA ACT GTA ATA GAA TCT GAG TTT CGA CCA  2257
661   Trp Cys Asn Ser Ser Arg Ser Glu Pro Cys Leu Met Asp Trp Arg Lys Val Pro Ser Asn Ser Thr Glu Ser Asp Glu Thr Val Ile Glu Ser Asp Glu Phe Arg Pro  693
```

FIGURE 2c

```
2258  GGT ATA AGA TAT AAT TTT TTC CTG TAT GGA TGC AGA AAT CAA GGA TAT ATA GAA GAA TTG GCT CCC ATT GTT  2356
694   Gly Ile Arg Tyr Asn Phe Phe Leu Tyr Gly Cys Arg Asn Gln Gly Tyr Ile Glu Glu Leu Ala Pro Ile Val  726

2357  GCA CCA AAT TTT ACT GTT GAG GAT ACT TCT GCA GAT TCG ATA TTA GTA AAA TGG GAA GAC ATT CCT GTG GAA GAA CTT AGA GGC TTT TTA AGA GGA TAT  2455
727   Ala Pro Asn Phe Thr Val Glu Asp Thr Ser Ala Asp Ser Ile Leu Val Lys Trp Glu Asp Ile Pro Val Glu Glu Leu Arg Gly Phe Leu Arg Gly Tyr  759
                                                                                                                                        *

2456  TTG TTT TAC TTT GGA AAA GGA GAA AGA GAC ACA TCT AAG ATG AGG GTT TTA GAA TCA GGT CGT TCT GAC ATA AAA GTT AAG AAT ATT ACT GAC ATA TCC  2554
760   Leu Phe Tyr Phe Gly Lys Gly Glu Arg Asp Thr Ser Lys Met Arg Val Leu Glu Ser Gly Arg Ser Asp Ile Lys Val Lys Asn Ile Thr Asp Ile Ser  792

2555  CAG AAG ACA CTG AGA ATT GCT GAT CTT GAA GGT AAA ACA AGT TAC CAC CTG GTC CGA GCC TAT ACA GAT GGT GGA GTG GGC CCG GAG AAG AGT ATG  2653
793   Gln Lys Thr Leu Arg Ile Ala Asp Leu Glu Gly Lys Thr Ser Tyr His Leu Val Arg Ala Tyr Thr Asp Gly Gly Val Gly Pro Glu Lys Ser Met  825

2654  TAT GTG GTG ACA AAG GAA AAT TCT GTG GGA TTA ATT ATT GCC ATT CTC ATC CCA GTG GCT GTC ATT GTT GGA GTG GTG ACA AGT AGT CTT TGC  2752
826   Tyr Val Val Thr Lys Glu Asn Ser Val Gly Leu Ile Ile Ala Ile Leu Ile Pro Val Ala Val Ile Val Gly Val Val Thr Ser Ile Leu Cys  858

2753  TAT CGG AAA CGA GAA TGG ATT AAA GAA ACC TTC CCT GAT ATT CCA AAT CCA GAA AAC TGT AAA GCA TTA CAG TTT CAA AAG AGT GTC TGT GAG GGA  2851
859   Tyr Arg Lys Arg Glu Trp Ile Lys Glu Thr Phe Pro Asp Ile Pro Asn Pro Glu Asn Cys Lys Ala Leu Gln Phe Gln Lys Ser Val Cys Glu Gly  891

2852  AGC AGT GCT CTT AAA ACA TTG GAA ATG AAT CCT TGT ACC CCA AAT AAT GTT GAG GTT CTG GAA ACT CGA TCA GCA TTT CCT AAA ATA GAA GAT ACA GAA  2950
892   Ser Ser Ala Leu Lys Thr Leu Glu Met Asn Pro Cys Thr Pro Asn Asn Val Glu Val Leu Glu Thr Arg Ser Ala Phe Pro Lys Ile Glu Asp Thr Glu  924
```

FIGURE 2d

```
2951 ATA ATT TCC CCA GTA GCT GAG CGT CCT GAA GAT CGC TCT GAT GCA GAG CCT GAA AAC CAT GTG GTT GTG TCC TAT TGT CCA CCC ATC ATT AGT GAA GAA  3049
 925 Ile Ile Ser Pro Val Ala Glu Arg Pro Glu Asp Arg Ser Asp Ala Glu Pro Glu Asn His Val Val Val Ser Tyr Cys Pro Pro Ile Ile Ser Glu Glu   957
                                                                                                                                  ↑

3050 ATA CCA AAC CCA GCC GCA GAT GAA GCT GGA GCA CAG GTT ATT TAC ATT GAT GTT CAG TCG ATG TAT CAG CCT CAA GCA AAA CCA GAA GAA GAA  3148
 958 Ile Pro Asn Pro Ala Ala Asp Glu Ala Gly Ala Gln Val Ile Tyr Ile Asp Val Gln Ser Met Tyr Gln Pro Gln Ala Lys Pro Glu Glu Glu   990

3149 CAA GAA AAT GAC CCT GTA GGA GGG GCA GGC TAT AAG CCA CAG ATG CAC CTC CCC ATT TCT AAT TCT ACT GTG GAA GAT ATA GCT GCA GAA GAG GAC TTA GAT 3247
 991 Gln Glu Asn Asp Pro Val Gly Gly Ala Gly Tyr Lys Pro Gln Met His Leu Pro Ile Ser Asn Ser Thr Val Glu Asp Ile Ala Ala Glu Asp Leu Asp  1023

3248 AAA ACT GCG GGT TAC AGA CCT CAG GCC AAT GTA AAT ACA TGG AAT TTA GTG TCT CCA GAC TCT CCT AGA TCC ATA GAC AGC AAC AGT GAG ATT GTC TCA  3346
1024 Lys Thr Ala Gly Tyr Arg Pro Gln Ala Asn Val Asn Thr Trp Asn Leu Val Ser Pro Asp Ser Pro Arg Ser Ile Asp Ser Asn Ser Glu Ile Val Ser  1056

3347 TTT GGA AGT CCA TGC TCC ATT AAT TCC CGA CAA TTT TTG ATT CCT AAA GAT GAA GAC TCT CCT AAA TCT AAT GGA GGA GGG TGG TCC TTT ACA AAC  3445
1057 Phe Gly Ser Pro Cys Ser Ile Asn Ser Arg Gln Phe Leu Ile Pro Pro Lys Asp Glu Asp Ser Pro Lys Ser Asn Gly Gly Gly Trp Ser Phe Thr Asn 1089

3446 TTT TTT CAG AAC AAA CCA AAC GAT TAA  CAGTGTCACCGTCGTCTCACTCAGTCAGCCATCTCAGCCATTCAGCCATCTCAATAAGTCTTCTACTCTGTCTAGTCTTCCTACATCAGCACTGCTGGGCATTCTTGGAGGATCCTCTAG 3567
1090 Phe Phe Gln Asn Lys Pro Asn Asp End

3568 AGTATTGTTAGGAGGTGAACTTCA
```

FIGURE 2e

ANTIBODIES IMMUNOREACTIVE WITH LEUKEMIA INHIBITORY FACTOR RECEPTORS

CROSS-REFERENCE TO RELATED APPLICATION

This application is a divisional of U.S. application Ser. No. 08/119,780, filed Sep. 10, 1993, now U.S. Pat. No. 5,420,247, which is a divisional of U.S. application Ser. No. 07/943,843, filed Sep. 11, 1992, now U.S. Pat. No. 5,284, 755, which is a continuation-in-part of U.S. application Ser. No. 07/670,608, filed Mar. 13, 1991, now abandoned, which is a continuation-in-part of U.S. application Ser. No. 07/626, 725, filed Dec. 13, 1990, now abandoned.

BACKGROUND OF THE INVENTION

The present invention relates generally to cytokine receptors, and more specifically, to leukemia inhibitory factor receptors.

Leukemia inhibitory factor (LIF) is a polypeptide hormone which plays a central role in the regulation of diverse adult and embryonic systems. LIF acts on a variety of cell types and has multiple biological activities. The diversity of biological activity is reflected in the various synonyms of LIF, which include hepatocyte stimulating factor III (HSF III); Baumann and Wong, *J. Immunol.* 143:1163, 1989); cholinergic nerve differentiation factor (CNDF; Yamamori et al., *Science* 246:1412, 1990); melanoma-derived lipoprotein lipase inhibitor (MLPLI; Mori et al., *Biochem. Biophys Res. Comm.* 160:1085, 1989); human interleukin for DA cells (HILDA; Moreau et al., *Nature* 336:690, 1988); differentiation factor (D-factor, Tomida et al., *J. Biol. Chem.* 259:10978, 1984); differentiation inhibitory factor (DIF; Abe et al., *J. Biol. Chem.* 264:8941, 1989); differentiation inhibitory activity (DIA; Smith and Hooper, *Devel. Biol.* 121:1, 1987); and differentiation retarding factor (DRF; Koopman and Cotton, *Exp. Cell. Res.* 154:233, 1984).

The diversity of biological activities ascribed to LIF, whether differentiation inhibition or stimulation, proliferation or functional activation, is mediated by specific plasma membrane receptors which bind LIF. Despite the wide range of biological activities mediated by LIF, it is believed that LIF receptors (LIF-R) are highly conserved in a variety of species and expressed on a large variety of cells, since the ligand is highly conserved between species (Gough et al., *Proc. Natl. Acad. Sci. USA* 85:2623, 1988; Yamamori et al., *Science* 246:1412, 1990). LIF receptors have been identified by ligand affinity cross-linking techniques on various cell lines, including monocyte-macrophages (Hilton, et al., *Proc. Natl. Acad. Sci. USA* 85:5971, 1988), and also on some non-hematopoietic cells including osteoblasts, placental trophoblasts, and liver parenchymal cells (Metcalf et al., *Blood* 76:50, 1990). Such studies indicate that LIF-R has a molecular weight of 90 kDa (Jacques et al., 5th Symposium sur les Marqueurs de l'inflammation, Lyon 25–27 September 1990, Abstract No. 37, page 122 (bioMerieux sa, Lyon, France). Characterization of LIF receptors by Scatchard analysis of binding isotherms has demonstrated that specific cell surface receptor molecules from a variety of target cells have approximately the same affinity for LIF (40–100 pM) and are present in low numbers (150 to 2,500 receptors per cell) on all cells types tested.

In order to study the structural and biological characteristics of LIF-R and the role played by LIF-R in the responses of various cell populations to LIF stimulation, or to use LIF-R effectively in therapy, diagnosis, or assay, homogeneous compositions are needed. Such compositions are theoretically available via purification of receptors expressed by cultured cells, or by cloning and expression of genes encoding the receptors. Prior to the present invention, however, several obstacles prevented these goals from being achieved.

First, although some cell lines have been identified which express LIF-R, such cell lines express LIF-R only in very low numbers (150 to 2,500 receptors/cell), which has impeded efforts to purify receptors in amounts sufficient for obtaining amino acid sequence information or generating monoclonal antibodies. The low numbers of receptors has also precluded any practical translation assay-based method of cloning.

Second, even if LIF-R protein compositions of sufficient purity could be obtained to permit N-terminal protein sequencing, the degeneracy of the genetic code may not permit one to define a suitable probe without considerable additional experimentation. Many iterative attempts may be required to define a probe having the requisite specificity to identify a hybridizing sequence in a cDNA library. Although direct expression cloning techniques avoid the need for repetitive screening using different probes of unknown specificity and have been useful in cloning other receptors (e.g., IL-1R), they have not been shown to be sufficiently sensitive to identify LIF-R clones from cDNA libraries derived from cells expressing low numbers of LIF-R.

Thus, efforts to purify the LIF-R or to clone or express genes encoding LIF-R have been impeded by lack of purified receptor or a suitable source of receptor mRNA.

SUMMARY OF THE INVENTION

The present invention provides purified leukemia inhibitory factor receptor (LIF-R) and isolated DNA sequences encoding LIF-R, e.g., human and murine LIF-R, and analogs thereof. Preferably, such isolated DNA sequences are selected from the group consisting of (a) DNA sequences comprising a nucleotide sequence derived from the coding region of a native LIF-R gene; (b) DNA sequences capable of hybridization to a DNA of (a) under moderately stringent conditions and which encode biologically active LIF-R; and (c) DNA sequences which are degenerate as a result of the genetic code to a DNA sequence defined in (a) or (b) and which encode biologically active LIF-R. Examples of the DNA sequences of (a) are cDNA clones comprising the coding region of the DNA sequence presented in SEQ ID NO:1 (human clone 65), SEQ ID NO:3 (murine clone 3), or SEQ ID NO:5 (composite full length human LIF-R sequence). Isolated DNA sequences of the present invention may comprise cDNA, PCR-amplified DNA, genomic DNA lacking introns, chemically synthesized DNA, or combinations thereof. The present invention also provides recombinant expression vectors comprising the DNA sequences defined above, recombinant LIF-R proteins produced using the recombinant expression vectors, and processes for producing the recombinant LIF-R proteins utilizing the expression vectors.

The present invention also provides substantially homogeneous preparations of LIF-R protein. LIF-R proteins have the sequence of amino acids shown, for example, in SEQ ID NO:2 and SEQ ID NO:6 (both human LIF-R) and SEQ ID NO:4 (murine LIF-R). Homodimeric forms of the LIF-R proteins are also provided.

The present invention also provides compositions for use in therapy, diagnosis, assay for LIF or LIF-R, or in raising antibodies to LIF-R, comprising effective quantities of the LIF-R proteins of the present invention.

BRIEF DESCRIPTION OF THE FIGURES

These and other aspects of the present invention will become evident upon reference to the following detailed description.

FIG. 2 presents a human LIF-R DNA sequence and the amino acid sequence encoded thereby, derived by sequencing cDNA and genomic clones as described in example 4. Amino acids are numbered on the left and nucleotides on the right. The signal peptide includes amino acids −44 to −1. The transmembrane domain is heavily underlined, and potential N-linked glycosylation sites are marked with asterisks. Hallmark residues associated with the hematopoietin family of receptors are shown boxed. The horizontal arrow marks the point at which genomic sequence was used to derive the 3' coding region of the hLIF-R. All cDNA clones terminated with a stretch of A nucleotides at this point.

DETAILED DESCRIPTION OF THE INVENTION

Definitions

Figure 1:
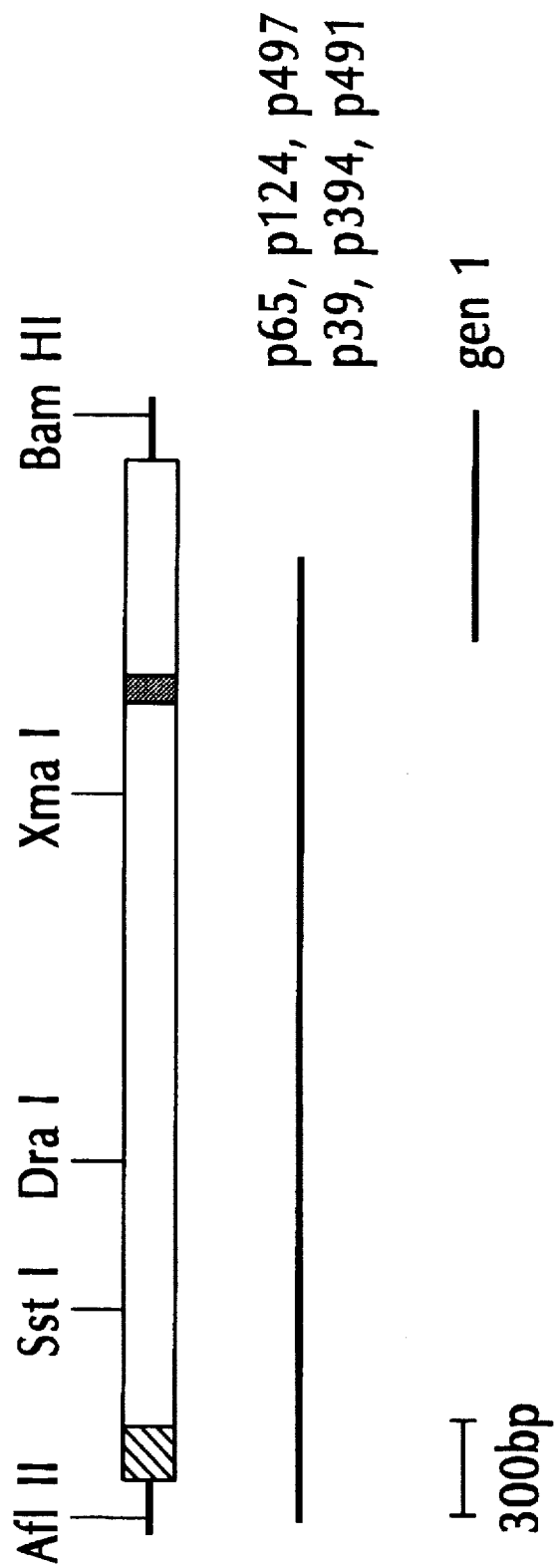
FIG. 1 presents a composite map of a human LIF-R-encoding DNA sequence, including the cleavage sites for certain restriction endonucleases. The hLIF-R open reading frame is shown boxed. The signal sequence is shown as a hatched box and the transmembrane domain is shown as a solid box. Several hLIF-R clones were isolated from cDNA and genomic libraries as described in examples 1 and 4. The horizontal lines under the composite map indicate the portion of the hLIF-R sequence that is contained in the various clones.

"Leukemia inhibitory factor receptor" and "LIF-R" refer to proteins which are present on the surface of various hematopoietic cells including monocyte-macrophages and megakaryocytes, and on non-hematopoietic cells, including osteoblasts, placental trophoblasts, and liver parenchyrnal cells, and which are capable of binding leukemia inhibitory factor (LIF) molecules and, in their native configuration as mammalian plasma membrane proteins, play a role in transducing the signal provided by LIF to a cell. The mature full-length human LIF-R has been previously described as a protein having a molecular weight of approximately 90 kDa; however, the molecular weight of the human LIF-R protein disclosed herein, and shown in SEQ ID NO:2, is about 190,000 kDa. As used herein, the above terms include analogs or fragments of native LIF-R proteins with LIF-binding or signal transducing activity. Specifically included are truncated, soluble or fusion forms of LIF-R protein as defined below. In the absence of any species designation, LIF-R refers generically to mammalian LIF-R, which includes, but is not limited to, human, murine, and bovine LIF-R. Similarly, in the absence of any specific designation for deletion mutants, the term LIF-R means all forms of LIF-R, including mutants and analogs which possess LIF-R biological activity.

"Soluble LIF-R" or "sLIF-R" as used in the context of the present invention refer to proteins, or substantially equivalent analogs, which are substantially similar to all or part of the extracellular region of a native LIF-R, and are secreted by the cell but retain the ability to bind LIF or inhibit LIF signal transduction activity via cell surface bound LIF-R proteins. Soluble LIF-R proteins may also include part of the transmembrane region or part of the cytoplasmic domain or other sequences, provided that the soluble LIF-R protein is capable of being secreted from the cell. Inhibition of LIF signal transduction activity can be determined using primary cells or cells lines which express an endogenous LIF-R and which are biologically responsive to LIF or which, when transfected with recombinant LIF-R DNAs, are biologically responsive to LIF. The cells are then contacted with LIF and the resulting metabolic effects examined. If an effect results which is attributable to the action of the ligand, then the recombinant receptor has signal transduction activity. Exemplary procedures for determining whether a polypeptide has signal transduction activity are disclosed by Idzerda et al., *J. Exp. Med.* 171:861 (1990); Curtis et al., *Proc. Natl. Acad. Sci. USA* 86:3045 (1989); Prywes et al., *EMBO J.* 5:2179 (1986) and Chou et al., *J. Biol. Chem.* 262:1842 (1987).

The term "isolated" or "purified", as used in the context of this specification to define the purity of LIF-R protein or protein compositions, means that the protein or protein composition is substantially free of other proteins of natural or endogenous origin and contains less than about 1% by mass of protein contaminants residual of production processes. Such compositions, however, can contain other proteins added as stabilizers, carriers, excipients or co-therapeutics. LIF-R is purified to substantial homogeneity if it is detectable as a single protein band in a polyacrylamide gel by silver staining.

The term "substantially similar," when used to define either amino acid or nucleic acid sequences, means that a particular subject sequence, for example, a mutant sequence, varies from a reference sequence (e.g., a native sequence) by one or more substitutions, deletions, or additions, the net effect of which is to retain biological activity of the LIF-R protein as may be determined, for example, in LIF-R binding assays, such as is described in Example 1 below. In one embodiment of the invention, such a mutant amino acid sequence is at least 90% identical, preferably at least 95% identical, to the amino acid sequence of a native LIF-R protein (e.g., the native sequence presented in SEQ ID NOS: 2, 4 or 6). In other words, at least 90% of the amino acids of a native LIF-R sequence are present, and in the same order, in the mutant sequence. For fragments of LIF-R proteins (e.g., soluble LIF-R polypeptides), the term "at least 90% identical" refers to that portion of the reference native sequence that is found in the LIF-R fragment.

Computer programs are available for determining the percent identity between two DNA or amino acid sequences (e.g., between a mutant sequence and a native sequence). One example is the GAP computer program, version 6.0, described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981).

Alternatively, nucleic acid subunits and analogs are "substantially similar" to the specific native DNA sequences disclosed herein (e.g., the sequences of SEQ ID NOS: 1, 3, or 5) if the DNA sequence is capable of hybridization to a native LIF-R DNA sequence under moderately stringent conditions (50° C., 2×SSC) and encodes biologically active LIF-R protein; or the DNA sequence is degenerate as a result of the genetic code to one of the foregoing native or hybridizing DNA sequences and encodes a biologically active LIF-R protein. DNA sequences that hybridize to a native LIF-R DNA sequence under conditions of severe stringency, and which encode biologically active LIF-R, are also encompassed by the present invention. Moderate and severe stringency hybridization conditions are terms understood by the skilled artisan and have been described in, for example, Sambrook et al. Molecular *Cloning: A Laboratory Manual*, 2 ed. Vol. 1, pp. 1.101–104, Cold Spring Harbor Laboratory Press, (1989). LIF-R proteins encoded by the foregoing DNA sequences are provided by the present invention.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein essentially free of native endogenous substances and unaccompanied by associated native glycosylation. Protein expressed in most bacterial cultures, e.g., *E. coli*, will be free of glycan; protein expressed in yeast may have a glycosylation pattern different from that expressed in mammalian cells.

"Biologically active," as used throughout the specification as a characteristic of LIF-R, means either that a particular molecule shares sufficient amino acid sequence similarity with a native LIF-R protein to be capable of binding detectable quantities of LIF, preferably at least 0.01 nmoles LIF per nanomole LIF-R, or, in the alternative, shares sufficient amino acid sequence similarity to be capable of transmitting an LIF stimulus to a cell, for example, as a component of a hybrid receptor construct. More preferably, biologically active LIF-R within the scope of the present invention is capable of binding greater than 0.1 nanomoles LIF per nanomole receptor, and most preferably, greater than 0.5 nanomoles LIF per nanomole receptor.

"DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. However, it will be evident that genomic DNA containing the relevant sequences could also be used. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the proteins provided by this invention may be assembled from cDNA fragments and short oligonucleotide linkers, or from a series of oligonucleotides, to provide a synthetic gene which is capable of being expressed in a recombinant transcriptional unit "Recombinant expression vector" refers to a plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

"Recombinant microbial expression system" means a substantially homogeneous monoculture of suitable host microorganisms, for example, bacteria such as *E. coli* or yeast such as *S. cerevisiae*, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Isolation of DNA Encoding LIF-R

A human DNA sequence encoding human LIF-R was isolated from a cDNA library prepared using standard methods by reverse transcription of polyadenylated RNA isolated from human placental cells. Transfectants expressing biologically active LIF-R were initially identified using a modified slide autoradiographic technique, substantially as described by Gearing et al., *EMBO J.* 8:3667, 1989. Briefly, COS-7 cells were transfected with miniprep DNA in pDC303 from pools of cDNA clones directly on glass slides and cultured for 2–3 days to permit transient expression of LIF-R. The slides containing the transfected cells were then incubated with medium containing $^{125}$I-LIF, washed to remove unbound labeled LIF, fixed with glutaraldehyde, and dipped in liquid photographic emulsion and exposed in the dark. After developing the slides, they were individually examined with a microscope and positive cells expressing LIF-R were identified by the presence of autoradiographic silver grains against a light background.

Using this approach, approximately 240,000 cDNAs were screened in pools of approximately 2,400 cDNAs using the slide autoradiographic method until assay of one transfectant pool showed multiple cells clearly positive for LIF binding. This pool was then partitioned into pools of 600 and again screened by slide autoradiography and a positive pool was identified. This pool was further partitioned into pools of 60 and screened by plate binding assays analyzed by quantitation of bound $^{125}$I-LIF. The cells were scraped off and counted to determine which pool of 60 was positive. Individual colonies from this pool of 60 were screened until a single clone (clone 65) was identified which directed synthesis of a surface protein with detectable LIF binding activity. This clone was isolated, and its insert is sequenced to determine the sequence of the human LIF-R cDNA clone 65. The cloning vector pDC303 which contains the human LIF-R cDNA clone 65 was deposited with the American Type Culture Collection, Rockville, Md., USA (ATCC) on Dec. 11, 1990, under the name pHLIFR-65 (ATCC Accession No. 68491). The deposit was made under the conditions of the Budapest Treaty.

A probe may be constructed from the human sequence and used to screen various other mammalian cDNA libraries. cDNA clones which hybridize to the human probe are then isolated and sequenced.

A murine LIF-R cDNA clone was isolated by cross-species hybridization to a probe derived from human clone 65. The murine clone encoded a LIF-R protein that lacked a transmembrane region and thus was secreted rather than being retained on the cell membrane. Isolation of this murine clone is described in Example 2. Probes derived from this clone may be used in screening murine cDNA or genomic libraries to identify additional murine LIF-R clones.

A probe derived from the human clone 65 was also used in screening human cDNA and genomic libraries to identify additional human LIF-R clones. The DNA sequence presented in SEQ ID NO:5 was derived by sequencing and alignment of these human clones, as described in Example 4.

Like most mammalian genes, mammalian LIF-R is presumably encoded by multi-exon genes. Alternative mRNA constructs which can be attributed to different mRNA splicing events following transcription, and which share large regions of identity or similarity with the cDNAs claimed herein, are considered to be within the scope of the present invention.

Proteins and Analogs

The present invention provides purified mammalian LIF-R polypeptides, both recombinant and non-recombinant (the latter being purified from naturally-occurring cellular sources). Isolated LIF-R polypeptides of this invention are substantially free of other contaminating materials of natural or endogenous origin and contain less than about 1% by mass of protein contaminants residual of production processes. The LIF-R polypeptides of this invention are optionally without associated native-pattern glycosylation.

Mammalian LIF-R of the present invention includes, by way of example, primate, human, murine, canine, feline, bovine, ovine, equine, caprine and porcine LIF-R. Mammalian LIF-R can be obtained by cross species hybridization, for example using a single stranded cDNA derived from the human LIF-R DNA sequence, clone 65, as a hybridization probe to isolate LIF-R cDNAs from mammalian cDNA libraries.

Derivatives of LIF-R within the scope of the invention also include various structural forms of the primary protein which retain biological activity. Due to the presence of ionizable amino and carboxyl groups, for example, a LIF-R protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to LIF-R amino acid side chains or at the N- or C-termini. Other derivatives of LIF-R within the scope of this invention include covalent or aggregative conjugates of LIF-R or its fragments with other proteins or polypeptides, such as by synthesis in recombinant culture as N-terminal or C-termninal fusions. For example, the conjugated peptide may be a a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader). LIF-R protein fusions can comprise peptides added to facilitate purification or identification of LIF-R (e.g., poly-His). The amino acid sequence of LIF-R can also be linked to the peptide Asp-Tyr-Lys-Asp-Asp-Asp-Asp-Lys (DYKDDDDK) (Hopp et al., Bio/Technology 6:1204,1988 and U.S. Pat. No. 5,011, 912.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue imndately following the Asp-Lys pairing. Fusion proteins capped with this peptide may also be resistant to intracellular degradation in E. coli.

LIF-R derivatives may also be used as immunogens, reagents in receptor-based immunoassays, or as binding agents for affinity purification procedures of LIF or other binding ligands. LIF-R derivatives may also be obtained by cross-linking agents, such as M-maleirnidobenzoyl succinimide ester and N-hydroxysuccinimide, at cysteine and lysine residues. LIF-R proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, LIF-R may be used to selectively bind (for purposes of assay or purification) anti-LIF-R antibodies or LIF.

The LIF-R proteins of the present invention encompass proteins having amino acid sequences that vary from those of native LIF-R proteins, but that retain the ability to bind LIF or transduce a LIF-induced signal. Such variant proteins comprise one or more additions, deletions, or substitutions of amino acids when compared to a native sequence, but exhibit biological activity that is essentially equivalent to that of a native LIF-R protein. Likewise, the LIF-R-encoding DNA sequences of the present invention encompass sequences that comprise one or more additions, deletions, or substitutions of nucleotides when compared to a native LIF-R DNA sequence, but that encode a LIF-R protein that is essentially bioequivalent to a native LIF-R protein. Examples of such variant amino acid and DNA sequences (the "substantially similar" sequences discussed above) include, but are not limited to, the following.

Figure 2A:
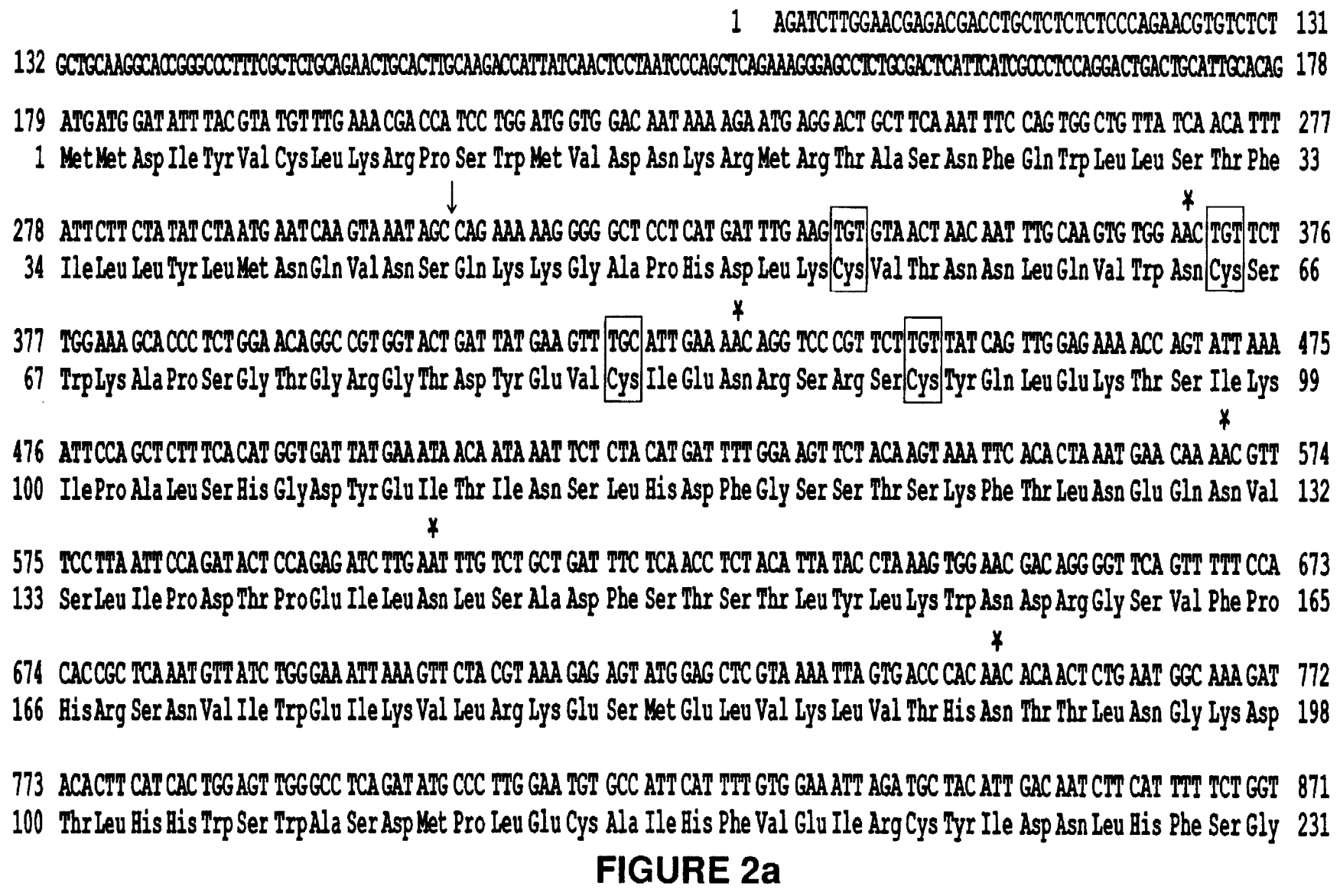

Bioequivalent analogs of LIF-R proteins may be constructed by, for example, making various substitutions of residues or sequences or deleting terminal or internal residues or sequences not needed for biological activity. Bioequivalent analogs may be identified using the assays for biological activity that are described herein (e.g., in example 1). For example, cysteine residues not essential for biological activity can be deleted or replaced with other amino acids to prevent formation of unnecessary or incorrect intrarolecular disulfide bridges upon renaturation. One or more of the cysteines that are not conserved in the hematopoietin receptor family (as indicated in FIG. 2) may be deleted or replaced, for example. Alternative embodiments (when the LIF-binding property of the LIF-R is desired but signal transduction is not necessary) include LIF-Rs in which the cysteines of the extracellular domain remain but cysteines of the cytoplasmic domain are deleted or replaced.

Another embodiment of the present invention involves modification of adjacent dibasic amino acid residues to enhance expression of LIF-R in yeast systems in which KEX2 protease activity is present. Site-specific mutagenesis procedures can be employed to inactivate KEX2 protease processing sites by deleting, adding, or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. The resulting muteins are less susceptible to cleavage by the KEX2 protease at locations other than the yeast α-factor leader sequence, where cleavage upon secretion is intended. EP 212,914, is among the references disclosing the use of site-specific mutagenesis to inactivate KEX2 protease processing sites in a protein.

Review of the human LIF-R sequence of FIG. 2 reveals Arg-Arg, Arg-Lys, or Lys-Arg doublets at amino acids –36 and –35 ; –27 and –26; 134 and 135; 339 and 340; 631 and 632; 816 and 817; and 817 and 818. From one to all of these KEX2 protease processing sites may be inactivated.

The present invention includes LIF-R with or without associated native-pattern glycosylation. LIF-R expressed in yeast or mammalian expression systems, e.g., COS-7 cells, may be similar or slightly different in molecular weight and glycosylation pattern than the native molecules, depending upon the expression system. Expression of LIF-R DNAs in bacteria such as *E. coli* provides non-glycosylated molecules. Functional mutant analogs of mammalian LIF-R having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such sites can be eliminated by substituting another amino acid for Asn or for residue Z, deleting Asn or Z, or inserting a non-Z amino acid between $A_1$ and Z, or an amino acid other than Asn between Asn and $A_1$.

Known procedures for inactivating N-glycosylation sites in proteins include those described in U.S. Pat. No. 5,071,972 and EP 276,846. N-glycosylation sites in human LIF-R are indicated by asterisks in FIG. 2. From one to all of these sites may be inactivated. In one embodiment of the invention, if reduction but not elimination of glycosylation is desired, the first (i.e., N-terminal) five N-glycosylation sites of human LIF-R are inactivated. Review of the murine LIF-R amino acid sequence of SEQ ID NO:4 reveals that the murine protein lacks these five N-glycosylation sites (located in the first hematopoietin domain), indicating that these sites may be deleted from the human protein as well without eliminating the protein's LIF-binding property.

Generally, substitutions should be made conservatively; i.e., the most preferred substitute amino acids are those having physiochemical characteristics resembling those of the residue to be replaced. Similarly, when a deletion or insertion strategy is adopted, the potential effect of the deletion or insertion on biological activity should be considered. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Moreover, particular amino acid differences between human, murine and other mammalian LIF-Rs is suggestive of additional conservative substitutions that may be made without altering the essential biological characteristics of LIF-R.

Subunits (fragments) of LIF-R may be constructed by deleting terminal or internal residues or sequences. LIF-R fragments encompassed by the present invention include, but are not limited to, the following. Additional biologically active LIF-R fragments may be identified using assays such as those described in example 1. One example of an LIF-R fragment comprises amino acids 1 to 945 of SEQ ID NO:1. As described in example 4, amino acid 945 is the last amino acid of the polypeptide encoded by clone pHLIF-R-65, before the poly-A nucleotide segment believed to result from oligo(dT) prinming at an internal site in the mRNA during preparation of the hLIF-R cDNA.

LIF-binding activity resides in the extracellular domain. Thus, for applications requiring LIF-binding activity (but not the signal transducing activity conferred by the cytoplasmic domain), useful LIF-R proteins include those lacking all or part of the transmembrane region or the cytoplasmic domain of the protein. Human LIF-R fragments thus include those containing amino acids –44–x or, when the signal sequence is not desired, amino acids 1–x of the full length LIF-R sequence depicted in SEQ ID NO:5, wherein x represents an integer from 789 to 1052. Amino acid number 789 is the last amino acid of the extracellular domain (i.e., before the start of the transmembrane region). Polypeptides terminating in amino acid number 1052 lack the last C-terminal amino acid of the full length protein. The desirability of including the signal sequence depends on such factors as the position of LIF-R when it is a component of a fusion protein, and the intended host cells when the receptor is to be produced via recombinant DNA technology. Other LIF-R polypeptides may be chosen with regard to sequences that are conserved in the hematopoietin receptor family, (i.e., chosen to include the boxed sequence(s) shown in FIG. 2).

In one embodiment of the present invention, the LIF-R fragment is a soluble LIF-R polypeptide in which the transmembrane region and intracellular (cytoplasmic) domain of LIF-R are deleted or substituted with hydrophilic residues to facilitate secretion of the receptor into the cell culture medium. Soluble LIF-R proteins may also include part of the transmembrane region, provided that the soluble LIF-R protein is capable of being secreted from the cell. The resulting protein is referred to as a soluble LIF-R molecule which retains its ability to bind LIF. The present invention contemplates such soluble LIF-R constructs corresponding to all or part of the extracellular region of LIF-R. The resulting soluble LIF-R constructs are then inserted and expressed in appropriate expression vectors and assayed for the ability to bind LWF, as described in Example 1. Biologically active soluble LIF-Rs resulting from such constructions are also contemplated to be within the scope of the present invention.

Examples of soluble LIF-R proteins include, but are not limited to, the following. One soluble human LIF-R polypeptide comprises the entire extracellular domain, i.e. amino acids 1–789 of SEQ ID NO:2. Other soluble LIF-Rs are truncated upstream of the transmembrane region, but preferably include that portion of the protein that contains the residues conserved among the members of the hematopoietin receptor family (shown boxed in FIG. 2), i.e., amino acids 11–479 of SEQ ID NO:2. The N-terminus of such soluble LIF-Rs is any of amino acids 1–11, and the protein extends to a C-terminus selected from any of amino acids 479 through 789. Two such soluble proteins comprise amino acids 1–702 or 1–775 of SEQ ID NO:1. Constructs encoding these proteins may be prepared by techniques that involve cleaving the human LIF-R cDNA of clone 65 (example 1) with the restriction endonucleases Asp718 and Xmn1 or with Asp718 and Bsp1286I. Asp718 cleaves the vector upstream of the inserted LIF-R-encoding cDNA. Xmn1 cleaves within the codon for Asp at position 702 and Bsp1286I cleaves just 3' of the codon for Val at position 775. If desired, an oligonucleotide may be ligated to the 3' end of the Asp718/Bsp1286I fragment to extend the LIF-R sequence, e.g., through amino acid number 789.

Other soluble human LIF-Rs comprise amino acids 1–678 or 1–680. When the human and murine LIF-R amino acid sequences disclosed herein are aligned (with gaps introduced to maximize identity between the two sequences), amino acid 680 of the human sequence is aligned with the last amino acid of the murine protein, and amino acid 678 is the last amino acid of the human sequence that is identical to a corresponding amino acid in the murine sequence. Since the murine protein binds LIF, the murine LIF-R contains that portion of the protein required for LIF binding.

The murine cDNA isolated in example 2 encodes a naturally occurring soluble LIF-R protein. DNA sequences encoding soluble human LIF-R proteins may be derived from the isolated cDNA encoding membrane-bound human LIF-R (described in example 1) by conventional procedures, in view of the sequence information presented in SEQ ID NO:1. Among the procedures that may be employed to isolate and amplify a DNA fragment encoding truncated LIF-R is the well known polymerase chain reaction (PCR) procedure. See *Recombinant DNA Methodology*, Wu et al. eds., Academic Press Inc., San Diego (1989), pp 189–196. Alternative procedures include restriction endonuclease digestion of cloned LIF-R DNA, isolation of the desired fragment by gel electrophoresis, and subcloning of the fragment into an expression vector using conventional procedures. Oligonucleotides may be ligated to an isolated DNA fragment to regenerate the 5' or 3' terminus to a desired point in the sequence. The sequence of such oligonucleotides, as well as the primers employed in PCR, may be based upon the DNA sequence presented in SEQ ID NO:1.

The N- or C-terminus of the LIF-R proteins of the present invention may vary according to such factors as the type of host cells employed when producing the protein via recombinant DNA technology and the particular cells from which the protein is purified when non-recombinant LIF-R is employed. Such variations may be attributable to differential post translational processing of the protein in various types of cells, for example. Variations in the N-or C-terminal sequence also may result from the oligonucleotides chosen to reconstruct either terminus of the LIF-R encoding DNA sequence when constructing expression vectors.

Differential processing may result in mature LIF-R proteins having an N-terminal amino acid other than those shown at position 1 of SEQ ID NOS:2, 4, and 6. For example, in certain host cells, post-translational processing will remove the methionine residue encoded by an initiation codon, whereas the methionine residue will remain at the N-terminus of proteins produced in other types of host cells. Further, the N- and C-termini have been known to vary for the same protein, depending on the source of the protein. In some cases, the deletion of amino acids at either terminus of the protein may be due to proteolysis, occurring either intracellularly or during purification. Varying N-termini may also result from cleavage of the signal peptide in certain host cells at a point other than between amino acids −1 and 1 of the disclosed sequences.

The LIF-R proteins of the present invention thus include proteins having termini that vary from those shown in SEQ ID NOS:2 and 6 (human) or 4 (murine). The N-terminal amino acid of the mature protein may, for example, be any of the amino acids at positions 1 to 5 of SEQ ID NOS:2, 4, or 6. The C-terminus may be truncated deliberately during expression vector construction (e.g., in constructing vectors encoding soluble proteins as described above) or as a result of differential processing which may remove up to about five C-terminal amino acids, for example.

Mutations in nucleotide sequences constructed for expression of the above-described variant or analog LIF-R proteins should, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predeterined For example, in order to select for optimum characteristics of mutants at a given site, random mutagenesis may be conducted at the target codon and the expressed LIF-R mutants screened for the desired activity.

Not all mutations in the nucleotide sequence which encodes LIF-R will be expressed in the final product. For example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression (see U.S. Pat. No. 4,425,437, column 6). The known degeneracy of the genetic code permits variation of a DNA sequence without altering the amino acid sequence, since a given amino acid may be encoded by more than one codon.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of maling the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

The LIF-R proteins of the present invention encompass proteins encoded by (a) a DNA sequence derived from the coding region of a native LIF-R gene or (b) a DNA sequence capable of hybridization to a native LIF-R DNA of (a) under moderately stringent conditions and which encodes biologically active LIF-R. LIF-R proteins encoded by a DNA molecule that varies from the DNA sequences of SEQ ID NOS: 1, 3, and 5, wherein one strand of the DNA molecule will hybridize to the DNA sequence presented in SEQ ID NOS: 1, 3, or 5, include, but are not limited to, LIF-R fragments (soluble or membrane-bound) and LIF-R proteins comprising inactivated N-glycosylation site(s), inactivated KEX2 protease processing site(s), and/or conservative amino acid substitution(s), as described above. LIF-R proteins encoded by DNA derived from other mammalian species, wherein the DNA will hybridize to the human or murine DNA of SEQ ID NOS: 1, 3, or 5, are also encompassed.

Both monovalent forms and polyvalent forms of LIF-R are useful in the compositions and methods of this invention. Polyvalent forms possess multiple LIF-R binding sites for LIF ligand. For example, a bivalent soluble LIF-R may consist of two tandem repeats of the extracellular region of LIF-R, separated by a linker region. Two LIF-R polypeptides (each capable of binding LIF) may be joined via any suitable means, e.g., using one of the commercially available cross-linking reagents used to attach one polypeptide to another (Pierce Chemical Co., Rockford, Ill.). Alternatively, a fusion protein comprising multiple LIF-R polypeptides joined via peptide linkers may be produced using recombinant DNA technology. Suitable peptide linkers comprise a chain of amino acids, preferably from 20 to 100 amino acids in length. The linker advantageously comprises amino acids selected from the group consisting of glycine, asparagine, serine, threonine, and alanine. Examples of suitable peptide linkers include, but are not limited to, (Gly$_4$Ser)n, wherein n is 4–12, and (Gly$_4$SeiGly$_5$Ser)$_2$. The use of such peptide linkers is illustrated in U.S. Pat. No. 5,073,627, for example.

A DNA sequence encoding a desired peptide linker may be inserted between, and in the same reading frame as, two DNA sequences encoding LIF-R using any suitable conventional technique. For example, a chemically synthesized oligonucleotide encoding the linker and containing appropriate restriction endonuclease cleavage sites may be ligated between two LIF-R encoding sequences. The resulting gene fusion is inserted into an expression vector for production of the fusion protein in the desired host cells.

Alternate polyvalent forms may also be constructed, for example, by chemically coupling LIF-R to any clinically acceptable carrier molecule, a polymer selected from the group consisting of Ficoll, polyethylene glycol or dextran using conventional coupling techniques. Alternatively, LIF-R may be chemically coupled to biotin, and the biotin-LIF-R conjugate then allowed to bind to avidin, resulting in tetravalent avidin/biotin/LIF-R molecules. LIF-R may also be covalently coupled to dinitrophenol (DNP) or trinitrophenol (TNP) and the resulting conjugate precipitated with anti-DNP or anti-TNP-IgM, to form decameric conjugates with a valency of 10 for LIF-R binding sites.

A recombinant chimeric antibody molecule may also be produced having LIF-R sequences substituted for the variable domains of either or both of the immunoglobulin molecule heavy and light chains and having unmodified constant region domains. For example, chimeric LIF-R/IgG$_1$ may be produced from two chimeric genes—a LIF-R/human k light chain chimera (LIF-R/C$_k$) and a LIF-R/human g1 heavy chain chimera (LIF-R/C$_{g-1}$). Following transcription and translation of the two chimeric genes, the gene products assemble into a single chimeric antibody molecule having LIF-R displayed bivalently. Assembly of two sets of the two chimeric proteins results in a molecule comprising two LIF-R/light chain fusions and two LIF-R/heavy chain fusions. LIF-R is displayed tetravalently. Assembly occurs when disulfide bonds form between the polypeptide chains, as occurs in native antibodies. Such polyvalent forms of LIF-R may have enhanced binding affinity for LIF ligand. Additional details relating to the construction of such chimeric antibody molecules are disclosed in WO 89/09622 and EP 315062.

Alternatively, a LIF-R DNA sequence may be fused to a DNA sequence encoding an ntibody Fc region polypeptide. Dimeric forms of LIF-R include homodimers comprising two IF-R/Fc fusion proteins joined by disulfide bonds between the Fc moieties. Such homodimers preferably comprise one of the soluble LIF-R polypeptides described above, with an antibody Fc region polypeptide attached to the C-terminus of the LIF-R polypeptide. The LIF-R/Fc fusion proteins optionally comprise a peptide linker (described above) positioned between the LIF-R polypeptide and the antibody Fc polypeptide. One peptide linker is described in example 5.

By "antibody Fc region polypeptides" is meant polypeptides corresponding to the Fc region of an antibody, or fragments thereof comprising sufficient cysteine residues so that disulfide bonds will form between two Fc polypeptides. N-terminal fragments of an antibody Fc region that contain the cysteine residues involved in disulfide bond formation at the hinge region may be employed. Examples include the Fc polypeptide described in example 5 and fragments thereof comprising at least the first three cysteine residues (hinge region). Procedures for isolating the Fc region of an antibody are well-known and include proteolytic digestion with papain. Alternatively, an Fc polypeptide may be produced by recombinant cells or chemically synthesized.

In one embodiment, the present invention provides an isolated DNA sequence encoding a soluble fusion protein comprising an N-terminal signal peptide followed by a human LIF-R polypeptide (derived from the extracellular domain), which is followed by an antibody Fc polypeptide. The signal sequence may be the native human LIF-R signal peptide (amino acids –44 to –1 of SEQ ID NO: 1) or a heterologous signal peptide, chosen according to the host cells to be employed. Heterologous signal peptides include the yeast a factor leader peptide described below and the IL-7 leader peptide described in U.S. Pat. No. 4,965,195, for example.

Figure 3:
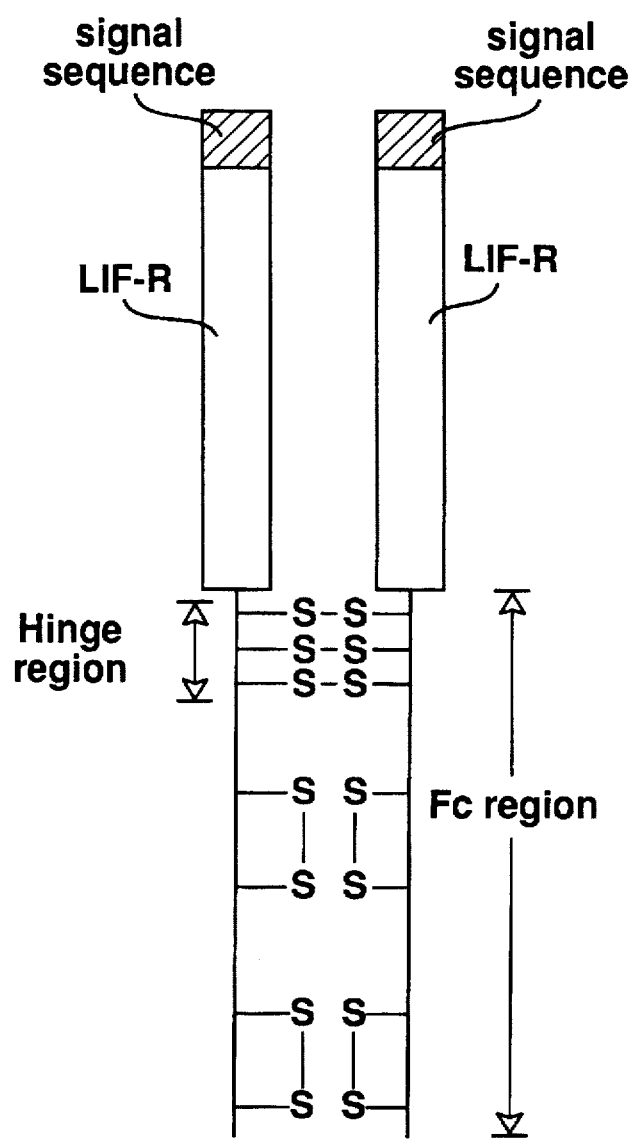
FIG. 3 is a schematic representation of a human LIF-R homodimer. The homodimeric receptor comprises two soluble human LIF-R/Fc fusion proteins joined by disulfide bonds between the Fc moieties.

One example of a dimeric receptor comprising two LIF-R/Fc polypeptides is illustrated in example 5 below. The receptor is depicted in FIG. 3. The number and position of disulfide bonds may vary from those shown in FIG. 3.

Expression of Recombinant LIF-R

The present invention provides recombinant expression vectors to amplify or express DNA encoding LIF-R. Recombinant expression vectors are replicable DNA constructs which have synthetic or cDNA-derived DNA fragments encoding mammalian LIF-R or bioequivalent analogs operably linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements may include an operator sequence to control transcription, a sequence encoding suitable mRNA ribosomal binding sites. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

DNA sequences encoding mammalian LIF-Rs which are to be expressed in a microorganism will preferably contain no introns that could prematurely terminate transcription of DNA into mRNA; however, premature termination of transcription may be desirable, for example, where it would result in mutants having advantageous C-terminal truncations, for example, deletion of a transmembrane region to yield a soluble receptor not bound to the cell membrane. Due to code degeneracy, there can be considerable variation in nucleotide sequences encoding the same amino acid sequence. Other embodiments include sequences capable of hybridizing to clone 65 under moderately stringent conditions (50° C., 2× SSC) and other sequences hybridizing or degenerate to those which encode biologically active LIF-R polypeptides.

Recombinant LIF-R DNA is expressed or amplified in a recombinant expression system comprising a substantially homogeneous monoculture of suitable host microorganisms, for example, bacteria such as *E. coli* or yeast such as *S. cerevisiae*, which have stably integrated (by transformation or transfection) a recombinant transcriptional unit into chromosomal DNA or carry the recombinant transcriptional unit as a component of a resident plasmid. Mammalian host cells are preferred for expressing recombinant LIF-R. Generally, cells constituting the system are the progeny of a single ancestral transformant. Recombinant expression systems as defined herein will express heterologous protein upon induction of the regulatory elements linked to the DNA sequence or synthetic gene to be expressed.

Transformed host cells are cells which have been transformed or transfected with LIF-R vectors constructed using recombinant DNA techniques. Transformed host cells ordinarily express LIF-R, but host cells transformed for purposes of cloning or amplifying LIF-R DNA do not need to express LIF-R. Expressed LIF-R will be deposited in the cell membrane or secreted into the culture supernatant, depending on the LIF-R DNA selected. Suitable host cells for expression of mammalian LIF-R include prokaryotes, yeast or higher eukaryotic cells under the control of appropriate promoters. Prokaryotes include gram negative or gram positive organisms, for example *E. coli* or *bacilli*. Higher eukaryotic cells include established cell lines of mammalian origin as described below. Cell-free translation systems could also be employed to produce mammalian LIF-R using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, N.Y. 1985), the relevant disclosure of which is hereby incorporated by reference.

Prokaryotic expression hosts may be used for expression of LIF-R that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphylococcus, although others may also be employed as a matter of choice.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 and pGEX (Pharmacia Fine Chemicals, Uppsala, Sweden) and pGEM1 (Promega Biotec, Madison, Wis. USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the b-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, Molecular *Cloning: A Laboratory Manual*, Cold Spring Harbor Laboratory, p. 412, 1982). A particularly useful bacterial expression system employs the phage 1 $P_L$ promoter and cI857ts thermolabile repressor. Plasmid vectors available from the American Type Culture Collection which incorporate derivatives of the 1 $P_L$ promoter include plasmid pHUB2, resident in *E. coli* stain JMB9 (ATCC 37092) and pPLc28, resident in *E. coli* RR1 (ATCC 53082).

Recombinant LIF-R proteins may also be expressed in yeast hosts, preferably from the Saccharomyces species, such as *S. cerevisiae*. Yeast of other genera, such as Pichia or Kluyveromyces may also be employed. Yeast vectors will generally contain an origin of replication from the 2 m yeast plasmid or an autonomously replicating sequence (ARS), promoter, DNA encoding LIF-R, sequences for polyadenylation and transcription termination and a selection gene. Preferably, yeast vectors will include an origin of replication and selectable marker permitting transformation of both yeast and *E. col.* e.g., the ampicillin resistance gene of *E. coli* and *S. cerevisiae* TRP1 or URA3 gene, which provides a selection marker for a mutant strain of yeast lacking the ability to grow in tryptophan, and a promoter derived from a highly expressed yeast gene to induce transcription of a structural sequence downstream. The presence of the TRP1 or URA3 lesion in the yeast host cell genome then provides an effective environment for detecting transformation by growth in the absence of tryptophan or uracil.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pUC18 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kuian et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. USA* 75:1929, 1978, selecting for Trp+ transformants in a selective medium consisting of 0.67% yeast nitrogen base, 0.5% casamino acids, 2% glucose, 10 µg/ml adenine and 20 µg/ml uracil or URA+ transformants in medium consisting of 0.67% YNB, with amino acids and bases as described by Sherman et al., *Laboratory Course Manual for Methods in Yeast Genetics*, Cold Spring Harbor Laboratory, Cold Spring Harbor, N.Y., 1986.

Host strains transformed by vectors comprising the ADH2 promoter may be grown for expression in a rich medium consisting of 1% yeast extract, 2% peptone, and 1% or 4% glucose supplemented with 80 µg/ml adenine and 80 µg/ml uracil. Derepression of the ADH2 promoter occurs upon exhaustion of medium glucose. Crude yeast supernatants are harvested by filtration and held at 4° C. prior to further purification.

Various mammalian or insect cell culture systems are also advantageously employed to express recombinant protein. Expression of recombinant proteins in mammalian cells is particularly preferred because such proteins are generally correctly folded, appropriately modified and completely functional. Examples of suitable mammalian host cell lines include the COS-7 lines of monkey kidney cells, described by Gluzman (*Cell* 23:175, 1981), and other cell lines capable of expressing a heterologous gene in an appropriate vector including, for example, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *Bio/Technology* 6:47 (1988).

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the HindIII site toward the BglI site located in the viral origin of replication is included. Further, mammalian genomic LIF-R promoter, control and/or signal sequences may be utilized, provided such control sequences are compatible with the host cell chosen. Additional details regarding the use of a mammalian high expression vector to produce a recombinant mammalian LIF-R are provided in Example 1 below. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

In preferred aspects of the present invention, recombinant expression vectors comprising LIF-R cDNAs are stably integrated into a host cell's DNA. Elevated levels of expression product is achieved by selecting for cell lines having amplified numbers of vector DNA. Cell lines having amplified numbers of vector DNA are selected, for example, by transforming a host cell with a vector comprising a DNA sequence which encodes an enzyme which is inhibited by a known drug. The vector may also comprise a DNA sequence which encodes a desired protein. Alternatively, the host cell may be co-tansformed with a second vector which comprises the DNA sequence which encodes the desired protein. The transformed or co-transformed host cells are then cultured in increasing concentrations of the known drug, thereby selecting for drug-resistant cells. Such drug-resistant cells survive in increased concentrations of the toxic drug by over-production of the enzyme which is inhibited by the drug, frequently as a result of amplification of the gene encoding the enzyme. Where drug resistance is caused by an increase in the copy number of the vector DNA encoding the inhibitable enzyme, there is a concomitant coamplification of the vector DNA encoding the desired protein (e.g., LIF-R) in the host cell's DNA.

A preferred system for such co-amplification uses the gene for dihydrofolate reductase (DHFR), which can be inhibited by the drug methotrexate (OTX). To achieve co-amplification, a host cell which lacks an active gene encoding DHFR is either transformed with a vector which comprises DNA sequence encoding DHFR and a desired protein, or is co-transformed with a vector comprising a DNA sequence encoding DHFR and a vector comprising a DNA sequence encoding the desired protein. The transformed or co-transformed host cells are cultured in media containing increasing levels of MTX, and those cells lines which survive are selected.

A particularly preferred co-amplification system uses the gene for glutamine synthetase (GS), which is responsible for the synthesis of glutamine from glutamate and ammonia using the hydrolysis of ATP to ADP and phosphate to drive the reaction. GS is subject to inhibition by a variety of inhibitors, for example methionine sulphoximine (MSX). Thus, LIF-R can be expressed in high concentrations by co-amplifying cells transformed with a vector comprising the DNA sequence for GS and a desired protein, or co-transformed with a vector comprising a DNA sequence encoding GS and a vector comprising a DNA sequence encoding the desired protein, culturing the host cells in media containing increasing levels of MSX and selecting for surviving cells. The GS co-amplification system, appropriate recombinant expression vectors and cells lines, are described in the following PCT applications: WO 87/04462, WO 89/01036, WO 89/10404 and WO 86/05807.

Recombinant proteins are preferably expressed by co-amplification of DHFR or GS in a mammalian host cell, such as Chinese Hamster Ovary (CHO) cells, or alternatively in a murine myeloma cell line, such as SP2/0-Ag14 or NS0 or a rat myeloma cell line, such as YB2/3.0-Ag20, disclosed in PCT applications WO/89/10404 and WO 86/05807.

Vectors derived from retroviruses may be employed in mammalian host cells. A preferred retroviral expression vector is tgLS(+) HyTK, described in PCT application WO 92/08796.

A preferred eukaryotic vector for expression of LIF-R DNA is disclosed below in Example 1. This vector, referred to as pDC303, was derived from the mammalian high expression vector pDC201 and contains regulatory sequences from SV40, CMV and adenovirus.

In an especially preferred expression system, a LIF-R-encoding DNA sequence is inserted into the mammalian expression vector pCAV-DBYR. The resulting recombinant expression vector is transfected into a DHFR- Chinese hamster ovary cell line, e.g., CHO-DXB11. pCAV-DHFR is an expression vector containing SV40 promoter sequences upstream of a multiple cloning site and a dihydrofolate reductase (DHFR) gene as a selectable marker. The DHFR gene confers a selective advantage on otherwise DHFR-mammalian cells that have taken up the vector, when grown in the presence of mnethotrexate (MTX).

pCAV/DHFR was prepared by inserting a DHFR gene into the plasmid vector known as pCAV/NOT (described in PCT application WO 90/05183). pCAV/NOT was assembled from pDC201 (a derivative of pMLSV, previously described by Cosman et al., Nature 312:768, 1984), SV40 and cytomegalovirus DNA and comprises, in sequence with the direction of transcription from the origin of replication: (1) SV40 sequences from coordinates 5171-270 including the origin of replication, enhancer sequences and early and late promoters; (2) cytomegalovirus sequences including the promoter and enhancer regions (nucleotides 671 to+63 from the sequence published by Boechart et al. (Cell 41:521, 1985); (3) adenovirus-2 sequences containing the first exon and part of the intron between the first and second exons of the tripartite leader, the second exon and part of the third exon of the tripartite leader and a multiple cloning site (MCS) containing sites for Xho1, Kpn1, Sma1, Not1 and Bgl1; (4) SV40 sequences from coordinates 4127–4100 and 2770–2533 that include the polyadenylation and termination signals for early transcription; (5) sequences derived from pBR322 and virus-associated sequences VAI and VAII of pDC201, with adenovirus sequences 10532-11156 containing the VAI and VAII genes, followed by pBR322 sequences from 4363-2486 and 1094-375 containing the ampicillin resistance gene and origin of replication.

Purification of Recombinant LIF-R

Purified recombinant mammalian LIF-Rs or analogs are prepared by culturing suitable host/vector systems to express the recombinant translation products of the DNAs of the present invention, which are then purified from culture media or cell extracts.

For example, supernatants from systems which secrete recombinant soluble LIF-R protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise an LIF or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-BPLC media, e.g., silica gel having pendant methyl or other aliphatic groups, can be employed to further purify a LIF-R composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian LIF-R can be disrupted by any convenient method, including freeze-thaw cycling, sonication, mechanical disruption, or use of cell lysing agents.

Fermentation of yeast which express soluble mammalian LIF-R as a secreted protein greatly simplifies purification. Secreted recombinant protein resulting from a large-scale fermentation can be purified by methods analogous to those disclosed by Urdal et al. (J. Chromatog. 296:171, 1984). This reference describes two sequential, reversed-phase HPLC steps for purification of recombinant human GM-CSF on a preparative HPLC column.

Human LIF-R synthesized in recombinant culture is characterized by the presence of non-human cell components, including proteins, in amounts and of a character which depend upon the purification steps taken to recover human LIF-R from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of LIF-R free of proteins which may be normally associated with LIF-R as it is found in nature in its species of origin, e.g. in cells, cell exudates or body fluids.

Uses of LIF-R Proteins and Compositions Comprising LIF-R

The LIF-R proteins disclosed herein find use as research reagents, as diagnostic reagents in in vitro assays, and in in vivo therapeutic procedures. Pharmaceutical compositions comprising an effective amount of LIF-R and a suitable diluent or carrier are provided by the present invention.

Cells expressing a membrane-bound recombinant LIF-R protein may be employed in studies of signal transduction; in various assays to detect LIF binding to the cells; or to analyze the ability of a particular protein (e.g., a soluble LIF-R) to compete with the membrane-bound LIF-R for binding of LIF. Labeled (e.g., radiolabeled) LIF-R may be used to assay a biological sample for LIF. Soluble LIF-R proteins are preferred for therapeutic use.

The present invention provides methods of using therapeutic compositions comprising a therapeutically effective amount of soluble LIF-R proteins and a suitable diluent and carrier, and methods for suppressing LIF-dependent biological responses in humans comprising administering an effective amount of soluble LIF-R protein. The therapeutically effective amount is an amount effective in ameliorating a LIF-mediated condition, and will vary according to the nature of the condition, the route of administration, the size of the patient, etc.

For therapeutic use, purified soluble LIF-R protein is administered to a patient, preferably a human, for treatment in a manner appropriate to the indication. Thus, for example, soluble LIF-R protein compositions can be administered by bolus injection, continuous infusion, sustained release from implants, or other suitable technique. Typically, a soluble LIF-R therapeutic agent will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining the LIF-R with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials.

Because LIF-R proteins bind to LIF, soluble LIF-R proteins can be used to competitively bind to LIF and thereby inhibit binding of LIF to cell surface LIF-R proteins. Soluble LIF-R is therefore expected to inhibit LIF-dependent biological activities. Soluble LIF-R may, for example, be useful in therapy to inhibit the effects of LIF induced cachexia in cancer patients or to treat lipoprotein metabolism defects such as atherosclerosis and obesity. Soluble LIF-R may also be useful in the treatment of disorders of bone and calcium metabolism or disorders associated with LIF overproduction associated with hepatocytes, neurons, and leukocytes. The regulation of embryonic and hematopoietic stem cells by LIF may also be manipulated with soluble LIF-R. Soluble LIF-R may also be used to treat leukemic cells which respond to LIF by proliferating.

LIF-R or antibodies to LIF-R may also be useful as a diagnostic reagent to detect diseases characterized by the presence of abnormal LIF-R.

Sense and Antisense Sequences

The present invention provides both double-stranded and single-stranded LIF-R DNA, and LIF-R mRNA as well. The single-stranded LIF-R nucleic acids have use as probes to detect the presence of hybridizing LIF-R nucleic acids (e.g., in in vitro assays) and as sense and antisense molecules to block expression of LIF-R.

In one embodiment, the present invention provides antisense or sense molecules comprising a single-stranded nucleic acid sequence (either RNA or DNA) capable of binding to target LIF-R mRNA (sense) or LIF-R DNA (antisense) sequences. These antisense or sense molecules may comprise a fragment of the coding region of LIF-R cDNA, and, in one embodiment, are oligonucleotides comprising at least about 14 nucleotides, preferably from about 14 to about 30 nucleotides, of a LIF-R cDNA sequence. The ability to create an antisense or sense oligonucleotide based upon a cDNA sequence for a given protein is described in, for example, Stein and Cohen, *Cancer Res.* 48:2659, 1988 and vander Krol et al., *BioTechniques* 6:958, 1988, which are hereby incorporated by reference.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The oligonucleotides thus may be used to block expression of LIF-R proteins. Uses of the antisense and sense nucleic acid sequences include, but are not limited to, use as research reagents. The biological effects of blocking LIF-R expression in cultured cells may be studied, for example. The oligonucleotides also may be employed in developing therapeutic procedures that involve blocking LIF-R expression in vivo.

Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are relatively stable in vivo (i.e., capable of resisting enzymatic degradation) but retain sequence specificity for binding to target nucleotide sequences. Other examples of sense or antisense oligonucleotides include those oligonucleotides which are covalently linked to organic moieties such as those described in WO 90/10448, or to other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any suitable method, including, for example, $CaPO_4$-mediated DNA transfection, electroporation, or by using gene transfer vectors such as Epstein-Barr virus. A preferred method involves insertion of the antisense or sense oligonucleotide into a suitable retroviral vector, then contacting the target cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide sequence by attaching the oligonucleotide to a molecule that binds to the target cell, as described in WO 91/04753. The oligonucleotide may be attached to molecules that include, but are not limited to, antibodies, growth factors, other cytokines, or other ligands that bind to cell surface receptors.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The following examples are offered by way of illustration, and not by way of limitation.

EXAMPLES

Example 1
Isolation and Expression of cDNAs Encoding Human LIF-R

A. Radiolabeling of LIF. Recombinant human LIF was expressed in yeast and purified to homogeneity essentially as described by Hopp, et al., *Bio/Technology* 6:1204, 1988. The purified protein was radiolabeled using a commercially available enzymobead radioiodination reagent (BioRad). In this procedure 10 µg rLIF in 50 µl 0.2M sodium phosphate, pH 7.2, are combined with 50 µl enzymobead reagent, 2 MCi of sodium iodide in 20 µl of 0.05M sodium phosphate pH 7.0 and 10 µl of 2.5% b-D-glucose. After 10 min at 25° C., sodium azide (20 µl of 50 mM) and sodium metabisulfite (10 µl of 5 mg/ml) were added and incubation continued for 5 min. at 25° C. The reaction mixture was fractionated by gel filtration on a 2 ml bed volume of Sephadex® G-25 (Sigma) equilibrated in Roswell Park Memorial Institute (RPMI) 1640 medium containing 2.5% (w/v) bovine serum albumin (BSA), 0.2% (w/v) sodium azide and 20 mM Hepes pH 7.4 (binding medium). The final pool of $^{125}$I-LIF was diluted to a working stock solution of $3 \times 10^{-8}$M in binding medium and stored for up to one month at 4° C. without detectable loss of receptor binding activity. The specific activity is routinely in the range of $6-8 \times 10^{15}$ cpm/mmole LIF.

B. Membrane Binding Assays. Human placental membranes were incubated at 4° C. for 2 hr with $^{125}$I-LIF in binding medium, 0.1% bacitracin, 0.02% aprotinin, and 0.4% BSA in a total volume of 1.2 ml. Control tubes containing in addition a 100-fold molar excess of unlabeled LIF were also included to determine non-specific binding. The reaction mixture was then centrifuged at 15,000×g in a microfuge for 5 minutes. Supernatants were discarded, the surface of the membrane pellets carefully rinsed with ice-cold binding medium, and the radioactivity counted on a gamma counter. Using this assay, it was determined that the LIF-R was present on placental membranes, and up to 96 fmols of $^{125}$I-LIF could be bound per mg of placental membrane protein.

C. Construction and Screening of Placental cDNA Library. A tissue source for LIF-R was selected by screening various human cell lines and tissues for expression of LIF-R based on their ability to bind $^{125}$I-labeled LIF, prepared as described above in Example 1A. An unsized cDNA library was constructed by reverse transcription of polyadenylated mRNA isolated from total RNA extracted from the human placental tissue (Ausubel et al., eds., *Current Protocols in Molecular Biology*, Vol. 1, 1987). The cells were harvested by lysing the tissue cells in a guanidinium isothiocyanate solution and total RNA was isolated using standard techniques as described by Maniatis, *Molecular Cloning: A laboratory Manual*, Cold Spring Harbor Laboratory, 1982.

Polyadenylated RNA was isolated by oligo dT cellulose chromatography and double-stranded cDNA was prepared by a method similar to that of Gubler and Hoffman, *Gene* 25:263, 1983. Briefly, the polyadenylated RNA was converted to an RNA-cDNA hybrid with reverse transcriptase using oligo dT as a primer. The RNA-cDNA hybrid was then converted into double-stranded cDNA using RNAase H in combination with DNA polymerase I. The resulting double stranded cDNA was blunt-ended with T4 DNA polymerase. BglII adaptors were ligated to the 5' ends of the resulting blunt-ended cDNA as described by Haymerle, et al., *Nucleic Acids Research* 14:8615, 1986. The non-ligated adaptors were removed by gel filtration chromatography at 68° C., leaving 24 nucleotide non-self-complementary overhangs on the cDNA. The same procedure was used to convert the 5' BglII ends of the mammalian expression vector pDC303 to 24 nucleotide overhangs complementary to those added to the cDNA.

The eukaryotic expression vector pDC303 was designed to express cDNA sequences inserted at its multiple cloning site when transfected into mammalian cells, and also replicates in *E. coli*. pDC303 was deposited in *E. coli* cells with the America Type Culture Collection on Feb. 27, 1992, under the designation *E. coli* DH5α, SF CAV, and was assigned accession no. 68922. pDC303 was assembled from pDC201 (a derivative of pMLSV, previously described by Cosman et al., *Nature* 312: 768, 1984), SV40 and cytomegalovirus DNA and comprises, in sequence: (1) SV40 sequences from coordinates 5171–270 containing the origin of replication, enhancer sequences and early and late promoters; (2) cytomegalovirus sequences containing the promoter and enhancer regions (nucleotides 671 to +63 from the sequence published by Boechart et al., *Cell* 41:521, 1985; (3) adenovirus-2 sequences from coordinates 5779–6079 containing sequences for the first exon of the tripartite leader (TPL), coordinates 7101–7172 and 9634–9693 containing the second exon and part of the third exon of the TPL and a multiple cloning site (MCS) containing sites for XhoI, KpnI, SmaI and BglI; (4) SV40 sequences from coordinates 4127–4100 and 2770–2533 containing the polyadenylation and termination signals for early transcription; (5) adenovirus sequences from coordinates 10532–11156 of the virus-associated RNA genes VAI and VAII; and (6) pBR322 sequences from coordinates 4363–2486 and 1094–375 containing the ampicillin resistance gene and origin of replication.

Optimal proportions of adaptored vector and cDNA were ligated in the presence of T4 polynucleotide kinase. Dialyzed ligation mixtures were electroporated into *E. coli* strain DH5α and transformants selected on ampicillin plates. Transformed *E. coli* cells were plated to provide approximately 2,400 colonies per plate and sufficient plates to provide approximately 240,000 total colonies per screen. Colonies were scraped from each plate, pooled, and plasmid DNA prepared from each pool. The pooled DNA was then used to transfect a subconfluent layer of monkey COS-7 cells. COS-7 cells were prepared for transfection by being maintained in complete medium (Dulbecco's modified Eagle's media (DNEM) containing 10% (v/v) fetal calf serum (FCS), 50 U/ml penicillin, 50 U/ml streptomycin, 2 mM L-glutamnine) and then plated at a density of $2 \times 10^5$ cells/well in either 6 well dishes (Falcon) or single well chambered slides (Lab-Tek). Both dishes and slides were pretreated with 1 ml human fibronectin (10 ug/mil in PBS) for 30 minutes followed by 1 wash with PBS. Media was removed from the adherent cell layer and replaced with 1.5 ml complete medium containing 134 mM chloroquine sulfate. 0.2 mls of DNA solution (2 μg DNA, 0.5 mg/ml DEAE-dextran in complete medium containing chloroquine) was then added to the cells and incubated for 5 hours. Following the incubation, the media was removed and the cells shocked by addition of complete medium containing 10% DMSO for 2 ½ to 20 minutes followed by replacement of the solution with fresh complete medium. The cells were grown in culture to permit transient expression of the inserted sequences. These conditions led to an 80% transfection frequency in surviving COS-7 cells.

After 48 to 72 hours, transfected monolayers of COS-7 cells were assayed for expression of LIF binding proteins by binding radioiodinated LIF (prepared as described above) using the following slide autoradiography technique. Transfected COS-7 cells were washed once with binding medium (RPMI media 1640 containing 25 mg/ml bovine serum albumin (BSA), 2 mg/ml sodium azide, 20 mM HEPES, pH 7.2, and 50 mg/ml nonfat dry milk (NFDM) and incubated for 2 hours at 4° C. with 1 ml binding medium+NFDM containing $1.25 \times 10^{-9}$M $^{125}$I-LIF. After incubation, cells in the chambered slides were washed three times with binding buffer+NFDM, followed by 2 washes with PBS, pH 7.3, to remove unbound $^{125}$I-LIF. The cells were fixed by incubating for 30 minutes at room temperature in 10% glutaraldehyde in PBS, pH 7.3, washed twice in PBS, and air dried. The slides were dipped in Kodak NTB-2 photographic emulsion (5×dilution in water) and exposed in the dark for 12 hours to 7 days at 4° C. in a light proof box. The slides were then developed for approximately 5 minutes in Kodak D19 developer (40 g/500 ml water), rinsed in water and fixed in Agfa G433C fixer. The slides were individually examined with a microscope at 25–40× magnification and positive cells expressing LIF-R were identified by the presence of autoradiographic silver grains against a light background.

Cells in the 6 well plates were washed once with binding buffer+NFDM followed by 3 washings with PBS, pH 7.3, to remove unbound $^{125}$I-LIF. The bound cells were then trypsinized to remove them from the plate and bound $^{125}$I-LIF were counted on a gamma counter.

Using the slide autoradiography approach, approximately 240,000 cDNAs were screened in pools of approximately 2,400 cDNAs until assay of one transfectant pool showed multiple cells clearly positive for LIF binding. This pool was then partitioned into pools of 600 and again screened by slide autoradiography and a positive pool was identified. This pool was further partitioned into pools of 60 and screened against by slide autoradiography until a positive pool was identified. Individual colonies from this pool of 60 were screened until a single clone (clone 65) was identified which directed synthesis of a surface protein with detectable LIF binding activity. This clone was isolated, and its insert is sequenced to determine the sequence of the human LIF-R cDNA clone 65. The pDC303 cloning vector containing the human LIF-R cDNA clone 65 was deposited with the American Type Culture Collection, Rockville, Md., USA (ATCC) on Dec. 11, 1990, under the name pHLIFR-65, and was assigned ATCC Accession Number 68491.

The nucleotide sequence of the cDNA insert of clone 65 is presented, along with the amino acid sequence encoded thereby, in SEQ ID NOS:1 and 2. Amino acids −44 through −1 constitute the signal peptide.

D. Binding to Intact Cells. Binding assays done with DA-1 cells grown in suspension culture were performed by a phthalate oil separation method (Dower et al., *J. Immunol.* 132:751, 1984) essentially as described by Park et al., *J. Biol. Chem* 261:4177, 1986 and Park et al., *Proc. Natl. Acad. Sci. USA* 84:5267, 1987. Nonspecific binding of $^{125}$I-LIF was measured in the presence of a 200-fold or greater molar excess of unlabeled LIF. Sodium azide (0.2%) was included in all binding assays to inhibit internalization of $^{125}$I-LIF at 37° C. The DA-1 cells bound $^{125}$I-LIF, and approximately 200 LIF receptors were determined to be present on the surface cells with an affinity constant ($K_a$) of about $7.4\times10^8 M^{-1}$.

Plasmid DNA from LIF receptor expression plasmid was used to transfect a subconfluent layer of monkey COS-7 cells using DEAE-dextran followed by chloroquine treatment, as described by Luthman et al. (*Nucl Acids Res.* 11:1295, 1983) and McCutchan et al. (*J. Natl. Cancer Inst.* 41:351, 1968). The cells were then grown in culture for three days to permit transient expression of the inserted sequences. After three days the cell monolayers were assayed for $^{125}$I-LIF binding essentially as described by Mosley et al., *Cell* 59:335, 1989. Non-specific binding of $^{125}$I-LIF was measured in the presence of 200-fold or greater excess of unlabeled LIF. Initial binding studies of $^{125}$I-LIF to COS cells transfected with LIF-R cDNA clone 65 indicated that high affinity binding ($K_a > 1\times10^9 M^{-1}$) was apparent following Scatchard analysis. pDC303 control vector transfected cells indicated that background endogenous LIF receptors are present on COS-7 cells. Control vector transfected cells expressed 130 high-affinity LIF receptors ($K_a = 4.2\times10^{10} M^{-1}$) and 2,400 receptors with lower affinity ($K_a = 7.8\times10^8 M^{-1}$). COS-7 cells were transfected with pDC303 containing LIF-R clone 65, and transfected cells were diluted 1:10 in cells that had been transfected with control pDC303 vector. This strategy was utilized as recombinant receptor expression can often be too great to allow accurate determinations of ligand-receptor affinity. Results of these experiments indicate that both affinity classes of LIF receptors were present following transfection with LIF-R clone 65. Approximately 178 high-affinity sites ($K_a = 1.4\times10^{11} M^{-1}$) and 9800 lower affinity sites ($K_a = 1.1\times10^9 M^{-1}$) were present on the LIF-R transfectants.

$^{35}$S-Labeling and Affinity Purification of LIF-R. COS-7 cells transfected with pDC303 or pDC303 containing the human LIF-R cDNA clone 65 were radiolabeled with $^{35}$S-cysteine/methionine. Detergent extracts of radiolabeled cells were prepared as described (Mosley et al., supra). LIF affinity matrices were prepared by coupling recombinant human LIF to cyanogen bromide-activated Sepharose (Pharmacia) or Hydrazide Affigel (Biorad), according to manufacturer's recommendations. A protein of $M_r$ approximately 190,000 was detected following affinity purification with either matrix, and SDS-PAGE analysis of LIF-R clone 65 COS-7 cell lysates, but was undetectable in control vector transfectants. The LIF-R clone 65 cDNA predicts a molecular weight of 111,374 and likely a high degree of glycosylation makes up the difference between this size and the observed $M_r$ of 190,000. Additionally, since the clone 65 LIF-R does not contain a stop codon in the 3' end of the cDNA, translation terminates 3 amino acids into the expression vector. Thus 401 daltons of the 190,000 LIF-R protein are encoded by these vector sequences.

F. Assay for Soluble LIF-R Proteins. Subclones derived from the extracellular domain of LIF-R cDNA clone 65 are assayed for the ability to encode soluble LIF-R proteins. COS-7 cells transfected with an expression vector containing the subcloned LIF-R cDNA are cultured to allow expression and secretion of the LIF-R protein. The presence of soluble LIF receptors in COS-7 supernatants is measured by inhibition of [$^{125}$I]LIF binding to pHLIFR-65 transfected COS-7 cells. Supernatants from control and soluble LIFR subclone transfected COS-7 cells are harvested in DMEM with 0.1% FCS three days post-transfection. [$^{125}$I]LIF binding was assessed as described above in the presence of 0.5 ml conditioned media, or in the presence or absence of 200-fold molar excess unlabeled LIF. Analogous procedures may be employed to test for the presence of other soluble LIF-R proteins (e.g., soluble murine LIF-R) in culture supernatants.

A probe derived from clone 65 was used to isolate additional human LIF-R clones, as described in Example 4. A composite human LIF-R sequence, derived by sequencing and alignment of cDNA and genomic clones, is presented in SEQ ID NOS:5 and 6.

Example 2
Isolation and Purification of cDNA Clones Encoding Murine LIF-R

A murine LIF-R cDNA was isolated from a library made from mouse liver cDNA (Stratagene, San Diego, Cat. #935302), by cross-species hybridization with a human LIF-R probe. A double-stranded human LIF-R probe was produced by excising a BglII fragment of the human LIF-R clone 65 and $^{32}$P-labeling the cDNA using random primers (Boehringer-Mannheim). A total of about $5\times10^5$ plaques were screened with the human probe in 35% formamide. Murine LIF-R cDNA clone 3 was isolated. This particular clone encoded a soluble version of the LIF receptor. The coding region encodes a LIF-R having about 70% identity at the amino acid level (80% similarity) and about 78% identity at the nucleotide level to the human LIF-R in the region of overlap.

The nucleotide sequence of the murine LIF-R cDNA of clone 3, and the amino acid sequence encoded thereby, are presented in SEQ ID NOS:3 and 4. The protein comprises a signal peptide (amino acids −43 to −1).

Example 3
Preparation of Monoclonal Antibodies to LIF-R

Preparations of purified recombinant LIF-R, for example, human LIF-R, or transfected COS cells expressing high levels of LIF-R are employed to generate monoclonal antibodies against LIF-R using conventional techniques. The immunogen may comprise a LIF-R protein (or fragment thereof, such as the extracellular domain) fused to the peptide Asp-Tyr-Lys-Asp-Asp-Asp-Asp-Lys (DYKDDDDK) (Hopp et al., BioTechnology 6:1204, 1988 and U.S. Pat. No. 5,011,912) or fused to the Fc portion of an antibody, as described above. Procedures for producing monoclonal antibodies include, for example, those disclosed in U.S. Pat. No. 4,411,993. Such antibodies are likely to be useful in interfering with LIF binding to LIF-R, for example, in ameliorating toxic or other undesired effects of LIF, or as components of diagnostic or research assays for LIF or soluble LIF-R.

To immunize mice, LIF-R immunogen is emulsified in complete Freund's adjuvant and injected in amounts ranging from 10–100 µg subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tailtip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS1. Other suitable known myeloma cell lines may be employed in place of NS1. A prefered murine myeloma cell line is P3x63 Ag 8.653 (ATCC CRL 1580). Hybridoma cell lines generated by this procedure are plated in multiple microtiter plates in a HAT selective medium (hypoxanthine, amninopterin, and thymidine) to inhibit proliferation of non-fused cells, myeloma hybrids, and spleen cell hybrids.

Hybridoma clones thus generated can be screened by ELISA for reactivity with LIF-R, for example, by adaptations of the techniques disclosed by Engvall et al., *Immunochem.* 8:871 (1971) and in U.S. Pat. No. 4,703,004. A preferred screening technique is the antibody capture technique described in Beckmann et al., (*J. Immunol.* 144:4212, 1990). Positive clones are then injected into the peritoneal cavities of syngeneic Balb/c mice to produce ascites containing high concentrations (>1 mg/ml) of anti-LIF-R monoclonal antibody. The resulting monoclonal antibody can be purified by ammonium sulfate precipitation followed by gel exclusion chromatography, and/or affinity chromatography based on binding of antibody to Protein A of *Staphylococcus aureus*.

Example 4
Isolation of Additional Human LIF-R Clones

Additional human LIF-R DNA sequences were isolated by screening human cDNA and genomic libraries with a probe derived from the human LIF-R cDNA isolated in Example 1. Sequencing and alignment of these clones produced the composite human LIF-R sequence presented in SEQ ID NOS:5 and 6.

The entire cDNA insert of pHLIFR-65 (Example 1) was excised by digestion with BglII, radiolabeled using a random priming kit (Stratagene Cloning Systems, La Jolla, Calif.), and used as a hybridization probe to screen the human placental cDNA library from which pHLIFR-65 was derived (Example 1). Hybridization procedures were essentially as described by Goodwin et al., supra, 1989. Positive clones were detected following high stringency washing conditions (0.2×SSC, 0.1% SDS at 65° C.).

DNA sequences of hybridizing clones were determined using vector- and cDNA-derived oligonucleotide primers on denatured double-stranded templates following shotgun and directed subcloning according to standard procedures (Sambrook, J., Fritsch, E. F. and Maniatis, T. (1989) *Molecular Cloning:A Laboratory Manual*, 2nd Edition, Cold Spring Harbor Laboratory Press, N.Y.).

As shown in SEQ ID NO:1, the cDNA insert in pHLIFR-65 (from Example 1) encoded a single large open reading frame that had no in-fame translation termination signal at its 3' end and, instead, ended in a stretch of 15 adenines (beginning after nucleotide 3143 in SEQ ID NO:1) that were not preceded by a typical polyadenylation signal. The open reading frame was terminated by an in-frame translational stop codon following 15 additional amino acids encoded by the Bgl II adaptors enmployed in library construction and by the expression vector. The 3' end of each additional isolated cDNA clone coincided with this poly-A stretch. Determination of the complete DNA sequence of one cDNA clone indicated that the sequences upstream of the poly A segment were identical to that of pHLIFR-65. Partial sequences were determined for the other clones, which matched corresponding portions of the pHLIFR-65 cDNA.

Based on the assumption that these cDNAs were the result of oligo(dT) priming at an internal site in the human LIFR mRNA during construction of the libraries, a human genomic library was screened with both the above-dscribed probe containing the entire pHLIFR cDNA insert, and also with a $^{32}$P-labeled oligonucleotide having the sequence of nucleotides 3099–3115 of SEQ ID NO:1 (near the 3' end of human clone 65). Four hybridizing clones were isolated. A subclone derived from one of the genomic clones (HLIFR-gen1) contained sequence that extended the cDNA sequence beyond the point at which the poly-A stretch of nucleotides began in the cDNA clones.

The sequence of the open reading frame deduced by alignment of pHLIFR-65 cDNA with the 3' genomic sequence (until the first in-frame stop codon was encountered) is presented in FIG. 2 and in SEQ ID NOS:5 and 6. In FIG. 2, the signal peptide comprises amino acids −44 to −1. The transmembrane domain is heavily underlined. Potential N-linked glycosylation sites are marked with asterisks. Hallmark residues associated with the hematopoietin family of receptors (Cosman et al., *Trends Biochem. Sci.*, 15:265 (1990) are shown boxed. The horizontal arrow marks the point at which genomic sequence was used to derive the 3' coding region of the HLIFR. All cDNA clones terminated with a stretch of A nucleotides at this point.

Comparison and alignment of the sequences of the positive clones produced the composite map of FIG. 1. In FIG. 1, clones isolated from the placental cDNA and genomic libraries are designated by "p" and "gen", respectively. The HLIFR open reading frame is shown boxed. The signal sequence is shown as a hatched box and the transmembrane domain is shown as a solid box. Some restriction endonuclease cleavage sites are shown.

In order to confirm that the genomic sequence used to complete the amino acid sequence of the HLIFR cytoplasmic domain was exonic, we used a PCR-based approach to detect the contiguous sequence assembled in FIG. 2 in human placental cDNA. First strand cDNA was prepared on a human placental mRNA template, using random primers in place of the oligo dT primer suspected of annealing to an internal poly-A site in the previously-described cDNA library. The first strand cDNA was used as a template in a PCR reaction primed with oligonucleotides that span two introns in the HLIFR gene (intron 1 of >700 bp @ nt 2770 and intron 2 of >900 bp @ nt 2848 in FIG. 2. The 5' primer employed in the PCR reaction (an oligonucleotide, the 5' end of which is at position 2720 of FIG. 2) anneals within the transmembrane region of the human LIF-R DNA. One 3' primer (an oligonucleotide having a 5' end at position 3233 of FIG. 2) anneals downstream of the point at which a poly-A segment is found in the previously isolated cDNAs (but within the coding region). The second 3' primer ( an oligonucleotide having a 5' end at position 3529 of FIG. 2) anneals within the 3' non-coding region of the FIG. 2 LIF-R sequence. The 5' oligonucleotide is based on the sequence of pHLIFR-65 and the 3' oligonucleotides are based on the sequence of the genomic clone. The PCR reaction products were separated by electrophoresis on an agarose gel, then transferred to nitrocellulose. The blot was probed with a 17-mer $^{32}$P-labeled oligonucleotide (nucleotides 3099–3115 of FIG. 2). First strand cDNA synthesis, the polymerase chain reaction and blotting from agarose gels were performed by procedures analogous to those described by Gearing et al., *EMBO J.* 8:3667–3676 (1989).

Amplification products expected if the composite FIG. 2 DNA sequence is exonic are 513 base pairs (5' primer to first 3' primer) and 809 base pairs (5' primer to the 3' primer in the noncoding region) in length. Specific amplification products of the predicted size were detected following PCR with the cDNA but not with genomic DNA as template. Since no bands were detected in the genomic PCR products it is likely that the distance between the primers (which includes the two introns discussed above) was too great for efficient PCR under the conditions used. The assembled sequence in FIG. 2 and SEQ ID NO:5 therefore corresponds to the true sequence of the human LIFR cDNA.

A DNA sequence comprising the full length coding region shown in FIG. 2 may be prepared by a number of different techniques. PCR reaction products produced as described above (with the 5' primer and the 3' primer that anneals in the 3' non-coding region) may be joined to the LIF-R cDNA of pHLIF-R-65 (example 1; contains 5' end of LIF-R sequence) by using a restriction endonuclease that cleaves within the region of overlap with the LIF-R cDNA of pHLIF-R-65. Computer programs that print out restriction sites within a given DNA sequence are known and available. In another approach, the genomic LIF-R DNA isolated above may be substituted for the PCR-amplified DNA, and joined to the pHLIF-R cDNA. Alternatively, the 3' end of the full length human LIF-R sequence may be chemically synthesized by conventional procedures and ligated to the pHLIF-R-65 cDNA (digested with a suitable restriction enzyme). As an additional alternative, a human placental cDNA library prepared using random primers for first strand cDNA synthesis may be screened with a probe derived from pHLIF-R-65 or the genomic clone isolated above to identify a full length cDNA clone.

The extracellular domain of the human LIF-R has homology to members of the hematopoietin receptor family (Cosman et al., supra) and contains two hematopoietin receptor domains (defined from the first conserved Cys residue to the Trp-Ser-X-Trp-Ser motif) and three repeats of a fibronectin type III-like module (FN III). The three FNIII domains span amino acids 487 (Thr) through 789 (Ser) of the SEQ ID NOS:2 and 6 sequences.

The presence of human LIFR cDNA clones in libraries prepared from placenta and liver suggests that the LIFR mRNA is normally expressed in these tissues. In order to define the size of the full-length LIFR mRNA, the cDNA insert of pBLIFR-65 was used to detect LIFR transcripts in human placental RNA. Resolution of RNA samples in agarose gels and transfer to nylon filters was accomplished as described previously (Goodwin et al., supra 1989). Blots were hybridized overnight with the entire insert of pHLIFR-65 that had been radiolabeled using a random priming kit (Stratagene), and washed using high stringency conditions.

Two major RNA species of ~6 kb and ~4.5 kb and a minor band of 5 kb were detected. These RNA species may represent alternately spliced transcripts, such as transcripts for membrane bound and soluble forms of the human LIF receptor, or transcripts utilizing different poly(A) addition signals.

Example 5
Soluble Human LIF-R/Fc Homodimer

An expression vector encoding a fragment of the human LIF-R extracellular domain fused to a polypeptide derived from the Fc region of an antibody was constructed as follows. Disulfide bonds form between the Fc portions of the expressed fusion proteins, creating homodimers.

Figure 4:
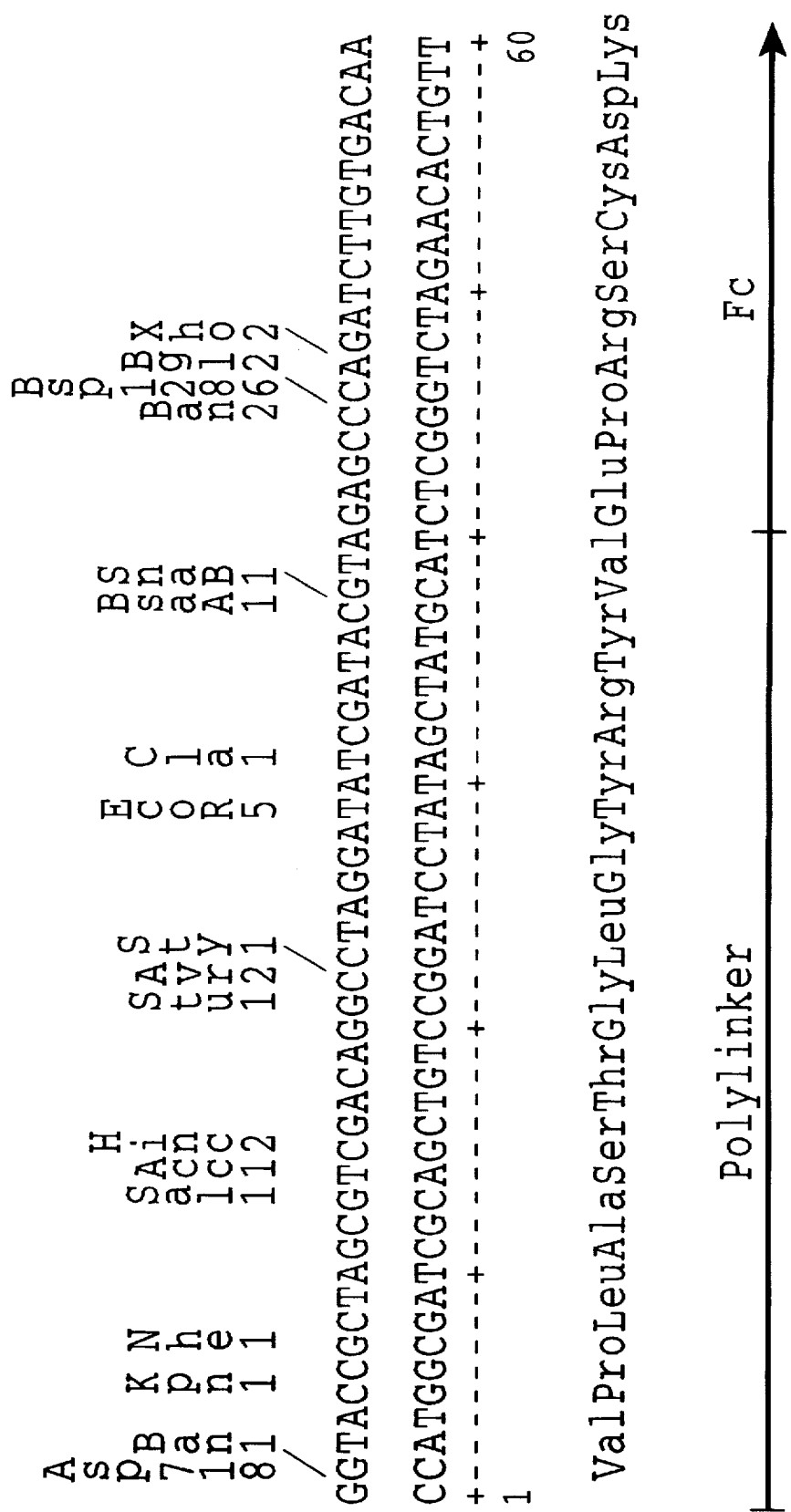
FIG. 4 shows the positions of restriction endonuclease cleavage sites in the polylinker segment and 5' end of the Fc cDNA insert in plasmid hIgG1Fc, as described in example 5.

Plasmid pHLIF-R-65, which contains human LIF-R cDNA in expression vector pDC303 as described in example 1, was digested with the restriction enzymes Asp718 and XmnI. Asp718 cleaves the vector upstream of the LIF-R cDNA insert. XmnI is a blunt cutter that cleaves within the codon for amino acid number 702 (Asp) of SEQ ID NO:1, upstream of the transmembrane region. The desired Asp718XmnI fragment (about 2,444 bp in length) was separated by electrophoresis on an agarose gel and purified by conventional procedures, using an Elutip column.

cDNA encoding a single chain polypeptide derived from the Fc region of a human IgG 1 antibody has been cloned into a pBLUESCRIPT SK® vector (Stratagene Cloning Systems, La Jolla, Calif.) to produce a recombinant vector designated hIgG1Fc. A polylinker region comprising a number of restriction sites is positioned immediately upstream of the Fc cDNA. The DNA and encoded amino acid sequences of the cloned Fc cDNA are presented in SEQ ID NO:7 and SEQ ID NO:8 (amino acids 14–245). Amino acids 1–13 of SEQ ID NOS:7 and 8 are encoded by the polylinker DNA segment FIG. 4 shows the positions of cleavage sites for a number of restriction enzymes in the polylinker and the 5' end of the Fc DNA.

The Fc polypeptide encoded by the cDNA extends from the N-terminal hinge region to the native C-terminus, i.e., is an essentially full-length antibody Fc region. Fc fragments, e.g., those that are truncated at the C-terriinal end, also may be employed. The fragments should contain multiple cysteine residues (at least the cysteine residues in the hinge reaction). The antibody from which the Fc polypeptide is derived is preferably of the same species as the patient to be treated with the fusion protein prepared therefrom.

Plasmid hIgG1Fc was digested with Asp718 and StuI, which cleave within the polylinker. The Asp718/XmnI LIF-R fragment prepared above was ligated into the cleaved hIgG1Fc vector by conventional techniques. StuI and XmnI both produce blunt ends, which will ligate together. In the resulting recombinant vector, the Fc encoding sequence is positioned downstream of, and in the same reading frame as, the LIF-R sequence. The encoded LIF-R/Fc fusion protein comprises amino acids –44 to 702 of SEQ ID NO:1, followed by amino acids 8 to 245 of SEQ ID NO:7. Amino acids 8 to 13 of SEQ ID NO:7 constitute a peptide linker encoded by the polylinker segment in this fusion protein. E. coli cells were transformed with the ligation mixture and plasmids were isolated therefrom by standard procedures. Plasmid vectors containing the desired DNA insert were identified by restriction endonuclease digestion analysis.

The cloned DNA segment encoding the LIF-R/Fc fusion polypeptide was excised from the recombinant vector by digestion with Asp718 and NotI. The NotI enzyme cleaves the vector in a polylinker region just downstream of the Fc cDNA insert. The excised DNA segment (3.2 kb) is inserted into an appropriate expression vector, depending on the type of host cell that is desired. One suitable expression vector is pDC304, a mammalian expression vector that is virtually identical to pDC303 (ATCC 68922, described in example 1) except that pDC304 contains a NotI site in the multiple cloning site (mcs). pDC304 is designed to express cDNA inserted into the mcs after transfection into mammalian cells.

pDC304 was cleaved with Asp718 and NotI, both of which cleave in the mcs. The LIF-R/Fc-encoding Asp718/NotI DNA fragment prepared above was ligated into the vector. COS-7 (monkey kidney) cells were transfected with the expression vector encoding the LIF-R/Fc fusion. The transfected cells were cultivated to allow expression of the fusion protein comprising the Fc polypeptide fused in frame (via the peptide linker) to the C-terminus of the LIF-R fragment. Disulfide bonds that form between the two Fc regions covalently link the two separate fusion polypeptides into a homodimer comprising two LIF-R polypeptides joined via disulfide bonds between the Fc moieties fused thereto. The LIF-R/Fc homodimer is a soluble protein.

The homodimer receptor protein may be purified using any of a number of conventional protein purification techniques. Since antibody Fc regions bind to protein A and protein G, affinity chromatography employing protein A or protein G attached to an insoluble support material may be employed in the purification process. In one procedure, one liter of culture supernatant containing the receptor is passed over a solid phase protein G column, and the column is then washed thoroughly with phosphate-buffered saline (PBS). The adsorbed Fc-containing fusion protein is eluted with 50 mM glycine buffer, pH 3, and brought to pH 7 with 2M Tris buffer, pH 9. Further purification may involve immunoaffinity column(s), e.g., affinity columns having LIF bound thereto.

In order to confirm dimer formation, COS-7 cells transfected with the hLIF-R/Fc-encoding expression vector were incubated with a mixture of $^{35}$S-methionine and $^{35}$S-cysteine for 3 hours. Duplicate 1-ml aliquots of the culture supernatant were incubated with 50 µl Protein G Sepharose beads (20% v/v, available from Pharmacia) overnight at 4° C. The beads were then pelleted by centrifugation, and protein was recovered from the beads with protein sample buffer±β-mercaptoethanol (BME). The molecular weight of the recovered protein was analyzed by SDS-PAGE. As expected, a protein band corresponding to the LIF-R/Fc monomer (about 160 kd) was visualized for samples treated with the BME reducing agent. A band corresponding to a protein of about 320 kd (double the monomer size) was seen on the -BME sample gel. No 160 kd (monomer) band was visible on the -BME sample gel. The dimer is believed to form either intracellularly or upon secretion from the transfected cells.

The binding affinity of the homodieric receptor for LIF was determined by performing a variation of a standard Scatchard analysis. The binding assay procedure was similar to that described by Mosley et al. (*Cell* 59:335, 1989) except that the receptor is attached to Protein G Sepharose beads, rather than being on the surface of transfected cells, during the assay. The LIF-R/Fc fusion protein attached to the beads is believed to be at least predominantly in dimeric form, as indicated above.

COS cells transfected with the hLIF-R/Fc-encoding expression vector were cultivated for 3 days to allow expression and secretion of the hLIF-R/Fc protein. 14 mls of culture supernatant were mixed with 700 µl of 20% (v/v) Protein G Sepharose beads in PBS+0.1% Triton X, and incubated overnight at 4° C. on a rocking platform. The beads were then washed twice with Binding Media (RPMI 1640 medium containing 2.5% bovine serum albumin, 0.2% (v/v) sodium azide and 20 mM Hepes, pH 7.4) and resuspended to 1.7 mls with Binding Media. In a 96-well microtiter plate, samples comprising 50 µl of the resuspended beads plus 50 µl Binding Medium plus one of ten 1:2 serial dilutions of $^{125}$I-LIF were incubated for 2 hours at 4° C. with shaking.

Tubes containing 250 µl newborn calf serum (NCS) were used in place of the phthalate oil-containing tubes used in the separation method referred to in example 1, section D. Duplicate 50 µl samples from the microtiter plate were applied to the tubes, which were then spun in a microfuge. Tubes were then cut, the radioactivity counted, and processed as for standard Scatchard analysis. The binding affinity of the homodimer for LIF ($9\times10^8 M^{-1}$) was comparable to that of the LIF-R encoded by clone 65 cDNA ($1.1\times10^9 M^{-1}$).

In an alternative construct, vector pHLIF-R-65 is cleaved with the restriction enzymes Asp718 and Bsp1286I. Asp718 cleaves in the vector upstream of the LIF-R cDNA insert. Bsp1286I cleaves just 3' of the codon for Val (amino acid 775 in SEQ ID NO:1). The Asp718/Bsp1286I LIF-R DNA fragment may be fused to an Fc polypeptide-encoding DNA fragment using suitable oligonucleotide linkers if desired. An additional alternative construct may be prepared by digesting hIgG1Fc with Asp718 and BglII. The BglII site shown in FIG. 4 (within the Fc sequence, near the 5' end) is unique. An oligonucleotide may be employed to regenerate the 5' end of the Fc sequence (through the codon for Glu at position 13) and add a suitable restriction site (e.g., for XmnI or Bsp1286I) for joining a LIF-R sequence to the Fc sequence.

Description of the Sequence Listing

SEQ ID NO:1 and SEQ ID NO:2 show the nucleotide sequence and encoded amino acid sequence of human LIF-R clone 65. This particular clone is a 5' fragment, lacking the 3' end of the coding region. The coding region spans from nucleotides 179–3182. The partial amino acid sequence of the mature peptide encoded by this nucleotide sequence is defined by amino acids 1–957. The predicted signal peptide is defined by amino acids −44 through −1. Though truncated at the C-terminus, the LIF-R protein encoded by clone 65 is capable of binding LIF, as described in Example 1.

SEQ ID NO:3 and SEQ ID NO:4 show the nucleotide sequence and encoded amino acid sequence of murine LIF-R clone 3. This particular clone is a naturally occurring soluble form of the murine LIF-R and has no transmembrane region. The absence of the transmembrane region allows the protein molecule to be transported through the cell membrane. The coding region spans from nucleotides 53–2212. The amino acid sequence of the mature peptide encoded by this nucleotide sequence is defined by amino acids 1–676. The predicted signal peptide is defined by amino acids −43 through −1.

SEQ ID NO:5 and SEQ ID NO:6 show a full length human LIF-R nucleotide sequence and the amino acid sequence encoded thereby. These sequences are composites derived from the sequencing of cDNA and genomic clones, as described in Example 4. The protein comprises a signal sequence (amino acids −44 through −1) followed by an extracellular domain (amino acids 1–789), a transmembrane region (amino acids 790–815), and a cytoplasmic domain (amino acids 816–1054).

SEQ ID NO:7 and SEQ ID NO:8 show the nucleotide sequence and amino acid sequence of a polylinker-encoded peptide (amino acids 1–13) fused to a polypeptide derived from the Fc region of a human IgGI antibody (amino acids 14–245). The Fc polypeptide extends from the hinge region to the native C-terminus.

We claim:

1. An isolated antibody that is immunoreactive with a LIF receptor (LIF-R), wherein said LIF-R is selected from the group consisting of a human LIF-R comprising the sequence of amino acids 1–957 of SEQ ID NO:2, and a murine LIF-R comprising the sequence of amino acids 1–676 of SEQ ID NO:4.

2. An antibody according to claim 1, wherein said antibody is a monoclonal antibody.

3. An antibody according to claim 2, wherein said LIF-R is a human LIF-R comprising the sequence of amino acids 1–957 of SEQ ID NO:2.

4. A monoclonal antibody that is immunoreactive with a LIF receptor (LIF-R), wherein said LIF-R comprises an amino acid sequence selected from the group consisting of amino acids 1–957 of SEQ ID NO:2, amino acids 1–676 of SEQ ID NO:4, and amino acids 1–1053 of SEQ ID NO:6.

5. A monoclonal antibody that is immunoreactive with a human LIF receptor comprising amino acids 1–957 of SEQ ID NO:2.

6. A hybridoma cell line that produces a monoclonal antibody according to claim 2.

7. A hybridoma cell line that produces a monoclonal antibody according to claim 4.

8. A hybridoma cell line that produces a monoclonal antibody according to claim 5.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 3182 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v ) FRAGMENT TYPE: N-terminal ( v i ) ORIGINAL SOURCE:
        ( F ) TISSUE TYPE: Placenta ( v i i ) IMMEDIATE SOURCE:
        ( B ) CLONE: hulifr.65

( i x ) FEATURE:
        ( A ) NAME/KEY: CDS
        ( B ) LOCATION: 179..3182

( i x ) FEATURE:
        ( A ) NAME/KEY: mat_peptide
        ( B ) LOCATION: 311..3179

( i x ) FEATURE:
        ( A ) NAME/KEY: sig_peptide
        ( B ) LOCATION: 179..310

( x i ) SEQUENCE DESCRIPTION: SEQ ID NO:1:

```
AGATCTTGGA  ACGAGACGAC  CTGCTCTCTC  TCCCAGAACG  TGTCTCTGCT  GCAAGGCACC          60

GGGCCCTTTC  GCTCTGCAGA  ACTGCACTTG  CAAGACCATT  ATCAACTCCT  AATCCCAGCT         120

CAGAAAGGGA  GCCTCTGCGA  CTCATTCATC  GCCCTCCAGG  ACTGACTGCA  TTGCACAG           178

ATG  ATG  GAT  ATT  TAC  GTA  TGT  TTG  AAA  CGA  CCA  TCC  TGG  ATG  GTG  GAC   226
Met  Met  Asp  Ile  Tyr  Val  Cys  Leu  Lys  Arg  Pro  Ser  Trp  Met  Val  Asp
-44            -40                       -35                      -30

AAT  AAA  AGA  ATG  AGG  ACT  GCT  TCA  AAT  TTC  CAG  TGG  CTG  TTA  TCA  ACA   274
Asn  Lys  Arg  Met  Arg  Thr  Ala  Ser  Asn  Phe  Gln  Trp  Leu  Leu  Ser  Thr
               -25                       -20                      -15

TTT  ATT  CTT  CTA  TAT  CTA  ATG  AAT  CAA  GTA  AAT  AGC  CAG  AAA  AAG  GGG   322
Phe  Ile  Leu  Leu  Tyr  Leu  Met  Asn  Gln  Val  Asn  Ser  Gln  Lys  Lys  Gly
          -10                       -5                        1

GCT  CCT  CAT  GAT  TTG  AAG  TGT  GTA  ACT  AAC  AAT  TTG  CAA  GTG  TGG  AAC   370
Ala  Pro  His  Asp  Leu  Lys  Cys  Val  Thr  Asn  Asn  Leu  Gln  Val  Trp  Asn
 5                      10                       15                       20

TGT  TCT  TGG  AAA  GCA  CCC  TCT  GGA  ACA  GGC  CGT  GGT  ACT  GAT  TAT  GAA   418
Cys  Ser  Trp  Lys  Ala  Pro  Ser  Gly  Thr  Gly  Arg  Gly  Thr  Asp  Tyr  Glu
                     25                       30                       35

GTT  TGC  ATT  GAA  AAC  AGG  TCC  CGT  TCT  TGT  TAT  CAG  TTG  GAG  AAA  ACC   466
Val  Cys  Ile  Glu  Asn  Arg  Ser  Arg  Ser  Cys  Tyr  Gln  Leu  Glu  Lys  Thr
               40                       45                       50

AGT  ATT  AAA  ATT  CCA  GCT  CTT  TCA  CAT  GGT  GAT  TAT  GAA  ATA  ACA  ATA   514
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Ser | Ile | Lys | Ile | Pro | Ala | Leu | Ser | His | Gly | Asp | Tyr | Glu | Ile | Thr | Ile |      |
|     |     | 55  |     |     |     |     | 60  |     |     |     |     | 65  |     |     |     |      |
| AAT | TCT | CTA | CAT | GAT | TTT | GGA | AGT | TCT | ACA | AGT | AAA | TTC | ACA | CTA | AAT | 562  |
| Asn | Ser | Leu | His | Asp | Phe | Gly | Ser | Ser | Thr | Ser | Lys | Phe | Thr | Leu | Asn |      |
|     | 70  |     |     |     |     | 75  |     |     |     |     | 80  |     |     |     |     |      |
| GAA | CAA | AAC | GTT | TCC | TTA | ATT | CCA | GAT | ACT | CCA | GAG | ATC | TTG | AAT | TTG | 610  |
| Glu | Gln | Asn | Val | Ser | Leu | Ile | Pro | Asp | Thr | Pro | Glu | Ile | Leu | Asn | Leu |      |
| 85  |     |     |     |     | 90  |     |     |     |     | 95  |     |     |     |     | 100 |      |
| TCT | GCT | GAT | TTC | TCA | ACC | TCT | ACA | TTA | TAC | CTA | AAG | TGG | AAC | GAC | AGG | 658  |
| Ser | Ala | Asp | Phe | Ser | Thr | Ser | Thr | Leu | Tyr | Leu | Lys | Trp | Asn | Asp | Arg |      |
|     |     |     |     | 105 |     |     |     |     | 110 |     |     |     |     | 115 |     |      |
| GGT | TCA | GTT | TTT | CCA | CAC | CGC | TCA | AAT | GTT | ATC | TGG | GAA | ATT | AAA | GTT | 706  |
| Gly | Ser | Val | Phe | Pro | His | Arg | Ser | Asn | Val | Ile | Trp | Glu | Ile | Lys | Val |      |
|     |     |     | 120 |     |     |     |     | 125 |     |     |     |     | 130 |     |     |      |
| CTA | CGT | AAA | GAG | AGT | ATG | GAG | CTC | GTA | AAA | TTA | GTG | ACC | CAC | AAC | ACA | 754  |
| Leu | Arg | Lys | Glu | Ser | Met | Glu | Leu | Val | Lys | Leu | Val | Thr | His | Asn | Thr |      |
|     |     | 135 |     |     |     |     | 140 |     |     |     |     | 145 |     |     |     |      |
| ACT | CTG | AAT | GGC | AAA | GAT | ACA | CTT | CAT | CAC | TGG | AGT | TGG | GCC | TCA | GAT | 802  |
| Thr | Leu | Asn | Gly | Lys | Asp | Thr | Leu | His | His | Trp | Ser | Trp | Ala | Ser | Asp |      |
|     | 150 |     |     |     |     | 155 |     |     |     |     | 160 |     |     |     |     |      |
| ATG | CCC | TTG | GAA | TGT | GCC | ATT | CAT | TTT | GTG | GAA | ATT | AGA | TGC | TAC | ATT | 850  |
| Met | Pro | Leu | Glu | Cys | Ala | Ile | His | Phe | Val | Glu | Ile | Arg | Cys | Tyr | Ile |      |
| 165 |     |     |     |     | 170 |     |     |     |     | 175 |     |     |     |     | 180 |      |
| GAC | AAT | CTT | CAT | TTT | TCT | GGT | CTC | GAA | GAG | TGG | AGT | GAC | TGG | AGC | CCT | 898  |
| Asp | Asn | Leu | His | Phe | Ser | Gly | Leu | Glu | Glu | Trp | Ser | Asp | Trp | Ser | Pro |      |
|     |     |     |     | 185 |     |     |     |     | 190 |     |     |     |     | 195 |     |      |
| GTG | AAG | AAC | ATT | TCT | TGG | ATA | CCT | GAT | TCT | CAG | ACT | AAG | GTT | TTT | CCT | 946  |
| Val | Lys | Asn | Ile | Ser | Trp | Ile | Pro | Asp | Ser | Gln | Thr | Lys | Val | Phe | Pro |      |
|     |     |     | 200 |     |     |     |     | 205 |     |     |     |     | 210 |     |     |      |
| CAA | GAT | AAA | GTG | ATA | CTT | GTA | GGC | TCA | GAC | ATA | ACA | TTT | TGT | TGT | GTG | 994  |
| Gln | Asp | Lys | Val | Ile | Leu | Val | Gly | Ser | Asp | Ile | Thr | Phe | Cys | Cys | Val |      |
|     |     | 215 |     |     |     |     | 220 |     |     |     |     | 225 |     |     |     |      |
| AGT | CAA | GAA | AAA | GTG | TTA | TCA | GCA | CTG | ATT | GGC | CAT | ACA | AAC | TGC | CCC | 1042 |
| Ser | Gln | Glu | Lys | Val | Leu | Ser | Ala | Leu | Ile | Gly | His | Thr | Asn | Cys | Pro |      |
|     | 230 |     |     |     |     | 235 |     |     |     |     | 240 |     |     |     |     |      |
| TTG | ATC | CAT | CTT | GAT | GGG | GAA | AAT | GTT | GCA | ATC | AAG | ATT | CGT | AAT | ATT | 1090 |
| Leu | Ile | His | Leu | Asp | Gly | Glu | Asn | Val | Ala | Ile | Lys | Ile | Arg | Asn | Ile |      |
| 245 |     |     |     |     | 250 |     |     |     |     | 255 |     |     |     |     | 260 |      |
| TCT | GTT | TCT | GCA | AGT | AGT | GGA | ACA | AAT | GTA | GTT | TTT | ACA | ACC | GAA | GAT | 1138 |
| Ser | Val | Ser | Ala | Ser | Ser | Gly | Thr | Asn | Val | Val | Phe | Thr | Thr | Glu | Asp |      |
|     |     |     |     | 265 |     |     |     |     | 270 |     |     |     |     | 275 |     |      |
| AAC | ATA | TTT | GGA | ACC | GTT | ATT | TTT | GCT | GGA | TAT | CCA | CCA | GAT | ACT | CCT | 1186 |
| Asn | Ile | Phe | Gly | Thr | Val | Ile | Phe | Ala | Gly | Tyr | Pro | Pro | Asp | Thr | Pro |      |
|     |     |     | 280 |     |     |     |     | 285 |     |     |     |     | 290 |     |     |      |
| CAA | CAA | CTG | AAT | TGT | GAG | ACA | CAT | GAT | TTA | AAA | GAA | ATT | ATA | TGT | AGT | 1234 |
| Gln | Gln | Leu | Asn | Cys | Glu | Thr | His | Asp | Leu | Lys | Glu | Ile | Ile | Cys | Ser |      |
|     |     | 295 |     |     |     |     | 300 |     |     |     |     | 305 |     |     |     |      |
| TGG | AAT | CCA | GGA | AGG | GTG | ACA | GCG | TTG | GTG | GGC | CCA | CGT | GCT | ACA | AGC | 1282 |
| Trp | Asn | Pro | Gly | Arg | Val | Thr | Ala | Leu | Val | Gly | Pro | Arg | Ala | Thr | Ser |      |
| 310 |     |     |     |     | 315 |     |     |     |     | 320 |     |     |     |     |     |      |
| TAC | ACT | TTA | GTT | GAA | AGT | TTT | TCA | GGA | AAA | TAT | GTT | AGA | CTT | AAA | AGA | 1330 |
| Tyr | Thr | Leu | Val | Glu | Ser | Phe | Ser | Gly | Lys | Tyr | Val | Arg | Leu | Lys | Arg |      |
| 325 |     |     |     |     | 330 |     |     |     |     | 335 |     |     |     |     | 340 |      |
| GCT | GAA | GCA | CCT | ACA | AAC | GAA | AGC | TAT | CAA | TTA | TTA | TTT | CAA | ATG | CTT | 1378 |
| Ala | Glu | Ala | Pro | Thr | Asn | Glu | Ser | Tyr | Gln | Leu | Leu | Phe | Gln | Met | Leu |      |
|     |     |     |     | 345 |     |     |     |     | 350 |     |     |     |     | 355 |     |      |
| CCA | AAT | CAA | GAA | ATA | TAT | AAT | TTT | ACT | TTG | AAT | GCT | CAC | AAT | CCG | CTG | 1426 |
| Pro | Asn | Gln | Glu | Ile | Tyr | Asn | Phe | Thr | Leu | Asn | Ala | His | Asn | Pro | Leu |      |
|     |     |     | 360 |     |     |     |     | 365 |     |     |     |     | 370 |     |     |      |
| GGT | CGA | TCA | CAA | TCA | ACA | ATT | TTA | GTT | AAT | ATA | ACT | GAA | AAA | GTT | TAT | 1474 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Gly | Arg | Ser | Gln | Ser | Thr | Ile | Leu | Val | Asn | Ile | Thr | Glu | Lys | Val | Tyr |      |
|     |     | 375 |     |     |     |     | 380 |     |     |     |     | 385 |     |     |     |      |
| CCC | CAT | ACT | CCT | ACT | TCA | TTC | AAA | GTG | AAG | GAT | ATT | AAT | TCA | ACA | GCT | 1522 |
| Pro | His | Thr | Pro | Thr | Ser | Phe | Lys | Val | Lys | Asp | Ile | Asn | Ser | Thr | Ala |      |
|     | 390 |     |     |     |     | 395 |     |     |     | 400 |     |     |     |     |     |      |
| GTT | AAA | CTT | TCT | TGG | CAT | TTA | CCA | GGC | AAC | TTT | GCA | AAG | ATT | AAT | TTT | 1570 |
| Val | Lys | Leu | Ser | Trp | His | Leu | Pro | Gly | Asn | Phe | Ala | Lys | Ile | Asn | Phe |      |
| 405 |     |     |     |     | 410 |     |     |     |     | 415 |     |     |     |     | 420 |      |
| TTA | TGT | GAA | ATT | GAA | ATT | AAG | AAA | TCT | AAT | TCA | GTA | CAA | GAG | CAG | CGG | 1618 |
| Leu | Cys | Glu | Ile | Glu | Ile | Lys | Lys | Ser | Asn | Ser | Val | Gln | Glu | Gln | Arg |      |
|     |     |     |     | 425 |     |     |     |     | 430 |     |     |     |     | 435 |     |      |
| AAT | GTC | ACA | ATC | AAA | GGA | GTA | GAA | AAT | TCA | AGT | TAT | CTT | GTT | GCT | CTG | 1666 |
| Asn | Val | Thr | Ile | Lys | Gly | Val | Glu | Asn | Ser | Ser | Tyr | Leu | Val | Ala | Leu |      |
|     |     |     | 440 |     |     |     |     | 445 |     |     |     |     | 450 |     |     |      |
| GAC | AAG | TTA | AAT | CCA | TAC | ACT | CTA | TAT | ACT | TTT | CGG | ATT | CGT | TGT | TCT | 1714 |
| Asp | Lys | Leu | Asn | Pro | Tyr | Thr | Leu | Tyr | Thr | Phe | Arg | Ile | Arg | Cys | Ser |      |
|     | 455 |     |     |     |     | 460 |     |     |     |     | 465 |     |     |     |     |      |
| ACT | GAA | ACT | TTC | TGG | AAA | TGG | AGC | AAA | TGG | AGC | AAT | AAA | AAA | CAA | CAT | 1762 |
| Thr | Glu | Thr | Phe | Trp | Lys | Trp | Ser | Lys | Trp | Ser | Asn | Lys | Lys | Gln | His |      |
| 470 |     |     |     |     | 475 |     |     |     |     | 480 |     |     |     |     |     |      |
| TTA | ACA | ACA | GAA | GCC | AGT | CCT | TCA | AAG | GGG | CCT | GAT | ACT | TGG | AGA | GAG | 1810 |
| Leu | Thr | Thr | Glu | Ala | Ser | Pro | Ser | Lys | Gly | Pro | Asp | Thr | Trp | Arg | Glu |      |
| 485 |     |     |     | 490 |     |     |     |     | 495 |     |     |     |     |     | 500 |      |
| TGG | AGT | TCT | GAT | GGA | AAA | AAT | TTA | ATA | ATC | TAT | TGG | AAG | CCT | TTA | CCC | 1858 |
| Trp | Ser | Ser | Asp | Gly | Lys | Asn | Leu | Ile | Ile | Tyr | Trp | Lys | Pro | Leu | Pro |      |
|     |     |     |     | 505 |     |     |     |     | 510 |     |     |     |     | 515 |     |      |
| ATT | AAT | GAA | GCT | AAT | GGA | AAA | ATA | CTT | TCC | TAC | AAT | GTA | TCG | TGT | TCA | 1906 |
| Ile | Asn | Glu | Ala | Asn | Gly | Lys | Ile | Leu | Ser | Tyr | Asn | Val | Ser | Cys | Ser |      |
|     |     |     |     | 520 |     |     |     |     | 525 |     |     |     |     | 530 |     |      |
| TCA | GAT | GAG | GAA | ACA | CAG | TCC | CTT | TCT | GAA | ATC | CCT | GAT | CCT | CAG | CAC | 1954 |
| Ser | Asp | Glu | Glu | Thr | Gln | Ser | Leu | Ser | Glu | Ile | Pro | Asp | Pro | Gln | His |      |
|     |     |     | 535 |     |     |     |     | 540 |     |     |     |     | 545 |     |     |      |
| AAA | GCA | GAG | ATA | CGA | CTT | GAT | AAG | AAT | GAC | TAC | ATC | ATC | AGC | GTA | GTG | 2002 |
| Lys | Ala | Glu | Ile | Arg | Leu | Asp | Lys | Asn | Asp | Tyr | Ile | Ile | Ser | Val | Val |      |
|     | 550 |     |     |     |     | 555 |     |     |     |     | 560 |     |     |     |     |      |
| GCT | AAA | AAT | TCT | GTG | GGC | TCA | TCA | CCA | CCT | TCC | AAA | ATA | GCG | AGT | ATG | 2050 |
| Ala | Lys | Asn | Ser | Val | Gly | Ser | Ser | Pro | Pro | Ser | Lys | Ile | Ala | Ser | Met |      |
| 565 |     |     |     |     | 570 |     |     |     |     | 575 |     |     |     |     | 580 |      |
| GAA | ATT | CCA | AAT | GAT | GAT | CTC | AAA | ATA | GAA | CAA | GTT | GTT | GGG | ATG | GGA | 2098 |
| Glu | Ile | Pro | Asn | Asp | Asp | Leu | Lys | Ile | Glu | Gln | Val | Val | Gly | Met | Gly |      |
|     |     |     |     | 585 |     |     |     |     | 590 |     |     |     |     | 595 |     |      |
| AAG | GGG | ATT | CTC | CTC | ACC | TGG | CAT | TAC | GAC | CCC | AAC | ATG | ACT | TGC | GAC | 2146 |
| Lys | Gly | Ile | Leu | Leu | Thr | Trp | His | Tyr | Asp | Pro | Asn | Met | Thr | Cys | Asp |      |
|     |     |     | 600 |     |     |     |     | 605 |     |     |     |     | 610 |     |     |      |
| TAC | GTC | ATT | AAG | TGG | TGT | AAC | TCG | TCT | CGG | TCG | GAA | CCA | TGC | CTT | ATG | 2194 |
| Tyr | Val | Ile | Lys | Trp | Cys | Asn | Ser | Ser | Arg | Ser | Glu | Pro | Cys | Leu | Met |      |
|     |     | 615 |     |     |     |     | 620 |     |     |     |     | 625 |     |     |     |      |
| GAC | TGG | AGA | AAA | GTT | CCC | TCA | AAC | AGC | ACT | GAA | ACT | GTA | ATA | GAA | TCT | 2242 |
| Asp | Trp | Arg | Lys | Val | Pro | Ser | Asn | Ser | Thr | Glu | Thr | Val | Ile | Glu | Ser |      |
|     | 630 |     |     |     |     | 635 |     |     |     |     | 640 |     |     |     |     |      |
| GAT | GAG | TTT | CGA | CCA | GGT | ATA | AGA | TAT | AAT | TTT | TTC | CTG | TAT | GGA | TGC | 2290 |
| Asp | Glu | Phe | Arg | Pro | Gly | Ile | Arg | Tyr | Asn | Phe | Phe | Leu | Tyr | Gly | Cys |      |
| 645 |     |     |     |     | 650 |     |     |     |     | 655 |     |     |     |     | 660 |      |
| AGA | AAT | CAA | GGA | TAT | CAA | TTA | TTA | CGC | TCC | ATG | ATT | GGA | TAT | ATA | GAA | 2338 |
| Arg | Asn | Gln | Gly | Tyr | Gln | Leu | Leu | Arg | Ser | Met | Ile | Gly | Tyr | Ile | Glu |      |
|     |     |     |     | 665 |     |     |     |     | 670 |     |     |     |     | 675 |     |      |
| GAA | TTG | GCT | CCC | ATT | GTT | GCA | CCA | AAT | TTT | ACT | GTT | GAG | GAT | ACT | TCT | 2386 |
| Glu | Leu | Ala | Pro | Ile | Val | Ala | Pro | Asn | Phe | Thr | Val | Glu | Asp | Thr | Ser |      |
|     |     |     | 680 |     |     |     |     | 685 |     |     |     |     | 690 |     |     |      |
| GCA | GAT | TCG | ATA | TTA | GTA | AAA | TGG | GAA | GAC | ATT | CCT | GTG | GAA | GAA | CTT | 2434 |

| | | | | | | | | | | | | | | | | |
|---|---|---|---|---|---|---|---|---|---|---|---|---|---|---|---|---|
| | Ala | Asp | Ser | Ile | Leu | Val | Lys | Trp | Glu | Asp | Ile | Pro | Val | Glu | Glu | Leu | |
| | | | 695 | | | | 700 | | | | | 705 | | | | | |
| AGA | GGC | TTT | TTA | AGA | GGA | TAT | TTG | TTT | TAC | TTT | GGA | AAA | GGA | GAA | AGA | | 2482 |
| Arg | Gly | Phe | Leu | Arg | Gly | Tyr | Leu | Phe | Tyr | Phe | Gly | Lys | Gly | Glu | Arg | | |
| | 710 | | | | 715 | | | | | 720 | | | | | | | |
| GAC | ACA | TCT | AAG | ATG | AGG | GTT | TTA | GAA | TCA | GGT | CGT | TCT | GAC | ATA | AAA | | 2530 |
| Asp | Thr | Ser | Lys | Met | Arg | Val | Leu | Glu | Ser | Gly | Arg | Ser | Asp | Ile | Lys | | |
| 725 | | | | | 730 | | | | | 735 | | | | | 740 | | |
| GTT | AAG | AAT | ATT | ACT | GAC | ATA | TCC | CAG | AAG | ACA | CTG | AGA | ATT | GCT | GAT | | 2578 |
| Val | Lys | Asn | Ile | Thr | Asp | Ile | Ser | Gln | Lys | Thr | Leu | Arg | Ile | Ala | Asp | | |
| | | | | 745 | | | | | 750 | | | | | 755 | | | |
| CTT | CAA | GGT | AAA | ACA | AGT | TAC | CAC | CTG | GTC | TTG | CGA | GCC | TAT | ACA | GAT | | 2626 |
| Leu | Gln | Gly | Lys | Thr | Ser | Tyr | His | Leu | Val | Leu | Arg | Ala | Tyr | Thr | Asp | | |
| | | | 760 | | | | | 765 | | | | | 770 | | | | |
| GGT | GGA | GTG | GGC | CCG | GAG | AAG | AGT | ATG | TAT | GTG | GTG | ACA | AAG | GAA | AAT | | 2674 |
| Gly | Gly | Val | Gly | Pro | Glu | Lys | Ser | Met | Tyr | Val | Val | Thr | Lys | Glu | Asn | | |
| | | 775 | | | | | 780 | | | | | 785 | | | | | |
| TCT | GTG | GGA | TTA | ATT | ATT | GCC | ATT | CTC | ATC | CCA | GTG | GCA | GTG | GCT | GTC | | 2722 |
| Ser | Val | Gly | Leu | Ile | Ile | Ala | Ile | Leu | Ile | Pro | Val | Ala | Val | Ala | Val | | |
| | 790 | | | | | 795 | | | | | 800 | | | | | | |
| ATT | GTT | GGA | GTG | GTG | ACA | AGT | ATC | CTT | TGC | TAT | CGG | AAA | CGA | GAA | TGG | | 2770 |
| Ile | Val | Gly | Val | Val | Thr | Ser | Ile | Leu | Cys | Tyr | Arg | Lys | Arg | Glu | Trp | | |
| 805 | | | | | 810 | | | | | 815 | | | | | 820 | | |
| ATT | AAA | GAA | ACC | TTC | TAC | CCT | GAT | ATT | CCA | AAT | CCA | GAA | AAC | TGT | AAA | | 2818 |
| Ile | Lys | Glu | Thr | Phe | Tyr | Pro | Asp | Ile | Pro | Asn | Pro | Glu | Asn | Cys | Lys | | |
| | | | | 825 | | | | | 830 | | | | | 835 | | | |
| GCA | TTA | CAG | TTT | CAA | AAG | AGT | GTC | TGT | GAG | GGA | AGC | AGT | GCT | CTT | AAA | | 2866 |
| Ala | Leu | Gln | Phe | Gln | Lys | Ser | Val | Cys | Glu | Gly | Ser | Ser | Ala | Leu | Lys | | |
| | | | 840 | | | | | 845 | | | | | 850 | | | | |
| ACA | TTG | GAA | ATG | AAT | CCT | TGT | ACC | CCA | AAT | AAT | GTT | GAG | GTT | CTG | GAA | | 2914 |
| Thr | Leu | Glu | Met | Asn | Pro | Cys | Thr | Pro | Asn | Asn | Val | Glu | Val | Leu | Glu | | |
| | | 855 | | | | | 860 | | | | | 865 | | | | | |
| ACT | CGA | TCA | GCA | TTT | CCT | AAA | ATA | GAA | GAT | ACA | GAA | ATA | ATT | TCC | CCA | | 2962 |
| Thr | Arg | Ser | Ala | Phe | Pro | Lys | Ile | Glu | Asp | Thr | Glu | Ile | Ile | Ser | Pro | | |
| | 870 | | | | | 875 | | | | | 880 | | | | | | |
| GTA | GCT | GAG | CGT | CCT | GAA | GAT | CGC | TCT | GAT | GCA | GAG | CCT | GAA | AAC | CAT | | 3010 |
| Val | Ala | Glu | Arg | Pro | Glu | Asp | Arg | Ser | Asp | Ala | Glu | Pro | Glu | Asn | His | | |
| 885 | | | | | 890 | | | | | 895 | | | | | 900 | | |
| GTG | GTT | GTG | TCC | TAT | TGT | CCA | CCC | ATC | ATT | GAG | GAA | GAA | ATA | CCA | AAC | | 3058 |
| Val | Val | Val | Ser | Tyr | Cys | Pro | Pro | Ile | Ile | Glu | Glu | Glu | Ile | Pro | Asn | | |
| | | | | 905 | | | | | 910 | | | | | 915 | | | |
| CCA | GCC | GCA | GAT | GAA | GCT | GGA | GGG | ACT | GCA | CAG | GTT | ATT | TAC | ATT | GAT | | 3106 |
| Pro | Ala | Ala | Asp | Glu | Ala | Gly | Gly | Thr | Ala | Gln | Val | Ile | Tyr | Ile | Asp | | |
| | | | 920 | | | | | 925 | | | | | 930 | | | | |
| GTT | CAG | TCG | ATG | TAT | CAG | CCT | CAA | GCA | AAA | CCA | GAA | GAA | AAA | AAA | AAA | | 3154 |
| Val | Gln | Ser | Met | Tyr | Gln | Pro | Gln | Ala | Lys | Pro | Glu | Glu | Lys | Lys | Lys | | |
| | | 935 | | | | | 940 | | | | | 945 | | | | | |
| AAA | AGC | AGG | TCG | TCT | CGT | TCC | AAG | ATC | T | | | | | | | | 3182 |
| Lys | Ser | Arg | Ser | Ser | Arg | Ser | Lys | Ile | | | | | | | | | |
| 950 | | | | | 955 | | | | | | | | | | | | |

( 2 ) INFORMATION FOR SEQ ID NO:2:

( i ) SEQUENCE CHARACTERISTICS:
        ( A ) LENGTH: 1001 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Met Asp Ile Tyr Val Cys Leu Lys Arg Pro Ser Trp Met Val Asp

|       |       |       |       |       |       |       |       |       |       |       |       |       |       |
|-------|-------|-------|-------|-------|-------|-------|-------|-------|-------|-------|-------|-------|-------|
| -44   |       |       |       | -40   |       |       |       | -35   |       |       |       | -30   |       |
| Asn   | Lys   | Arg   | Met   | Arg   | Thr   | Ala   | Ser   | Asn   | Phe   | Gln   | Trp   | Leu   | Leu   | Ser | Thr |

-25 -20 -15

Phe Ile Leu Leu Tyr Leu Met Asn Gln Val Asn Ser Gln Lys Lys Gly
-10 -5 1

Ala Pro His Asp Leu Lys Cys Val Thr Asn Asn Leu Gln Val Trp Asn
5 10 15 20

Cys Ser Trp Lys Ala Pro Ser Gly Thr Gly Arg Gly Thr Asp Tyr Glu
25 30 35

Val Cys Ile Glu Asn Arg Ser Arg Ser Cys Tyr Gln Leu Glu Lys Thr
40 45 50

Ser Ile Lys Ile Pro Ala Leu Ser His Gly Asp Tyr Glu Ile Thr Ile
55 60 65

Asn Ser Leu His Asp Phe Gly Ser Ser Thr Ser Lys Phe Thr Leu Asn
70 75 80

Glu Gln Asn Val Ser Leu Ile Pro Asp Thr Pro Glu Ile Leu Asn Leu
85 90 95 100

Ser Ala Asp Phe Ser Thr Ser Thr Leu Tyr Leu Lys Trp Asn Asp Arg
105 110 115

Gly Ser Val Phe Pro His Arg Ser Asn Val Ile Trp Glu Ile Lys Val
120 125 130

Leu Arg Lys Glu Ser Met Glu Leu Val Lys Leu Val Thr His Asn Thr
135 140 145

Thr Leu Asn Gly Lys Asp Thr Leu His His Trp Ser Trp Ala Ser Asp
150 155 160

Met Pro Leu Glu Cys Ala Ile His Phe Val Glu Ile Arg Cys Tyr Ile
165 170 175 180

Asp Asn Leu His Phe Ser Gly Leu Glu Glu Trp Ser Asp Trp Ser Pro
185 190 195

Val Lys Asn Ile Ser Trp Ile Pro Asp Ser Gln Thr Lys Val Phe Pro
200 205 210

Gln Asp Lys Val Ile Leu Val Gly Ser Asp Ile Thr Phe Cys Cys Val
215 220 225

Ser Gln Glu Lys Val Leu Ser Ala Leu Ile Gly His Thr Asn Cys Pro
230 235 240

Leu Ile His Leu Asp Gly Glu Asn Val Ala Ile Lys Ile Arg Asn Ile
245 250 255 260

Ser Val Ser Ala Ser Ser Gly Thr Asn Val Val Phe Thr Thr Glu Asp
265 270 275

Asn Ile Phe Gly Thr Val Ile Phe Ala Gly Tyr Pro Pro Asp Thr Pro
280 285 290

Gln Gln Leu Asn Cys Glu Thr His Asp Leu Lys Glu Ile Ile Cys Ser
295 300 305

Trp Asn Pro Gly Arg Val Thr Ala Leu Val Gly Pro Arg Ala Thr Ser
310 315 320

Tyr Thr Leu Val Glu Ser Phe Ser Gly Lys Tyr Val Arg Leu Lys Arg
325 330 335 340

Ala Glu Ala Pro Thr Asn Glu Ser Tyr Gln Leu Leu Phe Gln Met Leu
345 350 355

Pro Asn Gln Glu Ile Tyr Asn Phe Thr Leu Asn Ala His Asn Pro Leu
360 365 370

Gly Arg Ser Gln Ser Thr Ile Leu Val Asn Ile Thr Glu Lys Val Tyr
375 380 385

| Pro | His | Thr | Pro | Thr | Ser | Phe | Lys | Val | Lys | Asp | Ile | Asn | Ser | Thr | Ala |
|---|---|---|---|---|---|---|---|---|---|---|---|---|---|---|---|
| | 390 | | | | 395 | | | | 400 | | | | | | |
| Val | Lys | Leu | Ser | Trp | His | Leu | Pro | Gly | Asn | Phe | Ala | Lys | Ile | Asn | Phe |
| 405 | | | | | 410 | | | | 415 | | | | | | 420 |
| Leu | Cys | Glu | Ile | Glu | Ile | Lys | Lys | Ser | Asn | Ser | Val | Gln | Glu | Gln | Arg |
| | | | | 425 | | | | | 430 | | | | | 435 | |
| Asn | Val | Thr | Ile | Lys | Gly | Val | Glu | Asn | Ser | Ser | Tyr | Leu | Val | Ala | Leu |
| | | | 440 | | | | | 445 | | | | | 450 | | |
| Asp | Lys | Leu | Asn | Pro | Tyr | Thr | Leu | Tyr | Thr | Phe | Arg | Ile | Arg | Cys | Ser |
| | | 455 | | | | 460 | | | | | 465 | | | | |
| Thr | Glu | Thr | Phe | Trp | Lys | Trp | Ser | Lys | Trp | Ser | Asn | Lys | Lys | Gln | His |
| | 470 | | | | 475 | | | | | 480 | | | | | |
| Leu | Thr | Thr | Glu | Ala | Ser | Pro | Ser | Lys | Gly | Pro | Asp | Thr | Trp | Arg | Glu |
| 485 | | | | 490 | | | | | 495 | | | | | | 500 |
| Trp | Ser | Ser | Asp | Gly | Lys | Asn | Leu | Ile | Ile | Tyr | Trp | Lys | Pro | Leu | Pro |
| | | | | 505 | | | | | 510 | | | | | 515 | |
| Ile | Asn | Glu | Ala | Asn | Gly | Lys | Ile | Leu | Ser | Tyr | Asn | Val | Ser | Cys | Ser |
| | | | 520 | | | | | 525 | | | | | 530 | | |
| Ser | Asp | Glu | Glu | Thr | Gln | Ser | Leu | Ser | Glu | Ile | Pro | Asp | Pro | Gln | His |
| | | 535 | | | | | 540 | | | | | 545 | | | |
| Lys | Ala | Glu | Ile | Arg | Leu | Asp | Lys | Asn | Asp | Tyr | Ile | Ile | Ser | Val | Val |
| | 550 | | | | | 555 | | | | | 560 | | | | |
| Ala | Lys | Asn | Ser | Val | Gly | Ser | Ser | Pro | Pro | Ser | Lys | Ile | Ala | Ser | Met |
| 565 | | | | | 570 | | | | | 575 | | | | | 580 |
| Glu | Ile | Pro | Asn | Asp | Asp | Leu | Lys | Ile | Glu | Gln | Val | Val | Gly | Met | Gly |
| | | | | 585 | | | | | 590 | | | | | 595 | |
| Lys | Gly | Ile | Leu | Leu | Thr | Trp | His | Tyr | Asp | Pro | Asn | Met | Thr | Cys | Asp |
| | | | 600 | | | | | 605 | | | | | 610 | | |
| Tyr | Val | Ile | Lys | Trp | Cys | Asn | Ser | Ser | Arg | Ser | Glu | Pro | Cys | Leu | Met |
| | | 615 | | | | | 620 | | | | | 625 | | | |
| Asp | Trp | Arg | Lys | Val | Pro | Ser | Asn | Ser | Thr | Glu | Thr | Val | Ile | Glu | Ser |
| | 630 | | | | | 635 | | | | | 640 | | | | |
| Asp | Glu | Phe | Arg | Pro | Gly | Ile | Arg | Tyr | Asn | Phe | Phe | Leu | Tyr | Gly | Cys |
| 645 | | | | | 650 | | | | | 655 | | | | | 660 |
| Arg | Asn | Gln | Gly | Tyr | Gln | Leu | Leu | Arg | Ser | Met | Ile | Gly | Tyr | Ile | Glu |
| | | | | 665 | | | | | 670 | | | | | 675 | |
| Glu | Leu | Ala | Pro | Ile | Val | Ala | Pro | Asn | Phe | Thr | Val | Glu | Asp | Thr | Ser |
| | | | 680 | | | | | 685 | | | | | 690 | | |
| Ala | Asp | Ser | Ile | Leu | Val | Lys | Trp | Glu | Asp | Ile | Pro | Val | Glu | Glu | Leu |
| | | 695 | | | | | 700 | | | | | 705 | | | |
| Arg | Gly | Phe | Leu | Arg | Gly | Tyr | Leu | Phe | Tyr | Phe | Gly | Lys | Gly | Glu | Arg |
| | 710 | | | | | 715 | | | | | 720 | | | | |
| Asp | Thr | Ser | Lys | Met | Arg | Val | Leu | Glu | Ser | Gly | Arg | Ser | Asp | Ile | Lys |
| 725 | | | | | 730 | | | | | 735 | | | | | 740 |
| Val | Lys | Asn | Ile | Thr | Asp | Ile | Ser | Gln | Lys | Thr | Leu | Arg | Ile | Ala | Asp |
| | | | | 745 | | | | | 750 | | | | | 755 | |
| Leu | Gln | Gly | Lys | Thr | Ser | Tyr | His | Leu | Val | Leu | Arg | Ala | Tyr | Thr | Asp |
| | | | 760 | | | | | 765 | | | | | 770 | | |
| Gly | Gly | Val | Gly | Pro | Glu | Lys | Ser | Met | Tyr | Val | Val | Thr | Lys | Glu | Asn |
| | | 775 | | | | | 780 | | | | | 785 | | | |
| Ser | Val | Gly | Leu | Ile | Ile | Ala | Ile | Leu | Ile | Pro | Val | Ala | Val | Ala | Val |
| | 790 | | | | | 795 | | | | | 800 | | | | |
| Ile | Val | Gly | Val | Val | Thr | Ser | Ile | Leu | Cys | Tyr | Arg | Lys | Arg | Glu | Trp |
| 805 | | | | | 810 | | | | | 815 | | | | | 820 |

| Ile | Lys | Glu | Thr | Phe | Tyr | Pro | Asp | Ile | Pro | Asn | Pro | Glu | Asn | Cys | Lys |
|---|---|---|---|---|---|---|---|---|---|---|---|---|---|---|---|
|  |  |  |  | 825 |  |  |  | 830 |  |  |  |  |  | 835 |  |

| Ala | Leu | Gln | Phe | Gln | Lys | Ser | Val | Cys | Glu | Gly | Ser | Ser | Ala | Leu | Lys |
|---|---|---|---|---|---|---|---|---|---|---|---|---|---|---|---|
|  |  |  | 840 |  |  |  |  | 845 |  |  |  |  | 850 |  |  |

| Thr | Leu | Glu | Met | Asn | Pro | Cys | Thr | Pro | Asn | Asn | Val | Glu | Val | Leu | Glu |
|---|---|---|---|---|---|---|---|---|---|---|---|---|---|---|---|
|  |  | 855 |  |  |  |  | 860 |  |  |  |  | 865 |  |  |  |

| Thr | Arg | Ser | Ala | Phe | Pro | Lys | Ile | Glu | Asp | Thr | Glu | Ile | Ile | Ser | Pro |
|---|---|---|---|---|---|---|---|---|---|---|---|---|---|---|---|
|  | 870 |  |  |  |  | 875 |  |  |  |  | 880 |  |  |  |  |

| Val | Ala | Glu | Arg | Pro | Glu | Asp | Arg | Ser | Asp | Ala | Glu | Pro | Glu | Asn | His |
|---|---|---|---|---|---|---|---|---|---|---|---|---|---|---|---|
| 885 |  |  |  |  | 890 |  |  |  |  | 895 |  |  |  |  | 900 |

| Val | Val | Val | Ser | Tyr | Cys | Pro | Pro | Ile | Ile | Glu | Glu | Glu | Ile | Pro | Asn |
|---|---|---|---|---|---|---|---|---|---|---|---|---|---|---|---|
|  |  |  |  | 905 |  |  |  |  | 910 |  |  |  |  | 915 |  |

| Pro | Ala | Ala | Asp | Glu | Ala | Gly | Gly | Thr | Ala | Gln | Val | Ile | Tyr | Ile | Asp |
|---|---|---|---|---|---|---|---|---|---|---|---|---|---|---|---|
|  |  |  | 920 |  |  |  |  | 925 |  |  |  |  | 930 |  |  |

| Val | Gln | Ser | Met | Tyr | Gln | Pro | Gln | Ala | Lys | Pro | Glu | Glu | Lys | Lys | Lys |
|---|---|---|---|---|---|---|---|---|---|---|---|---|---|---|---|
|  |  | 935 |  |  |  |  | 940 |  |  |  |  | 945 |  |  |  |

| Lys | Ser | Arg | Ser | Ser | Arg | Ser | Lys | Ile |
|---|---|---|---|---|---|---|---|---|
|  | 950 |  |  |  |  | 955 |  |  |

( 2 ) INFORMATION FOR SEQ ID NO:3:

( i ) SEQUENCE CHARACTERISTICS:
        ( A ) LENGTH: 2498 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i i ) IMMEDIATE SOURCE:
        ( B ) CLONE: mulifr-3

( i x ) FEATURE:
        ( A ) NAME/KEY: CDS
        ( B ) LOCATION: 53..2212

( i x ) FEATURE:
        ( A ) NAME/KEY: mat_peptide
        ( B ) LOCATION: 182..2209

( i x ) FEATURE:
        ( A ) NAME/KEY: sig_peptide
        ( B ) LOCATION: 53..181

( x i ) SEQUENCE DESCRIPTION: SEQ ID NO:3:

```
CCCCCTCCGT GGCATTGGCT CCTGCCCAGG GGCTGACTGA ACAGCAAGGA CA ATG        55
                                                          Met
                                                          -43
```

| GCA | GCT | TAC | TCA | TGG | TGG | AGA | CAG | CCA | TCG | TGG | ATG | GTA | GAC | AAT | AAA | 103 |
|---|---|---|---|---|---|---|---|---|---|---|---|---|---|---|---|---|
| Ala | Ala | Tyr | Ser | Trp | Trp | Arg | Gln | Pro | Ser | Trp | Met | Val | Asp | Asn | Lys |  |
|  |  | -40 |  |  |  | -35 |  |  |  | -30 |  |  |  |  |  |  |

| AGA | TCG | AGG | ATG | ACT | CCA | AAC | CTG | CCA | TGG | CTC | CTG | TCA | GCT | CTG | ACC | 151 |
|---|---|---|---|---|---|---|---|---|---|---|---|---|---|---|---|---|
| Arg | Ser | Arg | Met | Thr | Pro | Asn | Leu | Pro | Trp | Leu | Leu | Ser | Ala | Leu | Thr |  |
| -25 |  |  |  |  | -20 |  |  |  |  | -15 |  |  |  |  |  |  |

| CTC | CTG | CAT | CTG | ACG | ATG | CAT | GCA | AAC | GGT | CTG | AAG | AGA | GGG | GTA | CAA | 199 |
|---|---|---|---|---|---|---|---|---|---|---|---|---|---|---|---|---|
| Leu | Leu | His | Leu | Thr | Met | His | Ala | Asn | Gly | Leu | Lys | Arg | Gly | Val | Gln |  |
| -10 |  |  |  |  | -5 |  |  |  | 1 |  |  |  | 5 |  |  |  |

| GAC | TTG | AAA | TGC | ACA | ACC | AAC | AAC | ATG | CGA | GTG | TGG | GAC | TGC | ACG | TGG | 247 |
|---|---|---|---|---|---|---|---|---|---|---|---|---|---|---|---|---|
| Asp | Leu | Lys | Cys | Thr | Thr | Asn | Asn | Met | Arg | Val | Trp | Asp | Cys | Thr | Trp |  |
|  |  |  | 10 |  |  |  |  | 15 |  |  |  |  | 20 |  |  |  |

| | | | | | | | | | | | | | | | | |
|---|---|---|---|---|---|---|---|---|---|---|---|---|---|---|---|---|
| CCA | GCT | CCC | CTC | GGG | GTC | AGC | CCT | GGA | ACT | GTT | AAA | GAT | ATT | TGC | ATT | 295 |
| Pro | Ala | Pro | Leu | Gly | Val | Ser | Pro | Gly | Thr | Val | Lys | Asp | Ile | Cys | Ile | |
| | | 25 | | | | | 30 | | | | | 35 | | | | |
| AAA | GAC | AGG | TTC | CAT | TCT | TGT | CAC | CCA | TTA | GAG | ACA | ACA | AAC | GTT | AAA | 343 |
| Lys | Asp | Arg | Phe | His | Ser | Cys | His | Pro | Leu | Glu | Thr | Thr | Asn | Val | Lys | |
| | 40 | | | | 45 | | | | | 50 | | | | | | |
| ATT | CCA | GCT | CTT | TCA | CCT | GGT | GAT | CAC | GAA | GTC | ACA | ATA | AAT | TAT | CTA | 391 |
| Ile | Pro | Ala | Leu | Ser | Pro | Gly | Asp | His | Glu | Val | Thr | Ile | Asn | Tyr | Leu | |
| 55 | | | | | 60 | | | | | 65 | | | | | 70 | |
| AAT | GGC | TTT | CAG | AGT | AAA | TTC | ACG | TTG | AAT | GAA | AAA | GAT | GTC | TCT | TTA | 439 |
| Asn | Gly | Phe | Gln | Ser | Lys | Phe | Thr | Leu | Asn | Glu | Lys | Asp | Val | Ser | Leu | |
| | | | | 75 | | | | | 80 | | | | | 85 | | |
| ATT | CCA | GAG | ACT | CCC | GAG | ATC | CTG | GAT | TTG | TCT | GCT | GAC | TTC | TTC | ACC | 487 |
| Ile | Pro | Glu | Thr | Pro | Glu | Ile | Leu | Asp | Leu | Ser | Ala | Asp | Phe | Phe | Thr | |
| | | | 90 | | | | | 95 | | | | | 100 | | | |
| TCC | TCC | TTA | CTA | CTG | AAG | TGG | AAC | GAC | AGA | GGG | TCT | GCT | CTG | CCT | CAC | 535 |
| Ser | Ser | Leu | Leu | Leu | Lys | Trp | Asn | Asp | Arg | Gly | Ser | Ala | Leu | Pro | His | |
| | | 105 | | | | | 110 | | | | | 115 | | | | |
| CCC | TCC | AAT | GCC | ACC | TGG | GAG | ATT | AAG | GTT | CTA | CAG | AAT | CCA | AGG | ACG | 583 |
| Pro | Ser | Asn | Ala | Thr | Trp | Glu | Ile | Lys | Val | Leu | Gln | Asn | Pro | Arg | Thr | |
| | 120 | | | | | 125 | | | | | 130 | | | | | |
| GAA | CCA | GTA | GCA | CTC | GTG | TTA | CTC | AAC | ACA | ATG | CTG | AGT | GGT | AAA | GAT | 631 |
| Glu | Pro | Val | Ala | Leu | Val | Leu | Leu | Asn | Thr | Met | Leu | Ser | Gly | Lys | Asp | |
| 135 | | | | | 140 | | | | | 145 | | | | | 150 | |
| ACC | GTT | CAG | CAC | TGG | AAC | TGG | ACC | TCA | GAC | CTG | CCC | TTG | CAA | TGT | GCC | 679 |
| Thr | Val | Gln | His | Trp | Asn | Trp | Thr | Ser | Asp | Leu | Pro | Leu | Gln | Cys | Ala | |
| | | | | 155 | | | | | 160 | | | | | 165 | | |
| ACT | CAC | TCG | GTG | AGC | ATT | CGA | TGG | CAC | ATT | GAC | TCG | CCT | CAT | TTC | TCC | 727 |
| Thr | His | Ser | Val | Ser | Ile | Arg | Trp | His | Ile | Asp | Ser | Pro | His | Phe | Ser | |
| | | | 170 | | | | | 175 | | | | | 180 | | | |
| GGT | TAC | AAA | GAG | TGG | AGT | GAC | TGG | AGC | CCG | CTG | AAG | AAC | ATC | TCC | TGG | 775 |
| Gly | Tyr | Lys | Glu | Trp | Ser | Asp | Trp | Ser | Pro | Leu | Lys | Asn | Ile | Ser | Trp | |
| | | 185 | | | | | 190 | | | | | 195 | | | | |
| ATT | CGT | AAT | ACA | GAG | ACT | AAT | GTT | TTT | CCT | CAA | GAC | AAA | GTG | GTG | CTC | 823 |
| Ile | Arg | Asn | Thr | Glu | Thr | Asn | Val | Phe | Pro | Gln | Asp | Lys | Val | Val | Leu | |
| | 200 | | | | | 205 | | | | | 210 | | | | | |
| GCA | GGC | TCA | AAC | ATG | ACA | ATT | TGT | TGT | ATG | AGT | CCA | ACG | AAA | GTG | CTT | 871 |
| Ala | Gly | Ser | Asn | Met | Thr | Ile | Cys | Cys | Met | Ser | Pro | Thr | Lys | Val | Leu | |
| 215 | | | | | 220 | | | | | 225 | | | | | 230 | |
| TCA | GGA | CAG | ATC | GGC | AAT | ACC | CTT | CGT | CCT | CTC | ATC | CAT | CTG | TAC | GGG | 919 |
| Ser | Gly | Gln | Ile | Gly | Asn | Thr | Leu | Arg | Pro | Leu | Ile | His | Leu | Tyr | Gly | |
| | | | | 235 | | | | | 240 | | | | | 245 | | |
| CAA | ACC | GTT | GCG | ATC | CAT | ATC | CTG | AAC | ATC | CCC | GTT | TCT | GAA | AAC | AGT | 967 |
| Gln | Thr | Val | Ala | Ile | His | Ile | Leu | Asn | Ile | Pro | Val | Ser | Glu | Asn | Ser | |
| | | | 250 | | | | | 255 | | | | | 260 | | | |
| GGC | ACA | AAC | ATC | ATT | TTC | ATC | ACA | GAC | GAC | GAT | GTG | TAC | GGA | ACG | GTG | 1015 |
| Gly | Thr | Asn | Ile | Ile | Phe | Ile | Thr | Asp | Asp | Asp | Val | Tyr | Gly | Thr | Val | |
| | | 265 | | | | | 270 | | | | | 275 | | | | |
| GTC | TTT | GCA | GGC | TAT | CCT | CCC | GAT | GTT | CCT | CAG | AAG | CTG | AGC | TGT | GAG | 1063 |
| Val | Phe | Ala | Gly | Tyr | Pro | Pro | Asp | Val | Pro | Gln | Lys | Leu | Ser | Cys | Glu | |
| | 280 | | | | | 285 | | | | | 290 | | | | | |
| ACA | CAT | GAC | TTA | AAA | GAG | ATT | ATA | TGT | AGC | TGG | AAT | CCA | GGA | AGG | ATA | 1111 |
| Thr | His | Asp | Leu | Lys | Glu | Ile | Ile | Cys | Ser | Trp | Asn | Pro | Gly | Arg | Ile | |
| 295 | | | | | 300 | | | | | 305 | | | | | 310 | |
| ACT | GGA | CTG | GTG | GGC | CCA | CGA | AAT | ACA | GAA | TAC | ACC | CTG | TTT | GAA | AGC | 1159 |
| Thr | Gly | Leu | Val | Gly | Pro | Arg | Asn | Thr | Glu | Tyr | Thr | Leu | Phe | Glu | Ser | |
| | | | | 315 | | | | | 320 | | | | | 325 | | |
| ATT | TCA | GGA | AAA | TCG | GCA | GTA | TTT | CAC | AGG | ATT | GAA | GGA | CTT | ACA | AAC | 1207 |
| Ile | Ser | Gly | Lys | Ser | Ala | Val | Phe | His | Arg | Ile | Glu | Gly | Leu | Thr | Asn | |
| | | | | 330 | | | | | 335 | | | | | 340 | | |

| | | | | | | | | | | | | | | | | |
|---|---|---|---|---|---|---|---|---|---|---|---|---|---|---|---|---|
| GAG | ACC | TAC | CGG | TTA | GGC | GTG | CAA | ATG | CAT | CCC | GGC | CAA | GAA | ATC | CAT | 1255 |
| Glu | Thr | Tyr | Arg | Leu | Gly | Val | Gln | Met | His | Pro | Gly | Gln | Glu | Ile | His | |
| | | 345 | | | | | 350 | | | | | 355 | | | | |
| AAC | TTC | ACC | CTG | ACT | GGT | CGC | AAT | CCA | CTG | GGG | CAG | GCA | CAG | TCA | GCA | 1303 |
| Asn | Phe | Thr | Leu | Thr | Gly | Arg | Asn | Pro | Leu | Gly | Gln | Ala | Gln | Ser | Ala | |
| | 360 | | | | | 365 | | | | | 370 | | | | | |
| GTG | GTC | ATC | AAT | GTG | ACT | GAG | AGA | GTT | GCT | CCT | CAT | GAT | CCG | ACT | TCG | 1351 |
| Val | Val | Ile | Asn | Val | Thr | Glu | Arg | Val | Ala | Pro | His | Asp | Pro | Thr | Ser | |
| 375 | | | | | 380 | | | | | 385 | | | | | 390 | |
| TTG | AAA | GTG | AAG | GAC | ATC | AAT | TCA | ACA | GTT | GTT | ACA | TTT | TCT | TGG | TAT | 1399 |
| Leu | Lys | Val | Lys | Asp | Ile | Asn | Ser | Thr | Val | Val | Thr | Phe | Ser | Trp | Tyr | |
| | | | | 395 | | | | | 400 | | | | | 405 | | |
| TTA | CCA | GGA | AAT | TTT | ACA | AAG | ATT | AAT | CTT | TTA | TGT | CAA | ATT | GAA | ATT | 1447 |
| Leu | Pro | Gly | Asn | Phe | Thr | Lys | Ile | Asn | Leu | Leu | Cys | Gln | Ile | Glu | Ile | |
| | | | 410 | | | | | 415 | | | | | 420 | | | |
| TGT | AAA | GCT | AAT | TCC | AAG | AAA | GAA | GTG | AGG | AAT | GCC | ACA | ATC | AGA | GGA | 1495 |
| Cys | Lys | Ala | Asn | Ser | Lys | Lys | Glu | Val | Arg | Asn | Ala | Thr | Ile | Arg | Gly | |
| | 425 | | | | | 430 | | | | | 435 | | | | | |
| GCC | GAG | GAT | TCA | ACT | TAC | CAT | GTT | GCT | GTA | GAC | AAA | TTA | AAT | CCA | TAC | 1543 |
| Ala | Glu | Asp | Ser | Thr | Tyr | His | Val | Ala | Val | Asp | Lys | Leu | Asn | Pro | Tyr | |
| | 440 | | | | | 445 | | | | | 450 | | | | | |
| ACT | GCA | TAC | ACT | TTC | CGG | GTT | CGT | TGT | TCT | TCC | AAG | ACT | TTC | TGG | AAG | 1591 |
| Thr | Ala | Tyr | Thr | Phe | Arg | Val | Arg | Cys | Ser | Ser | Lys | Thr | Phe | Trp | Lys | |
| 455 | | | | | 460 | | | | | 465 | | | | | 470 | |
| TGG | AGC | AGG | TGG | AGT | GAT | GAG | AAG | CGA | CAT | CTA | ACC | ACA | GAA | GCC | ACT | 1639 |
| Trp | Ser | Arg | Trp | Ser | Asp | Glu | Lys | Arg | His | Leu | Thr | Thr | Glu | Ala | Thr | |
| | | | | 475 | | | | | 480 | | | | | 485 | | |
| CCT | TCA | AAG | GGA | CCA | GAC | ACT | TGG | AGA | GAG | TGG | AGT | TCT | GAT | GGA | AAA | 1687 |
| Pro | Ser | Lys | Gly | Pro | Asp | Thr | Trp | Arg | Glu | Trp | Ser | Ser | Asp | Gly | Lys | |
| | | | 490 | | | | | 495 | | | | | 500 | | | |
| AAT | CTA | ATC | GTC | TAC | TGG | AAG | CCT | TTA | CCT | ATT | AAT | GAA | GCT | AAT | GGA | 1735 |
| Asn | Leu | Ile | Val | Tyr | Trp | Lys | Pro | Leu | Pro | Ile | Asn | Glu | Ala | Asn | Gly | |
| | | 505 | | | | | 510 | | | | | 515 | | | | |
| AAA | ATA | CTT | TCC | TAC | AAT | GTT | TCG | TGT | TCA | TTG | AAC | GAG | GAG | ACA | CAG | 1783 |
| Lys | Ile | Leu | Ser | Tyr | Asn | Val | Ser | Cys | Ser | Leu | Asn | Glu | Glu | Thr | Gln | |
| | 520 | | | | | 525 | | | | | 530 | | | | | |
| TCA | GTT | TTG | GAG | ATC | TTC | GAT | CCT | CAA | CAC | AGA | GCA | GAG | ATA | CAG | CTT | 1831 |
| Ser | Val | Leu | Glu | Ile | Phe | Asp | Pro | Gln | His | Arg | Ala | Glu | Ile | Gln | Leu | |
| 535 | | | | | 540 | | | | | 545 | | | | | 550 | |
| AGT | AAA | AAT | GAC | TAC | ATC | ATC | AGT | GTG | GTG | GCA | AGA | AAT | TCT | GCT | GGC | 1879 |
| Ser | Lys | Asn | Asp | Tyr | Ile | Ile | Ser | Val | Val | Ala | Arg | Asn | Ser | Ala | Gly | |
| | | | | 555 | | | | | 560 | | | | | 565 | | |
| TCA | TCA | CCA | CCT | TCG | AAA | ATA | GCT | AGT | ATG | GAA | ATC | CCA | AAT | GAC | GAC | 1927 |
| Ser | Ser | Pro | Pro | Ser | Lys | Ile | Ala | Ser | Met | Glu | Ile | Pro | Asn | Asp | Asp | |
| | | | 570 | | | | | 575 | | | | | 580 | | | |
| ATC | ACA | GTA | GAG | CAA | GCG | GTG | GGG | CTA | GGA | AAC | AGG | ATC | TTC | CTC | ACC | 1975 |
| Ile | Thr | Val | Glu | Gln | Ala | Val | Gly | Leu | Gly | Asn | Arg | Ile | Phe | Leu | Thr | |
| | | 585 | | | | | 590 | | | | | 595 | | | | |
| TGG | CGT | CAC | GAC | CCC | AAC | ATG | ACT | TGT | GAC | TAC | GTA | ATT | AAA | TGG | TGC | 2023 |
| Trp | Arg | His | Asp | Pro | Asn | Met | Thr | Cys | Asp | Tyr | Val | Ile | Lys | Trp | Cys | |
| | 600 | | | | | 605 | | | | | 610 | | | | | |
| AAC | TCA | TCT | CGG | TCT | GAG | CCC | TGC | CTC | CTG | GAC | TGG | AGA | AAG | GTT | CCT | 2071 |
| Asn | Ser | Ser | Arg | Ser | Glu | Pro | Cys | Leu | Leu | Asp | Trp | Arg | Lys | Val | Pro | |
| 615 | | | | | 620 | | | | | 625 | | | | | 630 | |
| TCA | AAC | AGC | ACG | GAG | ACT | GTC | ATA | GAG | TCT | GAT | CAG | TTT | CAG | CCA | GGA | 2119 |
| Ser | Asn | Ser | Thr | Glu | Thr | Val | Ile | Glu | Ser | Asp | Gln | Phe | Gln | Pro | Gly | |
| | | | | 635 | | | | | 640 | | | | | 645 | | |
| GTA | AGA | TAC | AAC | TTT | TAC | CTC | TAT | GGG | TGC | ACT | AAC | CAG | GGA | TAC | CAA | 2167 |
| Val | Arg | Tyr | Asn | Phe | Tyr | Leu | Tyr | Gly | Cys | Thr | Asn | Gln | Gly | Tyr | Gln | |
| | | | 650 | | | | | 655 | | | | | 660 | | | |

```
CTG TTA CGT TCC ATA ATT GGA TAC GTA GAA GAA CTG GAA GCT TAAAAACTTG    2219
Leu Leu Arg Ser Ile Ile Gly Tyr Val Glu Glu Leu Glu Ala
        665             670                 675

GAAATGTATC CAGGCCTAAC ACCAGAGAGG GGAGTATCCC TGAAGTCTGT TTGAGCGGTC    2279
ACTTAAAATA TGCGGCACAT GGGGGGCTGG AGAGATGGCA CCGACTGCTC TTCCAGAGGT    2339
CCTGAGTTCA ATTCCCAGCA ACCACATGGT GACTCACAAC CATCTGTAAT GGGGTCTGGT    2399
GCCCTCTTCT GGTGTGTCTG AAGAGAGCAA TGGTGGCATA CTCATATGTA TAAAATAAAT    2459
AAATAAATCT TTTTAAAAAA CCAAAAAAAA AAAAAAAA                            2498
```

(2) INFORMATION FOR SEQ ID NO:4:

(i) SEQUENCE CHARACTERISTICS:
        (A) LENGTH: 719 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Ala Tyr Ser Trp Trp Arg Gln Pro Ser Trp Met Val Asp Asn
-43             -40                 -35                 -30

Lys Arg Ser Arg Met Thr Pro Asn Leu Pro Trp Leu Leu Ser Ala Leu
        -25                 -20                 -15

Thr Leu Leu His Leu Thr Met His Ala Asn Gly Leu Lys Arg Gly Val
        -10              -5                   1                5

Gln Asp Leu Lys Cys Thr Thr Asn Met Arg Val Trp Asp Cys Thr
                10                  15                  20

Trp Pro Ala Pro Leu Gly Val Ser Pro Gly Thr Val Lys Asp Ile Cys
            25                  30                  35

Ile Lys Asp Arg Phe His Ser Cys His Pro Leu Glu Thr Thr Asn Val
        40                  45                  50

Lys Ile Pro Ala Leu Ser Pro Gly Asp His Glu Val Thr Ile Asn Tyr
        55                  60                  65

Leu Asn Gly Phe Gln Ser Lys Phe Thr Leu Asn Glu Lys Asp Val Ser
70                  75                  80                  85

Leu Ile Pro Glu Thr Pro Glu Ile Leu Asp Leu Ser Ala Asp Phe Phe
                90                  95                  100

Thr Ser Ser Leu Leu Leu Lys Trp Asn Asp Arg Gly Ser Ala Leu Pro
            105                 110                 115

His Pro Ser Asn Ala Thr Trp Glu Ile Lys Val Leu Gln Asn Pro Arg
        120                 125                 130

Thr Glu Pro Val Ala Leu Val Leu Leu Asn Thr Met Leu Ser Gly Lys
        135                 140                 145

Asp Thr Val Gln His Trp Asn Trp Thr Ser Asp Leu Pro Leu Gln Cys
150                 155                 160                 165

Ala Thr His Ser Val Ser Ile Arg Trp His Ile Asp Ser Pro His Phe
                170                 175                 180

Ser Gly Tyr Lys Glu Trp Ser Asp Trp Ser Pro Leu Lys Asn Ile Ser
            185                 190                 195

Trp Ile Arg Asn Thr Glu Thr Asn Val Phe Pro Gln Asp Lys Val Val
        200                 205                 210

Leu Ala Gly Ser Asn Met Thr Ile Cys Cys Met Ser Pro Thr Lys Val
        215                 220                 225

Leu Ser Gly Gln Ile Gly Asn Thr Leu Arg Pro Leu Ile His Leu Tyr
230                 235                 240                 245
```

```
Gly Gln Thr Val Ala Ile His Ile Leu Asn Ile Pro Val Ser Glu Asn
                250                 255                 260

Ser Gly Thr Asn Ile Ile Phe Ile Thr Asp Asp Val Tyr Gly Thr
                265                 270                 275

Val Val Phe Ala Gly Tyr Pro Pro Asp Val Pro Gln Lys Leu Ser Cys
                280                 285                 290

Glu Thr His Asp Leu Lys Glu Ile Ile Cys Ser Trp Asn Pro Gly Arg
        295                 300                 305

Ile Thr Gly Leu Val Gly Pro Arg Asn Thr Glu Tyr Thr Leu Phe Glu
310                 315                 320                 325

Ser Ile Ser Gly Lys Ser Ala Val Phe His Arg Ile Glu Gly Leu Thr
                330                 335                 340

Asn Glu Thr Tyr Arg Leu Gly Val Gln Met His Pro Gly Gln Glu Ile
                345                 350                 355

His Asn Phe Thr Leu Thr Gly Arg Asn Pro Leu Gly Gln Ala Gln Ser
        360                 365                 370

Ala Val Val Ile Asn Val Thr Glu Arg Val Ala Pro His Asp Pro Thr
        375                 380                 385

Ser Leu Lys Val Lys Asp Ile Asn Ser Thr Val Val Thr Phe Ser Trp
390                 395                 400                 405

Tyr Leu Pro Gly Asn Phe Thr Lys Ile Asn Leu Leu Cys Gln Ile Glu
                410                 415                 420

Ile Cys Lys Ala Asn Ser Lys Lys Glu Val Arg Asn Ala Thr Ile Arg
                425                 430                 435

Gly Ala Glu Asp Ser Thr Tyr His Val Ala Val Asp Lys Leu Asn Pro
        440                 445                 450

Tyr Thr Ala Tyr Thr Phe Arg Val Arg Cys Ser Ser Lys Thr Phe Trp
        455                 460                 465

Lys Trp Ser Arg Trp Ser Asp Glu Lys Arg His Leu Thr Thr Glu Ala
470                 475                 480                 485

Thr Pro Ser Lys Gly Pro Asp Thr Trp Arg Glu Trp Ser Ser Asp Gly
                490                 495                 500

Lys Asn Leu Ile Val Tyr Trp Lys Pro Leu Pro Ile Asn Glu Ala Asn
                505                 510                 515

Gly Lys Ile Leu Ser Tyr Asn Val Ser Cys Ser Leu Asn Glu Glu Thr
        520                 525                 530

Gln Ser Val Leu Glu Ile Phe Asp Pro Gln His Arg Ala Glu Ile Gln
        535                 540                 545

Leu Ser Lys Asn Asp Tyr Ile Ile Ser Val Val Ala Arg Asn Ser Ala
550                 555                 560                 565

Gly Ser Ser Pro Pro Ser Lys Ile Ala Ser Met Glu Ile Pro Asn Asp
                570                 575                 580

Asp Ile Thr Val Glu Gln Ala Val Gly Leu Gly Asn Arg Ile Phe Leu
                585                 590                 595

Thr Trp Arg His Asp Pro Asn Met Thr Cys Asp Tyr Val Ile Lys Trp
        600                 605                 610

Cys Asn Ser Ser Arg Ser Glu Pro Cys Leu Leu Asp Trp Arg Lys Val
        615                 620                 625

Pro Ser Asn Ser Thr Glu Thr Val Ile Glu Ser Asp Gln Phe Gln Pro
630                 635                 640                 645

Gly Val Arg Tyr Asn Phe Tyr Leu Tyr Gly Cys Thr Asn Gln Gly Tyr
                650                 655                 660

Gln Leu Leu Arg Ser Ile Ile Gly Tyr Val Glu Glu Leu Glu Ala
                665                 670                 675
```

( 2 ) INFORMATION FOR SEQ ID NO:5:

( i ) SEQUENCE CHARACTERISTICS:
        ( A ) LENGTH: 3591 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i i ) IMMEDIATE SOURCE:
        ( B ) CLONE: bulifr.65-gen ( i x ) FEATURE:
        ( A ) NAME/KEY: CDS
        ( B ) LOCATION: 179..3472

( i x ) FEATURE:
        ( A ) NAME/KEY: mat_peptide
        ( B ) LOCATION: 311..3469

( i x ) FEATURE:
        ( A ) NAME/KEY: sig_peptide
        ( B ) LOCATION: 179..310

( x i ) SEQUENCE DESCRIPTION: SEQ ID NO:5:

```
AGATCTTGGA ACGAGACGAC CTGCTCTCTC TCCCAGAACG TGTCTCTGCT GCAAGGCACC        60

GGGCCCTTTC GCTCTGCAGA ACTGCACTTG CAAGACCATT ATCAACTCCT AATCCCAGCT       120

CAGAAAGGGA GCCTCTGCGA CTCATTCATC GCCCTCCAGG ACTGACTGCA TTGCACAG         178
```

| ATG | ATG | GAT | ATT | TAC | GTA | TGT | TTG | AAA | CGA | CCA | TCC | TGG | ATG | GTG | GAC | 226 |
|-----|-----|-----|-----|-----|-----|-----|-----|-----|-----|-----|-----|-----|-----|-----|-----|-----|
| Met | Met | Asp | Ile | Tyr | Val | Cys | Leu | Lys | Arg | Pro | Ser | Trp | Met | Val | Asp | |
| -44 | | | | -40 | | | | | -35 | | | | | -30 | | |

| AAT | AAA | AGA | ATG | AGG | ACT | GCT | TCA | AAT | TTC | CAG | TGG | CTG | TTA | TCA | ACA | 274 |
|-----|-----|-----|-----|-----|-----|-----|-----|-----|-----|-----|-----|-----|-----|-----|-----|-----|
| Asn | Lys | Arg | Met | Arg | Thr | Ala | Ser | Asn | Phe | Gln | Trp | Leu | Leu | Ser | Thr | |
| | | | -25 | | | | | -20 | | | | | | -15 | | |

| TTT | ATT | CTT | CTA | TAT | CTA | ATG | AAT | CAA | GTA | AAT | AGC | CAG | AAA | AAG | GGG | 322 |
|-----|-----|-----|-----|-----|-----|-----|-----|-----|-----|-----|-----|-----|-----|-----|-----|-----|
| Phe | Ile | Leu | Leu | Tyr | Leu | Met | Asn | Gln | Val | Asn | Ser | Gln | Lys | Lys | Gly | |
| | | -10 | | | | | -5 | | | | | | 1 | | | |

| GCT | CCT | CAT | GAT | TTG | AAG | TGT | GTA | ACT | AAC | AAT | TTG | CAA | GTG | TGG | AAC | 370 |
|-----|-----|-----|-----|-----|-----|-----|-----|-----|-----|-----|-----|-----|-----|-----|-----|-----|
| Ala | Pro | His | Asp | Leu | Lys | Cys | Val | Thr | Asn | Asn | Leu | Gln | Val | Trp | Asn | |
| 5 | | | | | 10 | | | | | 15 | | | | | 20 | |

| TGT | TCT | TGG | AAA | GCA | CCC | TCT | GGA | ACA | GGC | CGT | GGT | ACT | GAT | TAT | GAA | 418 |
|-----|-----|-----|-----|-----|-----|-----|-----|-----|-----|-----|-----|-----|-----|-----|-----|-----|
| Cys | Ser | Trp | Lys | Ala | Pro | Ser | Gly | Thr | Gly | Arg | Gly | Thr | Asp | Tyr | Glu | |
| | | | | 25 | | | | | 30 | | | | | 35 | | |

| GTT | TGC | ATT | GAA | AAC | AGG | TCC | CGT | TCT | TGT | TAT | CAG | TTG | GAG | AAA | ACC | 466 |
|-----|-----|-----|-----|-----|-----|-----|-----|-----|-----|-----|-----|-----|-----|-----|-----|-----|
| Val | Cys | Ile | Glu | Asn | Arg | Ser | Arg | Ser | Cys | Tyr | Gln | Leu | Glu | Lys | Thr | |
| | | | 40 | | | | | 45 | | | | | 50 | | | |

| AGT | ATT | AAA | ATT | CCA | GCT | CTT | TCA | CAT | GGT | GAT | TAT | GAA | ATA | ACA | ATA | 514 |
|-----|-----|-----|-----|-----|-----|-----|-----|-----|-----|-----|-----|-----|-----|-----|-----|-----|
| Ser | Ile | Lys | Ile | Pro | Ala | Leu | Ser | His | Gly | Asp | Tyr | Glu | Ile | Thr | Ile | |
| | | 55 | | | | | 60 | | | | | 65 | | | | |

| AAT | TCT | CTA | CAT | GAT | TTT | GGA | AGT | TCT | ACA | AGT | AAA | TTC | ACA | CTA | AAT | 562 |
|-----|-----|-----|-----|-----|-----|-----|-----|-----|-----|-----|-----|-----|-----|-----|-----|-----|
| Asn | Ser | Leu | His | Asp | Phe | Gly | Ser | Ser | Thr | Ser | Lys | Phe | Thr | Leu | Asn | |
| | 70 | | | | | 75 | | | | | 80 | | | | | |

| GAA | CAA | AAC | GTT | TCC | TTA | ATT | CCA | GAT | ACT | CCA | GAG | ATC | TTG | AAT | TTG | 610 |
|-----|-----|-----|-----|-----|-----|-----|-----|-----|-----|-----|-----|-----|-----|-----|-----|-----|
| Glu | Gln | Asn | Val | Ser | Leu | Ile | Pro | Asp | Thr | Pro | Glu | Ile | Leu | Asn | Leu | |
| 85 | | | | | 90 | | | | | 95 | | | | | 100 | |

| TCT | GCT | GAT | TTC | TCA | ACC | TCT | ACA | TTA | TAC | CTA | AAG | TGG | AAC | GAC | AGG | 658 |
|-----|-----|-----|-----|-----|-----|-----|-----|-----|-----|-----|-----|-----|-----|-----|-----|-----|
| Ser | Ala | Asp | Phe | Ser | Thr | Ser | Thr | Leu | Tyr | Leu | Lys | Trp | Asn | Asp | Arg | |
| | | | | 105 | | | | | 110 | | | | | 115 | | |

```
GGT TCA GTT TTT CCA CAC CGC TCA AAT GTT ATC TGG GAA ATT AAA GTT          706
```

|  |  |  |  |  |  |  |  |  |  |  |  |  |  |  |  |
|---|---|---|---|---|---|---|---|---|---|---|---|---|---|---|---|
| Gly | Ser | Val | Phe<br>120 | Pro | His | Arg | Ser | Asn<br>125 | Val | Ile | Trp | Glu | Ile<br>130 | Lys | Val |

| CTA | CGT | AAA | GAG | AGT | ATG | GAG | CTC | GTA | AAA | TTA | GTG | ACC | CAC | AAC | ACA | 754 |
|---|---|---|---|---|---|---|---|---|---|---|---|---|---|---|---|---|
| Leu | Arg | Lys<br>135 | Glu | Ser | Met | Glu | Leu | Val<br>140 | Lys | Leu | Val | Thr<br>145 | His | Asn | Thr |  |

| ACT | CTG | AAT | GGC | AAA | GAT | ACA | CTT | CAT | CAC | TGG | AGT | TGG | GCC | TCA | GAT | 802 |
|---|---|---|---|---|---|---|---|---|---|---|---|---|---|---|---|---|
| Thr | Leu<br>150 | Asn | Gly | Lys | Asp | Thr | Leu<br>155 | His | His | Trp | Ser | Trp<br>160 | Ala | Ser | Asp |  |

| ATG | CCC | TTG | GAA | TGT | GCC | ATT | CAT | TTT | GTG | GAA | ATT | AGA | TGC | TAC | ATT | 850 |
|---|---|---|---|---|---|---|---|---|---|---|---|---|---|---|---|---|
| Met<br>165 | Pro | Leu | Glu | Cys | Ala<br>170 | Ile | His | Phe | Val | Glu<br>175 | Ile | Arg | Cys | Tyr | Ile<br>180 |  |

| GAC | AAT | CTT | CAT | TTT | TCT | GGT | CTC | GAA | GAG | TGG | AGT | GAC | TGG | AGC | CCT | 898 |
|---|---|---|---|---|---|---|---|---|---|---|---|---|---|---|---|---|
| Asp | Asn | Leu | His | Phe<br>185 | Ser | Gly | Leu | Glu | Glu<br>190 | Trp | Ser | Asp | Trp | Ser<br>195 | Pro |  |

| GTG | AAG | AAC | ATT | TCT | TGG | ATA | CCT | GAT | TCT | CAG | ACT | AAG | GTT | TTT | CCT | 946 |
|---|---|---|---|---|---|---|---|---|---|---|---|---|---|---|---|---|
| Val | Lys | Asn | Ile | Ser<br>200 | Trp | Ile | Pro | Asp | Ser<br>205 | Gln | Thr | Lys | Val<br>210 | Phe | Pro |  |

| CAA | GAT | AAA | GTG | ATA | CTT | GTA | GGC | TCA | GAC | ATA | ACA | TTT | TGT | TGT | GTG | 994 |
|---|---|---|---|---|---|---|---|---|---|---|---|---|---|---|---|---|
| Gln | Asp | Lys<br>215 | Val | Ile | Leu | Val | Gly<br>220 | Ser | Asp | Ile | Thr | Phe<br>225 | Cys | Cys | Val |  |

| AGT | CAA | GAA | AAA | GTG | TTA | TCA | GCA | CTG | ATT | GGC | CAT | ACA | AAC | TGC | CCC | 1042 |
|---|---|---|---|---|---|---|---|---|---|---|---|---|---|---|---|---|
| Ser | Gln | Glu | Lys<br>230 | Val | Leu | Ser | Ala | Leu<br>235 | Ile | Gly | His | Thr<br>240 | Asn | Cys | Pro |  |

| TTG | ATC | CAT | CTT | GAT | GGG | GAA | AAT | GTT | GCA | ATC | AAG | ATT | CGT | AAT | ATT | 1090 |
|---|---|---|---|---|---|---|---|---|---|---|---|---|---|---|---|---|
| Leu<br>245 | Ile | His | Leu | Asp | Gly<br>250 | Glu | Asn | Val | Ala | Ile<br>255 | Lys | Ile | Arg | Asn | Ile<br>260 |  |

| TCT | GTT | TCT | GCA | AGT | AGT | GGA | ACA | AAT | GTA | GTT | TTT | ACA | ACC | GAA | GAT | 1138 |
|---|---|---|---|---|---|---|---|---|---|---|---|---|---|---|---|---|
| Ser | Val | Ser | Ala | Ser<br>265 | Ser | Gly | Thr | Asn | Val<br>270 | Val | Phe | Thr | Thr | Glu<br>275 | Asp |  |

| AAC | ATA | TTT | GGA | ACC | GTT | ATT | TTT | GCT | GGA | TAT | CCA | CCA | GAT | ACT | CCT | 1186 |
|---|---|---|---|---|---|---|---|---|---|---|---|---|---|---|---|---|
| Asn | Ile | Phe | Gly<br>280 | Thr | Val | Ile | Phe | Ala<br>285 | Gly | Tyr | Pro | Pro | Asp<br>290 | Thr | Pro |  |

| CAA | CAA | CTG | AAT | TGT | GAG | ACA | CAT | GAT | TTA | AAA | GAA | ATT | ATA | TGT | AGT | 1234 |
|---|---|---|---|---|---|---|---|---|---|---|---|---|---|---|---|---|
| Gln | Gln | Leu<br>295 | Asn | Cys | Glu | Thr | His<br>300 | Asp | Leu | Lys | Glu | Ile<br>305 | Ile | Cys | Ser |  |

| TGG | AAT | CCA | GGA | AGG | GTG | ACA | GCG | TTG | GTG | GGC | CCA | CGT | GCT | ACA | AGC | 1282 |
|---|---|---|---|---|---|---|---|---|---|---|---|---|---|---|---|---|
| Trp | Asn<br>310 | Pro | Gly | Arg | Val | Thr<br>315 | Ala | Leu | Val | Gly | Pro<br>320 | Arg | Ala | Thr | Ser |  |

| TAC | ACT | TTA | GTT | GAA | AGT | TTT | TCA | GGA | AAA | TAT | GTT | AGA | CTT | AAA | AGA | 1330 |
|---|---|---|---|---|---|---|---|---|---|---|---|---|---|---|---|---|
| Tyr<br>325 | Thr | Leu | Val | Glu | Ser<br>330 | Phe | Ser | Gly | Lys | Tyr<br>335 | Val | Arg | Leu | Lys | Arg<br>340 |  |

| GCT | GAA | GCA | CCT | ACA | AAC | GAA | AGC | TAT | CAA | TTA | TTA | TTT | CAA | ATG | CTT | 1378 |
|---|---|---|---|---|---|---|---|---|---|---|---|---|---|---|---|---|
| Ala | Glu | Ala | Pro | Thr<br>345 | Asn | Glu | Ser | Tyr | Gln<br>350 | Leu | Leu | Phe | Gln | Met<br>355 | Leu |  |

| CCA | AAT | CAA | GAA | ATA | TAT | AAT | TTT | ACT | TTG | AAT | GCT | CAC | AAT | CCG | CTG | 1426 |
|---|---|---|---|---|---|---|---|---|---|---|---|---|---|---|---|---|
| Pro | Asn | Gln | Glu<br>360 | Ile | Tyr | Asn | Phe | Thr<br>365 | Leu | Asn | Ala | His | Asn<br>370 | Pro | Leu |  |

| GGT | CGA | TCA | CAA | TCA | ACA | ATT | TTA | GTT | AAT | ATA | ACT | GAA | AAA | GTT | TAT | 1474 |
|---|---|---|---|---|---|---|---|---|---|---|---|---|---|---|---|---|
| Gly | Arg | Ser<br>375 | Gln | Ser | Thr | Ile | Leu<br>380 | Val | Asn | Ile | Thr | Glu<br>385 | Lys | Val | Tyr |  |

| CCC | CAT | ACT | CCT | ACT | TCA | TTC | AAA | GTG | AAG | GAT | ATT | AAT | TCA | ACA | GCT | 1522 |
|---|---|---|---|---|---|---|---|---|---|---|---|---|---|---|---|---|
| Pro | His<br>390 | Thr | Pro | Thr | Ser | Phe<br>395 | Lys | Val | Lys | Asp | Ile<br>400 | Asn | Ser | Thr | Ala |  |

| GTT | AAA | CTT | TCT | TGG | CAT | TTA | CCA | GGC | AAC | TTT | GCA | AAG | ATT | AAT | TTT | 1570 |
|---|---|---|---|---|---|---|---|---|---|---|---|---|---|---|---|---|
| Val<br>405 | Lys | Leu | Ser | Trp | His<br>410 | Leu | Pro | Gly | Asn | Phe<br>415 | Ala | Lys | Ile | Asn | Phe<br>420 |  |

| TTA | TGT | GAA | ATT | GAA | ATT | AAG | AAA | TCT | AAT | TCA | GTA | CAA | GAG | CAG | CGG | 1618 |
|---|---|---|---|---|---|---|---|---|---|---|---|---|---|---|---|---|
| Leu | Cys | Glu | Ile | Glu<br>425 | Ile | Lys | Lys | Ser | Asn<br>430 | Ser | Val | Gln | Glu | Gln<br>435 | Arg |  |

| AAT | GTC | ACA | ATC | AAA | GGA | GTA | GAA | AAT | TCA | AGT | TAT | CTT | GTT | GCT | CTG | 1666 |
|---|---|---|---|---|---|---|---|---|---|---|---|---|---|---|---|---|

```
                Asn  Val  Thr  Ile  Lys  Gly  Val  Glu  Asn  Ser  Ser  Tyr  Leu  Val  Ala  Leu
                               440                      445                      450

GAC  AAG  TTA  AAT  CCA  TAC  ACT  CTA  TAT  ACT  TTT  CGG  ATT  CGT  TGT  TCT                    1714
Asp  Lys  Leu  Asn  Pro  Tyr  Thr  Leu  Tyr  Thr  Phe  Arg  Ile  Arg  Cys  Ser
          455                      460                      465

ACT  GAA  ACT  TTC  TGG  AAA  TGG  AGC  AAA  TGG  AGC  AAT  AAA  AAA  CAA  CAT                    1762
Thr  Glu  Thr  Phe  Trp  Lys  Trp  Ser  Lys  Trp  Ser  Asn  Lys  Lys  Gln  His
          470                      475                      480

TTA  ACA  ACA  GAA  GCC  AGT  CCT  TCA  AAG  GGG  CCT  GAT  ACT  TGG  AGA  GAG                    1810
Leu  Thr  Thr  Glu  Ala  Ser  Pro  Ser  Lys  Gly  Pro  Asp  Thr  Trp  Arg  Glu
485                           490                      495                      500

TGG  AGT  TCT  GAT  GGA  AAA  AAT  TTA  ATA  ATC  TAT  TGG  AAG  CCT  TTA  CCC                    1858
Trp  Ser  Ser  Asp  Gly  Lys  Asn  Leu  Ile  Ile  Tyr  Trp  Lys  Pro  Leu  Pro
                    505                      510                      515

ATT  AAT  GAA  GCT  AAT  GGA  AAA  ATA  CTT  TCC  TAC  AAT  GTA  TCG  TGT  TCA                    1906
Ile  Asn  Glu  Ala  Asn  Gly  Lys  Ile  Leu  Ser  Tyr  Asn  Val  Ser  Cys  Ser
               520                      525                      530

TCA  GAT  GAG  GAA  ACA  CAG  TCC  CTT  TCT  GAA  ATC  CCT  GAT  CCT  CAG  CAC                    1954
Ser  Asp  Glu  Glu  Thr  Gln  Ser  Leu  Ser  Glu  Ile  Pro  Asp  Pro  Gln  His
          535                      540                      545

AAA  GCA  GAG  ATA  CGA  CTT  GAT  AAG  AAT  GAC  TAC  ATC  ATC  AGC  GTA  GTG                    2002
Lys  Ala  Glu  Ile  Arg  Leu  Asp  Lys  Asn  Asp  Tyr  Ile  Ile  Ser  Val  Val
550                           555                      560

GCT  AAA  AAT  TCT  GTG  GGC  TCA  TCA  CCA  CCT  TCC  AAA  ATA  GCG  AGT  ATG                    2050
Ala  Lys  Asn  Ser  Val  Gly  Ser  Ser  Pro  Pro  Ser  Lys  Ile  Ala  Ser  Met
565                           570                      575                      580

GAA  ATT  CCA  AAT  GAT  GAT  CTC  AAA  ATA  GAA  CAA  GTT  GTT  GGG  ATG  GGA                    2098
Glu  Ile  Pro  Asn  Asp  Asp  Leu  Lys  Ile  Glu  Gln  Val  Val  Gly  Met  Gly
                    585                      590                      595

AAG  GGG  ATT  CTC  CTC  ACC  TGG  CAT  TAC  GAC  CCC  AAC  ATG  ACT  TGC  GAC                    2146
Lys  Gly  Ile  Leu  Leu  Thr  Trp  His  Tyr  Asp  Pro  Asn  Met  Thr  Cys  Asp
               600                      605                      610

TAC  GTC  ATT  AAG  TGG  TGT  AAC  TCG  TCT  CGG  TCG  GAA  CCA  TGC  CTT  ATG                    2194
Tyr  Val  Ile  Lys  Trp  Cys  Asn  Ser  Ser  Arg  Ser  Glu  Pro  Cys  Leu  Met
          615                      620                      625

GAC  TGG  AGA  AAA  GTT  CCC  TCA  AAC  AGC  ACT  GAA  ACT  GTA  ATA  GAA  TCT                    2242
Asp  Trp  Arg  Lys  Val  Pro  Ser  Asn  Ser  Thr  Glu  Thr  Val  Ile  Glu  Ser
          630                      635                      640

GAT  GAG  TTT  CGA  CCA  GGT  ATA  AGA  TAT  AAT  TTT  TTC  CTG  TAT  GGA  TGC                    2290
Asp  Glu  Phe  Arg  Pro  Gly  Ile  Arg  Tyr  Asn  Phe  Phe  Leu  Tyr  Gly  Cys
645                           650                      655                      660

AGA  AAT  CAA  GGA  TAT  CAA  TTA  TTA  CGC  TCC  ATG  ATT  GGA  TAT  ATA  GAA                    2338
Arg  Asn  Gln  Gly  Tyr  Gln  Leu  Leu  Arg  Ser  Met  Ile  Gly  Tyr  Ile  Glu
                    665                      670                      675

GAA  TTG  GCT  CCC  ATT  GTT  GCA  CCA  AAT  TTT  ACT  GTT  GAG  GAT  ACT  TCT                    2386
Glu  Leu  Ala  Pro  Ile  Val  Ala  Pro  Asn  Phe  Thr  Val  Glu  Asp  Thr  Ser
               680                      685                      690

GCA  GAT  TCG  ATA  TTA  GTA  AAA  TGG  GAA  GAC  ATT  CCT  GTG  GAA  GAA  CTT                    2434
Ala  Asp  Ser  Ile  Leu  Val  Lys  Trp  Glu  Asp  Ile  Pro  Val  Glu  Glu  Leu
          695                      700                      705

AGA  GGC  TTT  TTA  AGA  GGA  TAT  TTG  TTT  TAC  TTT  GGA  AAA  GGA  GAA  AGA                    2482
Arg  Gly  Phe  Leu  Arg  Gly  Tyr  Leu  Phe  Tyr  Phe  Gly  Lys  Gly  Glu  Arg
          710                      715                      720

GAC  ACA  TCT  AAG  ATG  AGG  GTT  TTA  GAA  TCA  GGT  CGT  TCT  GAC  ATA  AAA                    2530
Asp  Thr  Ser  Lys  Met  Arg  Val  Leu  Glu  Ser  Gly  Arg  Ser  Asp  Ile  Lys
725                           730                      735                      740

GTT  AAG  AAT  ATT  ACT  GAC  ATA  TCC  CAG  AAG  ACA  CTG  AGA  ATT  GCT  GAT                    2578
Val  Lys  Asn  Ile  Thr  Asp  Ile  Ser  Gln  Lys  Thr  Leu  Arg  Ile  Ala  Asp
                    745                      750                      755

CTT  CAA  GGT  AAA  ACA  AGT  TAC  CAC  CTG  GTC  TTG  CGA  GCC  TAT  ACA  GAT                    2626
```

```
Leu Gln Gly Lys Thr Ser Tyr His Leu Val Leu Arg Ala Tyr Thr Asp
            760             765                 770

GGT GGA GTG GGC CCG GAG AAG AGT ATG TAT GTG GTG ACA AAG GAA AAT      2674
Gly Gly Val Gly Pro Glu Lys Ser Met Tyr Val Val Thr Lys Glu Asn
            775             780                 785

TCT GTG GGA TTA ATT ATT GCC ATT CTC ATC CCA GTG GCA GTG GCT GTC      2722
Ser Val Gly Leu Ile Ile Ala Ile Leu Ile Pro Val Ala Val Ala Val
            790             795                 800

ATT GTT GGA GTG GTG ACA AGT ATC CTT TGC TAT CGG AAA CGA GAA TGG      2770
Ile Val Gly Val Val Thr Ser Ile Leu Cys Tyr Arg Lys Arg Glu Trp
805             810             815                 820

ATT AAA GAA ACC TTC TAC CCT GAT ATT CCA AAT CCA GAA AAC TGT AAA      2818
Ile Lys Glu Thr Phe Tyr Pro Asp Ile Pro Asn Pro Glu Asn Cys Lys
                825             830                 835

GCA TTA CAG TTT CAA AAG AGT GTC TGT GAG GGA AGC AGT GCT CTT AAA      2866
Ala Leu Gln Phe Gln Lys Ser Val Cys Glu Gly Ser Ser Ala Leu Lys
                840             845                 850

ACA TTG GAA ATG AAT CCT TGT ACC CCA AAT AAT GTT GAG GTT CTG GAA      2914
Thr Leu Glu Met Asn Pro Cys Thr Pro Asn Asn Val Glu Val Leu Glu
            855             860                 865

ACT CGA TCA GCA TTT CCT AAA ATA GAA GAT ACA GAA ATA ATT TCC CCA      2962
Thr Arg Ser Ala Phe Pro Lys Ile Glu Asp Thr Glu Ile Ile Ser Pro
870             875             880

GTA GCT GAG CGT CCT GAA GAT CGC TCT GAT GCA GAG CCT GAA AAC CAT      3010
Val Ala Glu Arg Pro Glu Asp Arg Ser Asp Ala Glu Pro Glu Asn His
885             890             895                 900

GTG GTT GTG TCC TAT TGT CCA CCC ATC ATT GAG GAA GAA ATA CCA AAC      3058
Val Val Val Ser Tyr Cys Pro Pro Ile Ile Glu Glu Glu Ile Pro Asn
            905             910                 915

CCA GCC GCA GAT GAA GCT GGA GGG ACT GCA CAG GTT ATT TAC ATT GAT      3106
Pro Ala Ala Asp Glu Ala Gly Gly Thr Ala Gln Val Ile Tyr Ile Asp
            920             925                 930

GTT CAG TCG ATG TAT CAG CCT CAA GCA AAA CCA GAA GAA GAA CAA GAA      3154
Val Gln Ser Met Tyr Gln Pro Gln Ala Lys Pro Glu Glu Glu Gln Glu
            935             940                 945

AAT GAC CCT GTA GGA GGG GCA GGC TAT AAG CCA CAG ATG CAC CTC CCC      3202
Asn Asp Pro Val Gly Gly Ala Gly Tyr Lys Pro Gln Met His Leu Pro
950             955                 960

ATT AAT TCT ACT GTG GAA GAT ATA GCT GCA GAA GAG GAC TTA GAT AAA      3250
Ile Asn Ser Thr Val Glu Asp Ile Ala Ala Glu Glu Asp Leu Asp Lys
965             970             975                 980

ACT GCG GGT TAC AGA CCT CAG GCC AAT GTA AAT ACA TGG AAT TTA GTG      3298
Thr Ala Gly Tyr Arg Pro Gln Ala Asn Val Asn Thr Trp Asn Leu Val
            985             990                 995

TCT CCA GAC TCT CCT AGA TCC ATA GAC AGC AAC AGT GAG ATT GTC TCA      3346
Ser Pro Asp Ser Pro Arg Ser Ile Asp Ser Asn Ser Glu Ile Val Ser
            1000            1005                1010

TTT GGA AGT CCA TGC TCC ATT AAT TCC CGA CAA TTT TTG ATT CCT CCT      3394
Phe Gly Ser Pro Cys Ser Ile Asn Ser Arg Gln Phe Leu Ile Pro Pro
            1015            1020                1025

AAA GAT GAA GAC TCT CCT AAA TCT AAT GGA GGA GGG TGG TCC TTT ACA      3442
Lys Asp Glu Asp Ser Pro Lys Ser Asn Gly Gly Gly Trp Ser Phe Thr
            1030            1035                1040

AAC TTT TTT CAG AAC AAA CCA AAC GAT TAACAGTGTC ACCGTGTCAC            3489
Asn Phe Phe Gln Asn Lys Pro Asn Asp
1045            1050

TTCAGTCAGC CATCTCAATA AGCTCTTACT GCTAGTGTTG CTACATCAGC ACTGGGCATT   3549

CTTGGAGGGA TCCTGTGAAG TATTGTTAGG AGGTGAACTT CA                      3591
```

( 2 ) INFORMATION FOR SEQ ID NO:6:

( i ) SEQUENCE CHARACTERISTICS:
        ( A ) LENGTH: 1097 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met<br>-44 | Met | Asp | Ile | Tyr<br>-40 | Val | Cys | Leu | Lys | Arg<br>-35 | Pro | Ser | Trp | Met | Val<br>-30 | Asp |
|---|---|---|---|---|---|---|---|---|---|---|---|---|---|---|---|
| Asn | Lys | Arg | Met<br>-25 | Arg | Thr | Ala | Ser | Asn<br>-20 | Phe | Gln | Trp | Leu | Leu<br>-15 | Ser | Thr |
| Phe | Ile | Leu | Leu<br>-10 | Tyr | Leu | Met | Asn | Gln<br>-5 | Val | Asn | Ser | Gln | Lys<br>1 | Lys | Gly |
| Ala<br>5 | Pro | His | Asp | Leu | Lys<br>10 | Cys | Val | Thr | Asn | Asn<br>15 | Leu | Gln | Val | Trp | Asn<br>20 |
| Cys | Ser | Trp | Lys | Ala<br>25 | Pro | Ser | Gly | Thr | Gly<br>30 | Arg | Gly | Thr | Asp | Tyr<br>35 | Glu |
| Val | Cys | Ile | Glu<br>40 | Asn | Arg | Ser | Arg | Ser<br>45 | Cys | Tyr | Gln | Leu | Glu<br>50 | Lys | Thr |
| Ser | Ile | Lys<br>55 | Ile | Pro | Ala | Leu | Ser<br>60 | His | Gly | Asp | Tyr | Glu<br>65 | Ile | Thr | Ile |
| Asn | Ser<br>70 | Leu | His | Asp | Phe | Gly<br>75 | Ser | Ser | Thr | Ser | Lys<br>80 | Phe | Thr | Leu | Asn |
| Glu<br>85 | Gln | Asn | Val | Ser | Leu<br>90 | Ile | Pro | Asp | Thr | Pro<br>95 | Glu | Ile | Leu | Asn | Leu<br>100 |
| Ser | Ala | Asp | Phe | Ser<br>105 | Thr | Ser | Thr | Leu | Tyr<br>110 | Leu | Lys | Trp | Asn | Asp<br>115 | Arg |
| Gly | Ser | Val | Phe<br>120 | Pro | His | Arg | Ser | Asn<br>125 | Val | Ile | Trp | Glu | Ile<br>130 | Lys | Val |
| Leu | Arg | Lys<br>135 | Glu | Ser | Met | Glu | Leu<br>140 | Val | Lys | Leu | Val | Thr<br>145 | His | Asn | Thr |
| Thr | Leu<br>150 | Asn | Gly | Lys | Asp | Thr<br>155 | Leu | His | His | Trp | Ser<br>160 | Trp | Ala | Ser | Asp |
| Met<br>165 | Pro | Leu | Glu | Cys | Ala<br>170 | Ile | His | Phe | Val | Glu<br>175 | Ile | Arg | Cys | Tyr | Ile<br>180 |
| Asp | Asn | Leu | His | Phe<br>185 | Ser | Gly | Leu | Glu | Glu<br>190 | Trp | Ser | Asp | Trp | Ser<br>195 | Pro |
| Val | Lys | Asn | Ile<br>200 | Ser | Trp | Ile | Pro | Asp<br>205 | Ser | Gln | Thr | Lys | Val<br>210 | Phe | Pro |
| Gln | Asp | Lys<br>215 | Val | Ile | Leu | Val | Gly<br>220 | Ser | Asp | Ile | Thr | Phe<br>225 | Cys | Cys | Val |
| Ser | Gln<br>230 | Glu | Lys | Val | Leu | Ser<br>235 | Ala | Leu | Ile | Gly | His<br>240 | Thr | Asn | Cys | Pro |
| Leu<br>245 | Ile | His | Leu | Asp | Gly<br>250 | Glu | Asn | Val | Ala | Ile<br>255 | Lys | Ile | Arg | Asn | Ile<br>260 |
| Ser | Val | Ser | Ala | Ser<br>265 | Ser | Gly | Thr | Asn | Val<br>270 | Val | Phe | Thr | Thr | Glu<br>275 | Asp |
| Asn | Ile | Phe | Gly<br>280 | Thr | Val | Ile | Phe | Ala<br>285 | Gly | Tyr | Pro | Pro | Asp<br>290 | Thr | Pro |
| Gln | Gln | Leu | Asn<br>295 | Cys | Glu | Thr | His | Asp<br>300 | Leu | Lys | Glu | Ile | Ile<br>305 | Cys | Ser |
| Trp | Asn<br>310 | Pro | Gly | Arg | Val | Thr<br>315 | Ala | Leu | Val | Gly | Pro<br>320 | Arg | Ala | Thr | Ser |

```
Tyr  Thr  Leu  Val  Glu  Ser  Phe  Ser  Gly  Lys  Tyr  Val  Arg  Leu  Lys  Arg
325                 330                      335                           340

Ala  Glu  Ala  Pro  Thr  Asn  Glu  Ser  Tyr  Gln  Leu  Leu  Phe  Gln  Met  Leu
                    345                 350                      355

Pro  Asn  Gln  Glu  Ile  Tyr  Asn  Phe  Thr  Leu  Asn  Ala  His  Asn  Pro  Leu
               360                 365                      370

Gly  Arg  Ser  Gln  Ser  Thr  Ile  Leu  Val  Asn  Ile  Thr  Glu  Lys  Val  Tyr
          375                      380                 385

Pro  His  Thr  Pro  Thr  Ser  Phe  Lys  Val  Lys  Asp  Ile  Asn  Ser  Thr  Ala
     390                      395                 400

Val  Lys  Leu  Ser  Trp  His  Leu  Pro  Gly  Asn  Phe  Ala  Lys  Ile  Asn  Phe
405                      410                 415                           420

Leu  Cys  Glu  Ile  Glu  Ile  Lys  Lys  Ser  Asn  Ser  Val  Gln  Glu  Gln  Arg
               425                      430                           435

Asn  Val  Thr  Ile  Lys  Gly  Val  Glu  Asn  Ser  Ser  Tyr  Leu  Val  Ala  Leu
               440                 445                      450

Asp  Lys  Leu  Asn  Pro  Tyr  Thr  Leu  Tyr  Thr  Phe  Arg  Ile  Arg  Cys  Ser
          455                      460                 465

Thr  Glu  Thr  Phe  Trp  Lys  Trp  Ser  Lys  Trp  Ser  Asn  Lys  Lys  Gln  His
     470                      475                      480

Leu  Thr  Thr  Glu  Ala  Ser  Pro  Ser  Lys  Gly  Pro  Asp  Thr  Trp  Arg  Glu
485                      490                 495                           500

Trp  Ser  Ser  Asp  Gly  Lys  Asn  Leu  Ile  Ile  Tyr  Trp  Lys  Pro  Leu  Pro
               505                      510                      515

Ile  Asn  Glu  Ala  Asn  Gly  Lys  Ile  Leu  Ser  Tyr  Asn  Val  Ser  Cys  Ser
               520                 525                      530

Ser  Asp  Glu  Glu  Thr  Gln  Ser  Leu  Ser  Glu  Ile  Pro  Asp  Pro  Gln  His
          535                      540                 545

Lys  Ala  Glu  Ile  Arg  Leu  Asp  Lys  Asn  Asp  Tyr  Ile  Ile  Ser  Val  Val
550                      555                      560

Ala  Lys  Asn  Ser  Val  Gly  Ser  Ser  Pro  Pro  Ser  Lys  Ile  Ala  Ser  Met
565                      570                      575                      580

Glu  Ile  Pro  Asn  Asp  Asp  Leu  Lys  Ile  Glu  Gln  Val  Val  Gly  Met  Gly
                    585                 590                      595

Lys  Gly  Ile  Leu  Leu  Thr  Trp  His  Tyr  Asp  Pro  Asn  Met  Thr  Cys  Asp
               600                 605                      610

Tyr  Val  Ile  Lys  Trp  Cys  Asn  Ser  Arg  Ser  Glu  Pro  Cys  Leu  Met
          615                 620                      625

Asp  Trp  Arg  Lys  Val  Pro  Ser  Asn  Ser  Thr  Glu  Thr  Val  Ile  Glu  Ser
     630                      635                 640

Asp  Glu  Phe  Arg  Pro  Gly  Ile  Arg  Tyr  Asn  Phe  Phe  Leu  Tyr  Gly  Cys
645                      650                      655                      660

Arg  Asn  Gln  Gly  Tyr  Gln  Leu  Leu  Arg  Ser  Met  Ile  Gly  Tyr  Ile  Glu
               665                      670                      675

Glu  Leu  Ala  Pro  Ile  Val  Ala  Pro  Asn  Phe  Thr  Val  Glu  Asp  Thr  Ser
               680                      685                 690

Ala  Asp  Ser  Ile  Leu  Val  Lys  Trp  Glu  Asp  Ile  Pro  Val  Glu  Glu  Leu
          695                      700                 705

Arg  Gly  Phe  Leu  Arg  Gly  Tyr  Leu  Phe  Tyr  Phe  Gly  Lys  Gly  Glu  Arg
     710                      715                 720

Asp  Thr  Ser  Lys  Met  Arg  Val  Leu  Glu  Ser  Gly  Arg  Ser  Asp  Ile  Lys
725                      730                      735                      740

Val  Lys  Asn  Ile  Thr  Asp  Ile  Ser  Gln  Lys  Thr  Leu  Arg  Ile  Ala  Asp
               745                      750                      755
```

| | | | | | | | | | | | | | |
|---|---|---|---|---|---|---|---|---|---|---|---|---|---|
| Leu | Gln | Gly | Lys 760 | Thr | Ser | Tyr | His 765 | Leu | Val | Leu | Arg | Ala | Thr 770 | Asp |
| Gly | Gly | Val 775 | Gly | Pro | Glu | Lys | Ser 780 | Met | Tyr | Val | Val | Thr 785 | Lys | Glu | Asn |
| Ser | Val 790 | Gly | Leu | Ile | Ile | Ala 795 | Ile | Leu | Ile | Pro | Val 800 | Ala | Val | Ala | Val |
| Ile 805 | Val | Gly | Val | Val | Thr 810 | Ser | Ile | Leu | Cys | Tyr 815 | Arg | Lys | Arg | Glu | Trp 820 |
| Ile | Lys | Glu | Thr | Phe 825 | Tyr | Pro | Asp | Ile | Pro 830 | Asn | Pro | Glu | Asn | Cys 835 | Lys |
| Ala | Leu | Gln | Phe 840 | Gln | Lys | Ser | Val | Cys 845 | Glu | Gly | Ser | Ser | Ala 850 | Leu | Lys |
| Thr | Leu | Glu 855 | Met | Asn | Pro | Cys | Thr 860 | Pro | Asn | Asn | Val | Glu 865 | Val | Leu | Glu |
| Thr | Arg 870 | Ser | Ala | Phe | Pro | Lys 875 | Ile | Glu | Asp | Thr | Glu 880 | Ile | Ile | Ser | Pro |
| Val 885 | Ala | Glu | Arg | Pro | Glu 890 | Asp | Arg | Ser | Asp | Ala 895 | Glu | Pro | Glu | Asn | His 900 |
| Val | Val | Val | Ser | Tyr 905 | Cys | Pro | Pro | Ile | Ile 910 | Glu | Glu | Glu | Ile | Pro 915 | Asn |
| Pro | Ala | Ala | Asp 920 | Glu | Ala | Gly | Gly | Thr 925 | Ala | Gln | Val | Ile | Tyr 930 | Ile | Asp |
| Val | Gln | Ser 935 | Met | Tyr | Gln | Pro | Gln 940 | Ala | Lys | Pro | Glu | Glu 945 | Glu | Gln | Glu |
| Asn | Asp 950 | Pro | Val | Gly | Gly | Ala 955 | Gly | Tyr | Lys | Pro | Gln 960 | Met | His | Leu | Pro |
| Ile 965 | Asn | Ser | Thr | Val | Glu 970 | Asp | Ile | Ala | Ala | Glu 975 | Glu | Asp | Leu | Asp | Lys 980 |
| Thr | Ala | Gly | Tyr | Arg 985 | Pro | Gln | Ala | Asn | Val 990 | Asn | Thr | Trp | Asn | Leu 995 | Val |
| Ser | Pro | Asp | Ser 1000 | Pro | Arg | Ser | Ile | Asp 1005 | Ser | Asn | Ser | Glu | Ile 1010 | Val | Ser |
| Phe | Gly | Ser 1015 | Pro | Cys | Ser | Ile | Asn 1020 | Ser | Arg | Gln | Phe | Leu 1025 | Ile | Pro | Pro |
| Lys | Asp 1030 | Glu | Asp | Ser | Pro | Lys 1035 | Ser | Asn | Gly | Gly | Gly 1040 | Trp | Ser | Phe | Thr |
| Asn 1045 | Phe | Phe | Gln | Asn | Lys 1050 | Pro | Asn | Asp | | | | | | | |

( 2 ) INFORMATION FOR SEQ ID NO:7:

( i ) SEQUENCE CHARACTERISTICS:
        ( A ) LENGTH: 745 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( v i i ) IMMEDIATE SOURCE:
        ( B ) CLONE: hIgG1Fc ( i x ) FEATURE:
        ( A ) NAME/KEY: CDS
        ( B ) LOCATION: 2..739

( x i ) SEQUENCE DESCRIPTION: SEQ ID NO:7:

|   |     |     |     |     |     |     |     |     |     |     |     |     |     |     |     |     |
|---|-----|-----|-----|-----|-----|-----|-----|-----|-----|-----|-----|-----|-----|-----|-----|-----|
| G | GTA | CCG | CTA | GCG | TCG | ACA | GGC | CTA | GGA | TAT | CGA | TAC | GTA | GAG | CCC | 46 |
|   | Val | Pro | Leu | Ala | Ser | Thr | Gly | Leu | Gly | Tyr | Arg | Tyr | Val | Glu | Pro |    |
|   | 1   |     |     |     | 5   |     |     |     |     | 10  |     |     |     |     | 15  |    |

| AGA | TCT | TGT | GAC | AAA | ACT | CAC | ACA | TGC | CCA | CCG | TGC | CCA | GCA | CCT | GAA | 94 |
|-----|-----|-----|-----|-----|-----|-----|-----|-----|-----|-----|-----|-----|-----|-----|-----|----|
| Arg | Ser | Cys | Asp | Lys | Thr | His | Thr | Cys | Pro | Pro | Cys | Pro | Ala | Pro | Glu |    |
|     |     |     |     | 20  |     |     |     |     | 25  |     |     |     |     | 30  |     |    |

| CTC | CTG | GGG | GGA | CCG | TCA | GTC | TTC | CTC | TTC | CCC | CCA | AAA | CCC | AAG | GAC | 142 |
|-----|-----|-----|-----|-----|-----|-----|-----|-----|-----|-----|-----|-----|-----|-----|-----|-----|
| Leu | Leu | Gly | Gly | Pro | Ser | Val | Phe | Leu | Phe | Pro | Pro | Lys | Pro | Lys | Asp |     |
|     |     |     | 35  |     |     |     |     | 40  |     |     |     |     | 45  |     |     |     |

| ACC | CTC | ATG | ATC | TCC | CGG | ACC | CCT | GAG | GTC | ACA | TGC | GTG | GTG | GTG | GAC | 190 |
|-----|-----|-----|-----|-----|-----|-----|-----|-----|-----|-----|-----|-----|-----|-----|-----|-----|
| Thr | Leu | Met | Ile | Ser | Arg | Thr | Pro | Glu | Val | Thr | Cys | Val | Val | Val | Asp |     |
|     |     |     | 50  |     |     |     |     | 55  |     |     |     |     | 60  |     |     |     |

| GTG | AGC | CAC | GAA | GAC | CCT | GAG | GTC | AAG | TTC | AAC | TGG | TAC | GTG | GAC | GGC | 238 |
|-----|-----|-----|-----|-----|-----|-----|-----|-----|-----|-----|-----|-----|-----|-----|-----|-----|
| Val | Ser | His | Glu | Asp | Pro | Glu | Val | Lys | Phe | Asn | Trp | Tyr | Val | Asp | Gly |     |
|     | 65  |     |     |     |     | 70  |     |     |     |     | 75  |     |     |     |     |     |

| GTG | GAG | GTG | CAT | AAT | GCC | AAG | ACA | AAG | CCG | CGG | GAG | GAG | CAG | TAC | AAC | 286 |
|-----|-----|-----|-----|-----|-----|-----|-----|-----|-----|-----|-----|-----|-----|-----|-----|-----|
| Val | Glu | Val | His | Asn | Ala | Lys | Thr | Lys | Pro | Arg | Glu | Glu | Gln | Tyr | Asn |     |
| 80  |     |     |     |     | 85  |     |     |     |     | 90  |     |     |     |     | 95  |     |

| AGC | ACG | TAC | CGG | GTG | GTC | AGC | GTC | CTC | ACC | GTC | CTG | CAC | CAG | GAC | TGG | 334 |
|-----|-----|-----|-----|-----|-----|-----|-----|-----|-----|-----|-----|-----|-----|-----|-----|-----|
| Ser | Thr | Tyr | Arg | Val | Val | Ser | Val | Leu | Thr | Val | Leu | His | Gln | Asp | Trp |     |
|     |     |     |     | 100 |     |     |     |     | 105 |     |     |     |     | 110 |     |     |

| CTG | AAT | GGC | AAG | GAC | TAC | AAG | TGC | AAG | GTC | TCC | AAC | AAA | GCC | CTC | CCA | 382 |
|-----|-----|-----|-----|-----|-----|-----|-----|-----|-----|-----|-----|-----|-----|-----|-----|-----|
| Leu | Asn | Gly | Lys | Asp | Tyr | Lys | Cys | Lys | Val | Ser | Asn | Lys | Ala | Leu | Pro |     |
|     |     |     | 115 |     |     |     |     | 120 |     |     |     |     | 125 |     |     |     |

| GCC | CCC | ATG | CAG | AAA | ACC | ATC | TCC | AAA | GCC | AAA | GGG | CAG | CCC | CGA | GAA | 430 |
|-----|-----|-----|-----|-----|-----|-----|-----|-----|-----|-----|-----|-----|-----|-----|-----|-----|
| Ala | Pro | Met | Gln | Lys | Thr | Ile | Ser | Lys | Ala | Lys | Gly | Gln | Pro | Arg | Glu |     |
|     |     | 130 |     |     |     |     | 135 |     |     |     |     | 140 |     |     |     |     |

| CCA | CAG | GTG | TAC | ACC | CTG | CCC | CCA | TCC | CGG | GAT | GAG | CTG | ACC | AAG | AAC | 478 |
|-----|-----|-----|-----|-----|-----|-----|-----|-----|-----|-----|-----|-----|-----|-----|-----|-----|
| Pro | Gln | Val | Tyr | Thr | Leu | Pro | Pro | Ser | Arg | Asp | Glu | Leu | Thr | Lys | Asn |     |
|     | 145 |     |     |     |     | 150 |     |     |     |     | 155 |     |     |     |     |     |

| CAG | GTC | AGC | CTG | ACC | TGC | CTG | GTC | AAA | GGC | TTC | TAT | CCC | AGG | CAC | ATC | 526 |
|-----|-----|-----|-----|-----|-----|-----|-----|-----|-----|-----|-----|-----|-----|-----|-----|-----|
| Gln | Val | Ser | Leu | Thr | Cys | Leu | Val | Lys | Gly | Phe | Tyr | Pro | Arg | His | Ile |     |
| 160 |     |     |     |     | 165 |     |     |     |     | 170 |     |     |     |     | 175 |     |

| GCC | GTG | GAG | TGG | GAG | AGC | AAT | GGG | CAG | CCG | GAG | AAC | AAC | TAC | AAG | ACC | 574 |
|-----|-----|-----|-----|-----|-----|-----|-----|-----|-----|-----|-----|-----|-----|-----|-----|-----|
| Ala | Val | Glu | Trp | Glu | Ser | Asn | Gly | Gln | Pro | Glu | Asn | Asn | Tyr | Lys | Thr |     |
|     |     |     |     | 180 |     |     |     |     | 185 |     |     |     |     | 190 |     |     |

| ACG | CCT | CCC | GTG | CTG | GAC | TCC | GAC | GGC | TCC | TTC | TTC | CTC | TAC | AGC | AAG | 622 |
|-----|-----|-----|-----|-----|-----|-----|-----|-----|-----|-----|-----|-----|-----|-----|-----|-----|
| Thr | Pro | Pro | Val | Leu | Asp | Ser | Asp | Gly | Ser | Phe | Phe | Leu | Tyr | Ser | Lys |     |
|     |     |     | 195 |     |     |     |     | 200 |     |     |     |     | 205 |     |     |     |

| CTC | ACC | GTG | GAC | AAG | AGC | AGG | TGG | CAG | CAG | GGG | AAC | GTC | TTC | TCA | TGC | 670 |
|-----|-----|-----|-----|-----|-----|-----|-----|-----|-----|-----|-----|-----|-----|-----|-----|-----|
| Leu | Thr | Val | Asp | Lys | Ser | Arg | Trp | Gln | Gln | Gly | Asn | Val | Phe | Ser | Cys |     |
|     |     " |210 |     |     |     |     | 215 |     |     |     |     | 220 |     |     |     |

| TCC | GTG | ATG | CAT | GAG | GCT | CTG | CAC | AAC | CAC | TAC | ACG | CAG | AAG | AGC | CTC | 718 |
|-----|-----|-----|-----|-----|-----|-----|-----|-----|-----|-----|-----|-----|-----|-----|-----|-----|
| Ser | Val | Met | His | Glu | Ala | Leu | His | Asn | His | Tyr | Thr | Gln | Lys | Ser | Leu |     |
|     | 225 |     |     |     |     | 230 |     |     |     |     | 235 |     |     |     |     |     |

| TCC | CTG | TCT | CCG | GGT | AAA | TGAACTAGT | | | | | | | | | | 745 |
|-----|-----|-----|-----|-----|-----|-----------|--|--|--|--|--|--|--|--|--|-----|
| Ser | Leu | Ser | Pro | Gly | Lys |           | | | | | | | | | | |
| 240 |     |     |     |     | 245 |           | | | | | | | | | | |

( 2 ) INFORMATION FOR SEQ ID NO:8:

( i ) SEQUENCE CHARACTERISTICS:
        ( A ) LENGTH: 245 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Val | Pro | Leu | Ala | Ser | Thr | Gly | Leu | Gly | Tyr | Arg | Tyr | Val | Glu | Pro | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Cys | Asp | Lys | Thr | His | Thr | Cys | Pro | Pro | Cys | Pro | Ala | Pro | Glu | Leu |

-continued

| | | 20 | | | | | 25 | | | | 30 | | |
|---|---|---|---|---|---|---|---|---|---|---|---|---|---|
| Leu | Gly | Gly 35 | Pro | Ser | Val | Phe | Leu 40 | Phe | Pro | Pro | Lys | Pro 45 | Lys | Asp | Thr |
| Leu | Met 50 | Ile | Ser | Arg | Thr | Pro 55 | Glu | Val | Thr | Cys | Val 60 | Val | Val | Asp | Val |
| Ser 65 | His | Glu | Asp | Pro | Glu 70 | Val | Lys | Phe | Asn | Trp 75 | Tyr | Val | Asp | Gly | Val 80 |
| Glu | Val | His | Asn | Ala 85 | Lys | Thr | Lys | Pro | Arg 90 | Glu | Glu | Gln | Tyr | Asn 95 | Ser |
| Thr | Tyr | Arg | Val 100 | Val | Ser | Val | Leu | Thr 105 | Val | Leu | His | Gln | Asp 110 | Trp | Leu |
| Asn | Gly | Lys 115 | Asp | Tyr | Lys | Cys | Lys 120 | Val | Ser | Asn | Lys | Ala 125 | Leu | Pro | Ala |
| Pro | Met 130 | Gln | Lys | Thr | Ile | Ser 135 | Lys | Ala | Lys | Gly | Gln 140 | Pro | Arg | Glu | Pro |
| Gln 145 | Val | Tyr | Thr | Leu | Pro 150 | Pro | Ser | Arg | Asp | Glu 155 | Leu | Thr | Lys | Asn | Gln 160 |
| Val | Ser | Leu | Thr | Cys 165 | Leu | Val | Lys | Gly | Phe 170 | Tyr | Pro | Arg | His | Ile 175 | Ala |
| Val | Glu | Trp | Glu 180 | Ser | Asn | Gly | Gln | Pro 185 | Glu | Asn | Asn | Tyr | Lys 190 | Thr | Thr |
| Pro | Pro | Val 195 | Leu | Asp | Ser | Asp | Gly 200 | Ser | Phe | Phe | Leu | Tyr 205 | Ser | Lys | Leu |
| Thr | Val 210 | Asp | Lys | Ser | Arg | Trp 215 | Gln | Gln | Gly | Asn | Val 220 | Phe | Ser | Cys | Ser |
| Val 225 | Met | His | Glu | Ala | Leu 230 | His | Asn | His | Tyr | Thr 235 | Gln | Lys | Ser | Leu | Ser 240 |
| Leu | Ser | Pro | Gly | Lys 245 | | | | | | | | | | | |